United States Patent
Ay et al.

(10) Patent No.: US 11,439,508 B2
(45) Date of Patent: Sep. 13, 2022

(54) 3D MODELING SYSTEMS AND METHODS

(71) Applicant: Fited, Inc., Teaneck, NJ (US)

(72) Inventors: Mehmet Erdem Ay, Teaneck, NJ (US); Akanksha Vyas, West Mumbai (IN)

(*) Notice: Subject to any disclaimer, the term of this patent is extended or adjusted under 35 U.S.C. 154(b) by 548 days.

(21) Appl. No.: 15/828,430

(22) Filed: Nov. 30, 2017

(65) Prior Publication Data

US 2018/0147062 A1    May 31, 2018

Related U.S. Application Data

(60) Provisional application No. 62/428,004, filed on Nov. 30, 2016.

(51) Int. Cl.
*G06T 19/20* (2011.01)
*A61F 2/30* (2006.01)
(Continued)

(52) U.S. Cl.
CPC .......... *A61F 2/30942* (2013.01); *G06F 30/00* (2020.01); *G06T 17/00* (2013.01); *G06T 17/10* (2013.01); *G06T 19/20* (2013.01); *A61F 2002/30943* (2013.01); *G06F 2111/04* (2020.01); *G06T 2210/41* (2013.01); *G06T 2219/2004* (2013.01); *G06T 2219/2021* (2013.01)

(58) Field of Classification Search
CPC ....... A61F 2/30942; A61F 2002/30943; G06F 30/00; G06F 2111/04; G06T 17/00; G06T 17/10; G06T 19/20; G06T 2210/41; G06T 2219/2004; G06T 2219/2021
See application file for complete search history.

(56) References Cited

U.S. PATENT DOCUMENTS 5,844,564 A    12/1998    Bennis et al.
6,133,921 A    10/2000    Turkiyyah et al.
(Continued)

FOREIGN PATENT DOCUMENTS

WO    WO 2015/089118    6/2015
WO    WO 2018/102625    6/2018

OTHER PUBLICATIONS

Fortin, D., Farida Cheriet, M. Beausejour, Philippe Debanné, Julie Joncas, and Hubert Labelle. "A 3D visualization tool for the design and customization of spinal braces." Computerized Medical Imaging and Graphics 31, No. 8 (2007): 614-624. (Year: 2007).*

(Continued)

*Primary Examiner* — Chuen-Meei Gan
(74) *Attorney, Agent, or Firm* — Levine Bagade Han LLP

(57) ABSTRACT

Systems and methods for creating a geometric design definition for 3D models designed to fit physical or digital template objects is disclosed. The 3D models can transform to fit specific physical or digital objects which are different from but topologically isomorphic to the original template objects based on visual or mathematical inputs. To validate the fit, the generated 3D model can be compared with the specific physical or digital objects for which the 3D model is generated to fit, and the geometry of generated 3D model can be adjusted to improve the fit if the generated 3D model is not validated. The accuracy of the fit of the generated 3D models can be improved iteratively.

39 Claims, 29 Drawing Sheets

(51) Int. Cl.
*G06T 17/00* (2006.01)
*G06F 30/00* (2020.01)
*G06T 17/10* (2006.01)
*G06F 111/04* (2020.01)

(56) References Cited

U.S. PATENT DOCUMENTS

| | | | |
|---|---|---|---|
| 6,268,846 | B1 | 7/2001 | Georgiev |
| 6,606,091 | B2 | 8/2003 | Liang et al. |
| 6,606,528 | B1 | 8/2003 | Hagmeier et al. |
| 6,903,738 | B2 | 6/2005 | Pfister et al. |
| 6,912,293 | B1 | 6/2005 | Korobkin |
| 7,305,121 | B2 | 3/2007 | Kaufmann et al. |
| 7,747,305 | B2 | 6/2010 | Dean et al. |
| D792,692 | S | 7/2017 | Schouwenburg et al. |
| 9,760,674 | B2 | 9/2017 | Schouwenburg et al. |
| 2010/0284607 | A1 | 11/2010 | Van Den Hengel et al. |
| 2011/0161058 | A1* | 6/2011 | Schottdorf ............... A61B 6/04 703/1 |
| 2013/0166256 | A1* | 6/2013 | Wirx-Speetjens ...... G06F 30/00 703/1 |
| 2014/0052415 | A1 | 2/2014 | Baran et al. |
| 2014/0081190 | A1* | 3/2014 | Summit ................. A61F 5/013 602/19 |
| 2015/0032242 | A1* | 1/2015 | Schouwenburg ....... G06F 30/00 700/98 |
| 2015/0089118 | A1 | 3/2015 | In et al. |
| 2015/0265362 | A1 | 9/2015 | Andersson et al. |
| 2016/0101572 | A1 | 4/2016 | Schouwenburg et al. |
| 2016/0310064 | A1* | 10/2016 | Cheng .................... A61B 5/486 |
| 2016/0339607 | A1* | 11/2016 | Munoz ................... A61F 5/058 |
| 2017/0173289 | A1* | 6/2017 | Lucey .................... G06N 20/10 |
| 2017/0190121 | A1* | 7/2017 | Aggarwal .............. B33Y 80/00 |
| 2018/0095450 | A1* | 4/2018 | Lappas .................. B29C 64/10 |

OTHER PUBLICATIONS

Baek, Seung-Yeob, and Kunwoo Lee. "Parametric human body shape modeling framework for human-centered product design." Computer-Aided Design 44, No. 1 (2012): 56-67. (Year: 2012).*

Colombo G, Filippi S, Rizzi C, Rotini F. A new design paradigm for the development of custom-fit soft sockets for lower limb prostheses. Computers in Industry. Aug. 1, 2010;61(6):513-23. (Year: 2010).*

Anonymous: "Point set registration—Wikipedia", 7 pages, Aug. 1, 2016.

Jin, Y. et al. "Additive Manufacturing of Custom Orthoses and Prostheses—A Review", *Procedia Cirp*, vol. 36, pp. 199-204, Jan. 1, 2015.

Liu, H. et al. "Three-dimensional surface registration: A neural network strategy," *Neurocomputing*, vol. 70, No. 1-3, pp. 597-602, Jun. 6, 2006.

Schrank, E.S. et al. "Dimensional accuracy of ankle-foot orthoses constructed by rapid customization and manufacturing framework," *Journal of Rehabilitation Research and Development*, vol. 48, No. 1, pp. 31-42, Jan. 11, 2011.

* cited by examiner

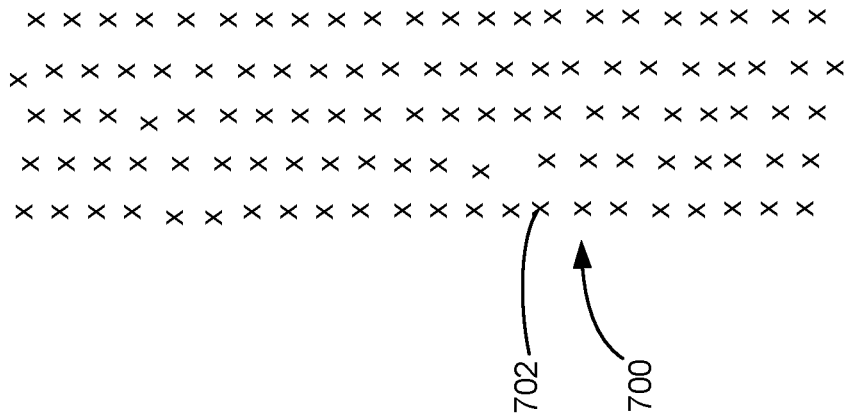
FIG. 13C
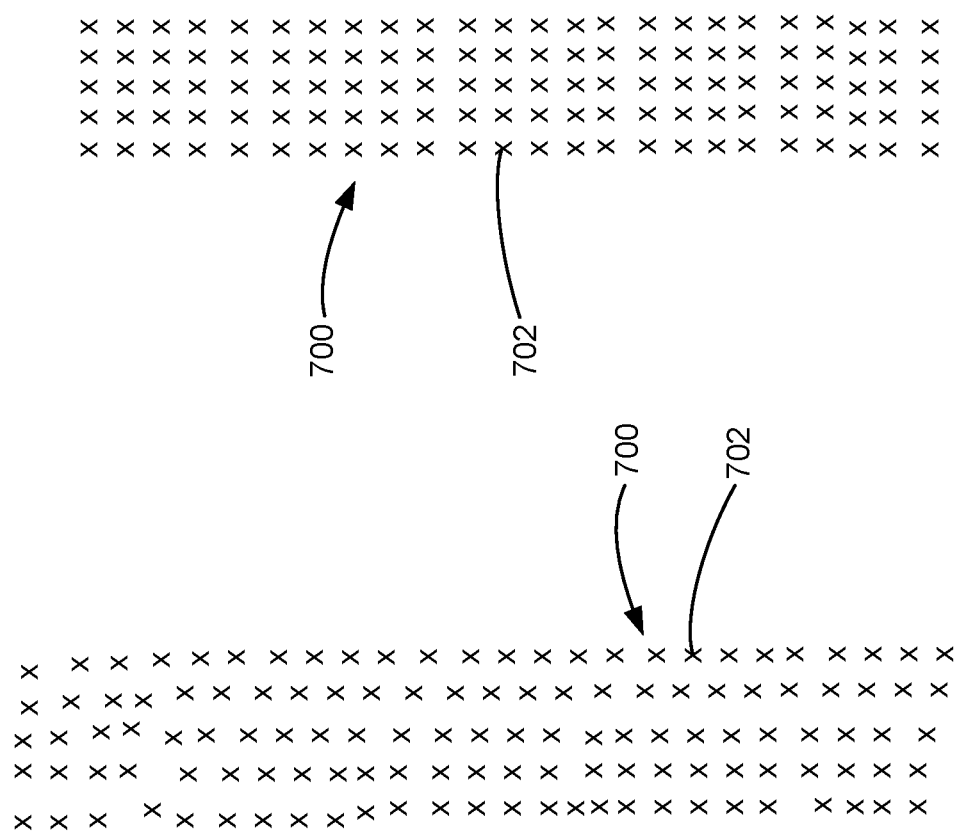
FIG. 13B
FIG. 13A

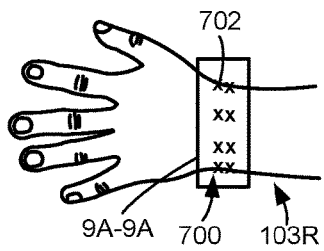
FIG. 14A₁
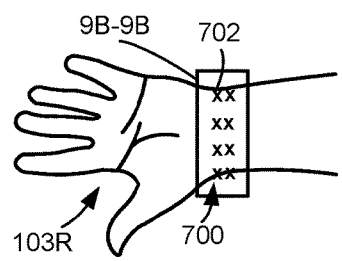
FIG. 14B₁
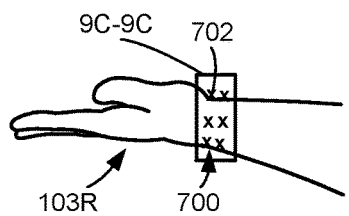
FIG. 14C₁
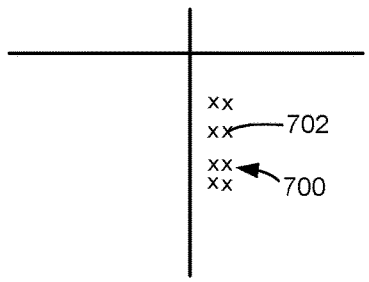
FIG. 14A₂
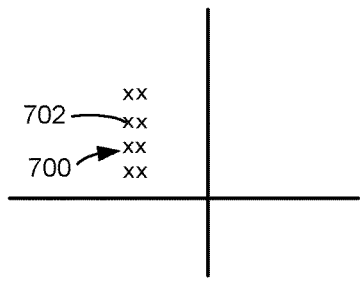
FIG. 14B₂
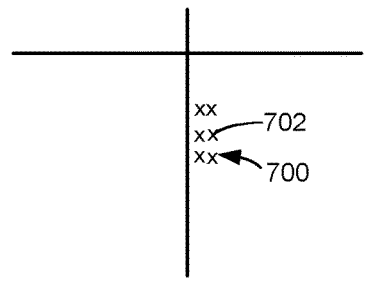
FIG. 14C₂
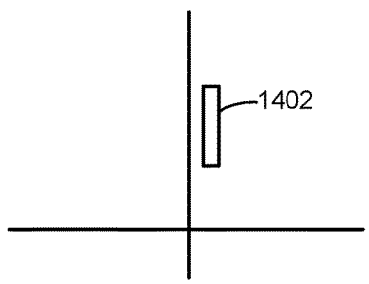
FIG. 14A₃
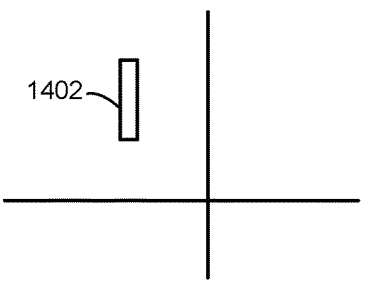
FIG. 14B₃
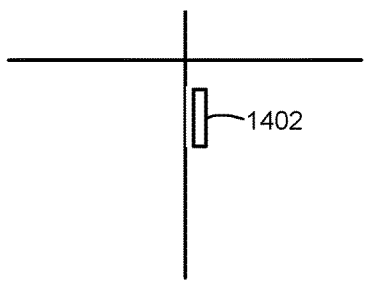
FIG. 14C₃
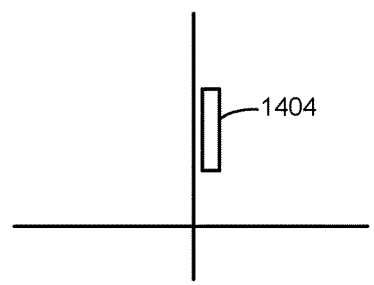
FIG. 14A₄
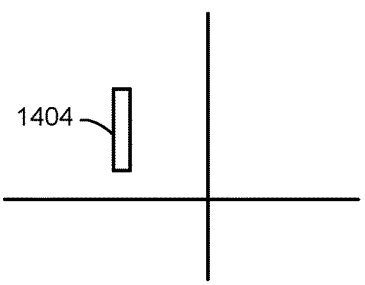
FIG. 14B₄
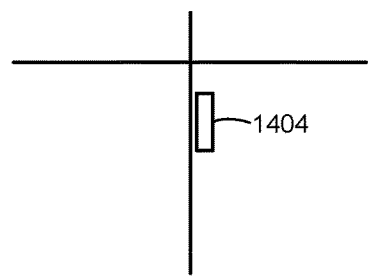
FIG. 14C₄

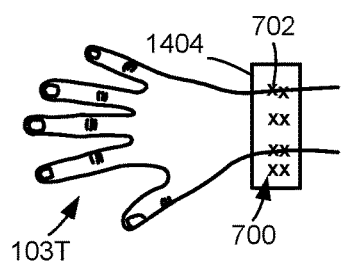
FIG. 17A₁
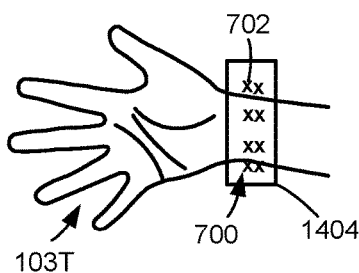
FIG. 17B₁
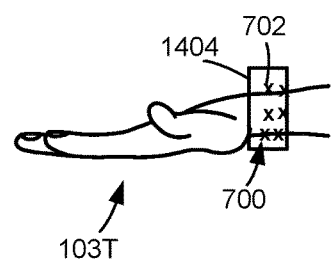
FIG. 17C₁
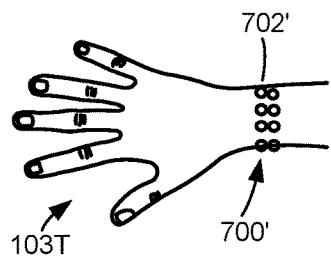
FIG. 17A₂
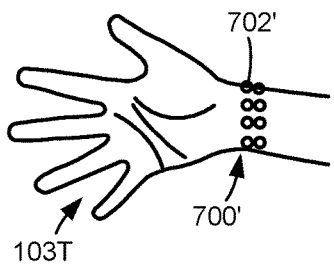
FIG. 17B₂
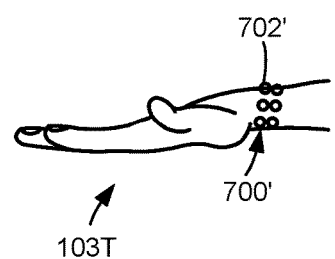
FIG. 17C₂
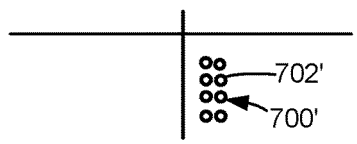
FIG. 17A₃
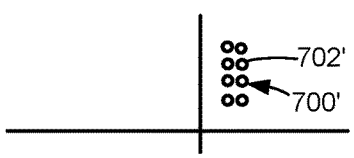
FIG. 17B₃
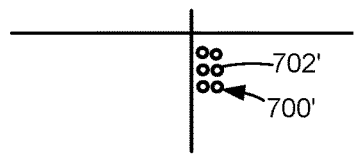
FIG. 17C₃
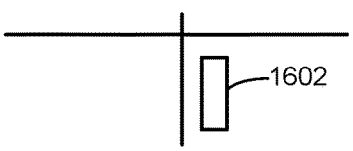
FIG. 17A₄
FIG. 17B₄
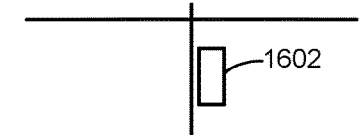
FIG. 17C₄
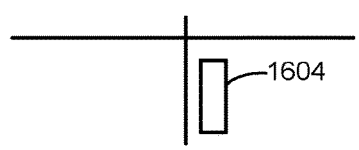
FIG. 17A₅
FIG. 17B₅
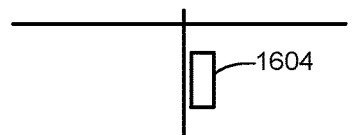
FIG. 17C₅

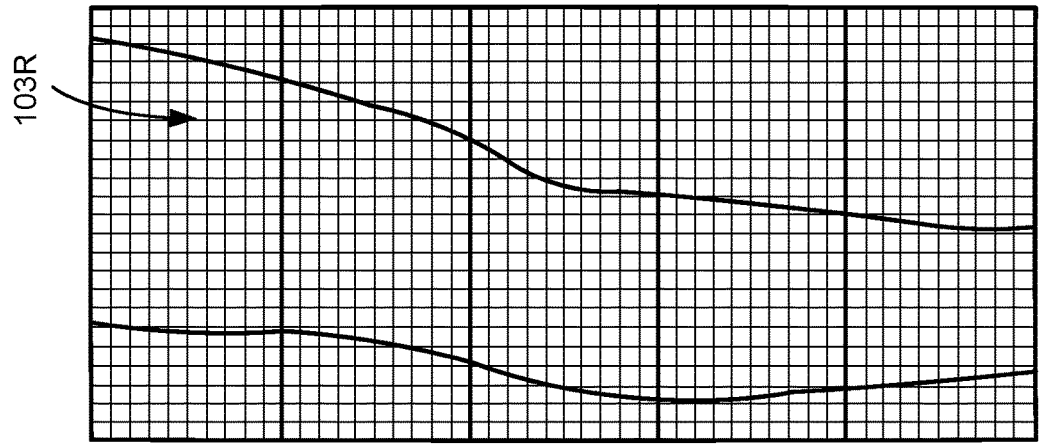
FIG. 20C₁
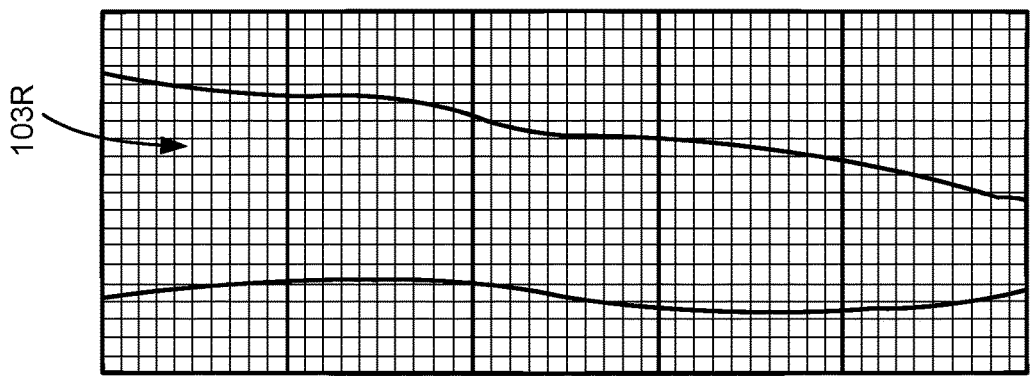
FIG. 20B₁
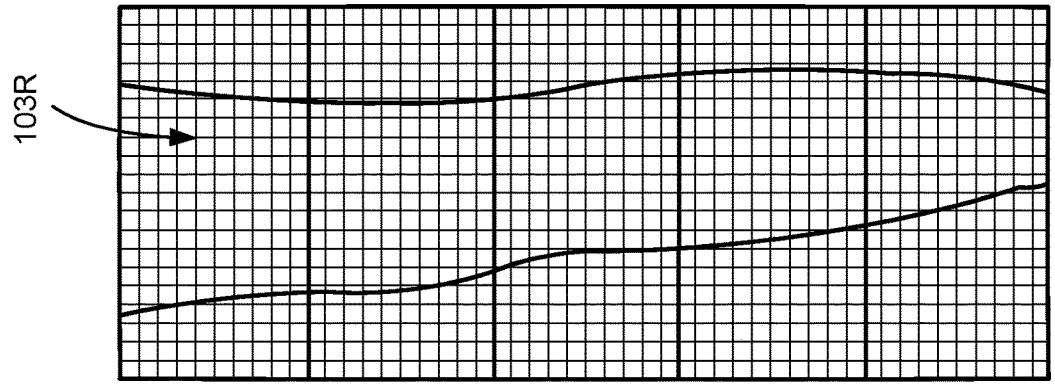
FIG. 20A₁

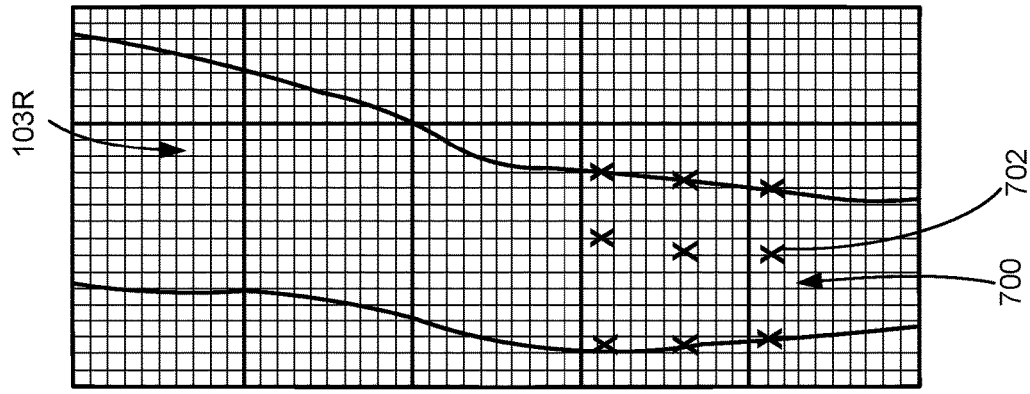
FIG. 20C₂
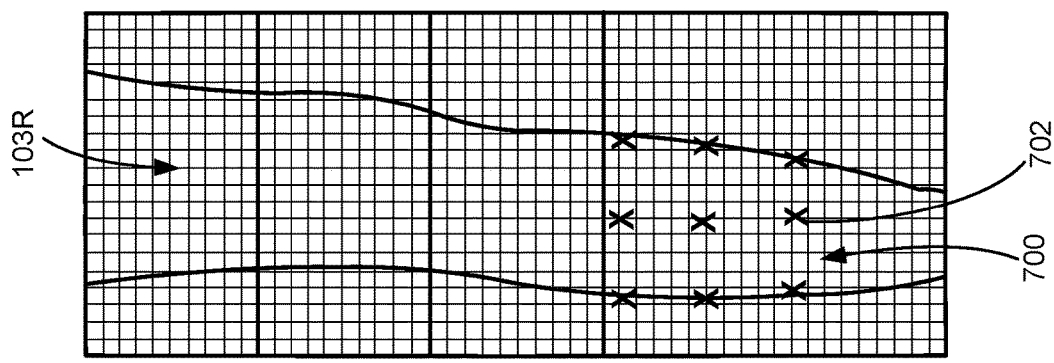
FIG. 20B₂
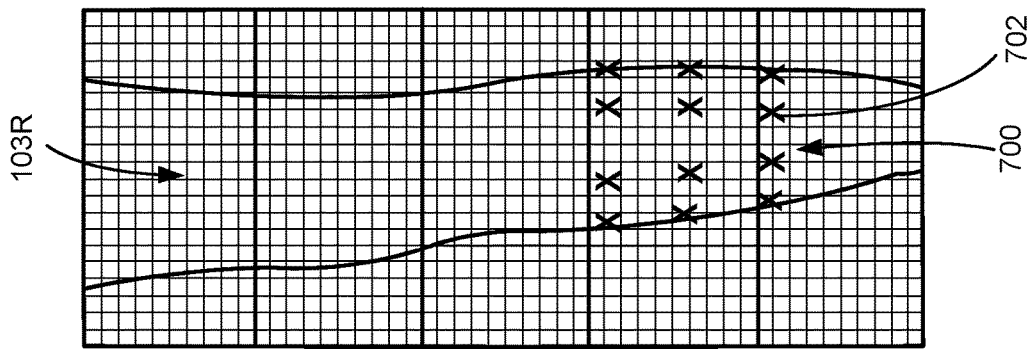
FIG. 20A₂

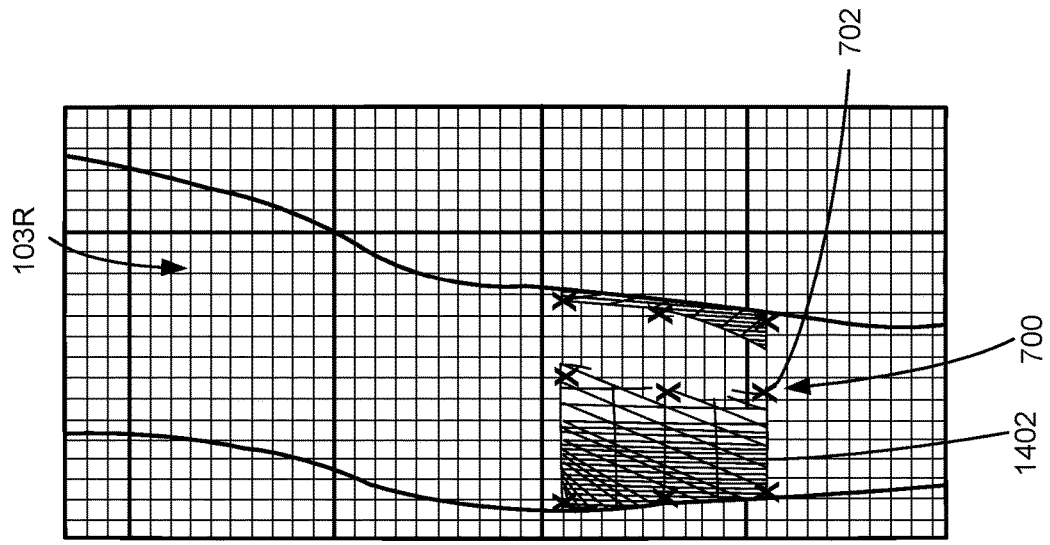
FIG. 20C₃
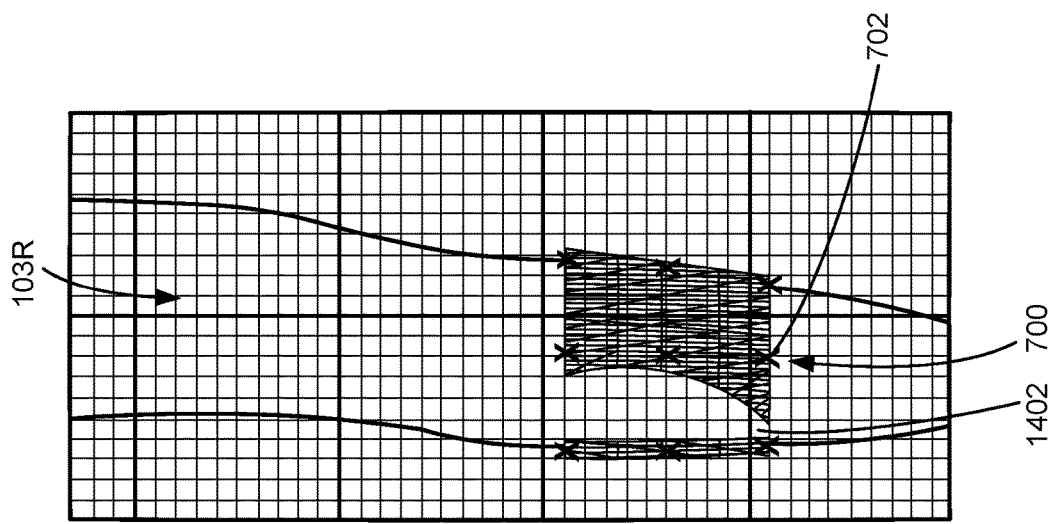
FIG. 20B₃
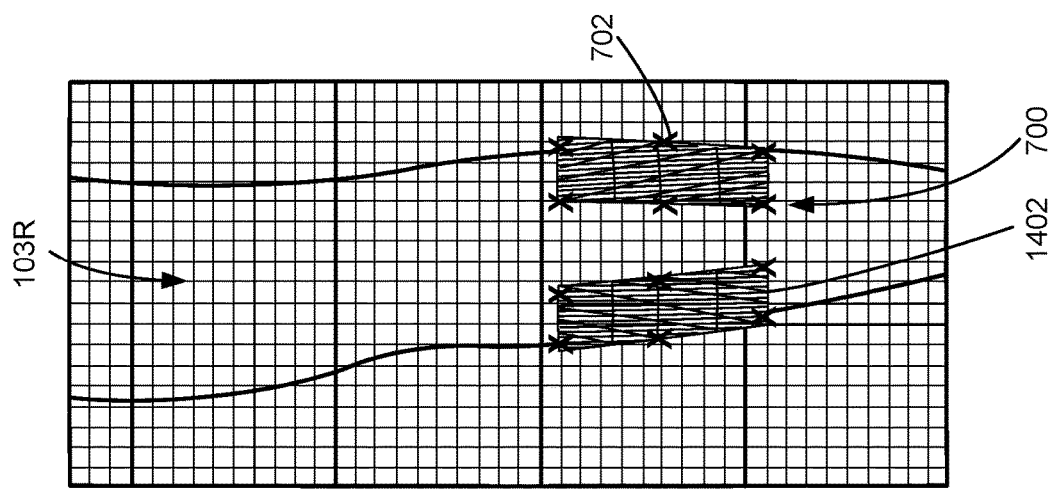
FIG. 20A₃

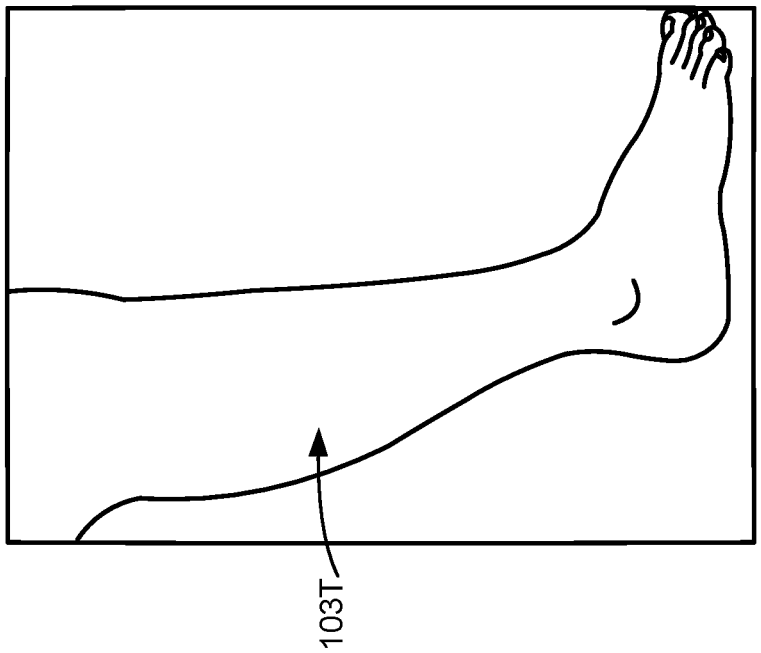
FIG. 20C₄
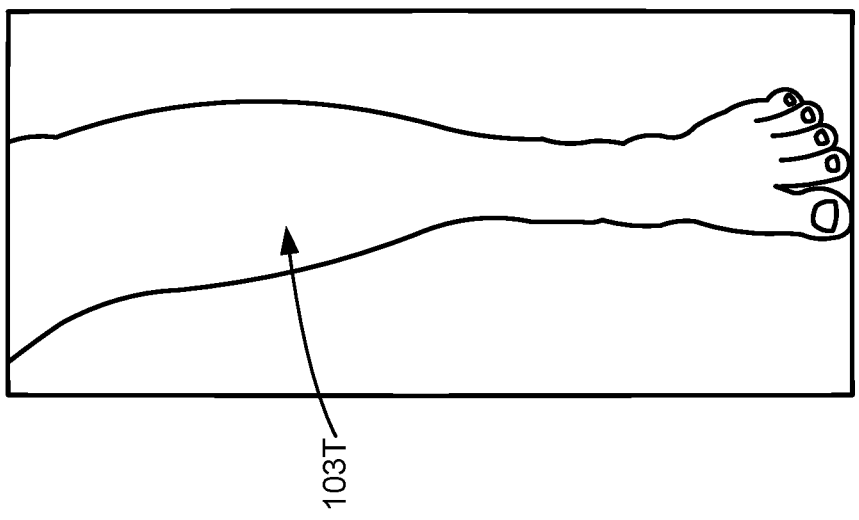
FIG. 20B₄
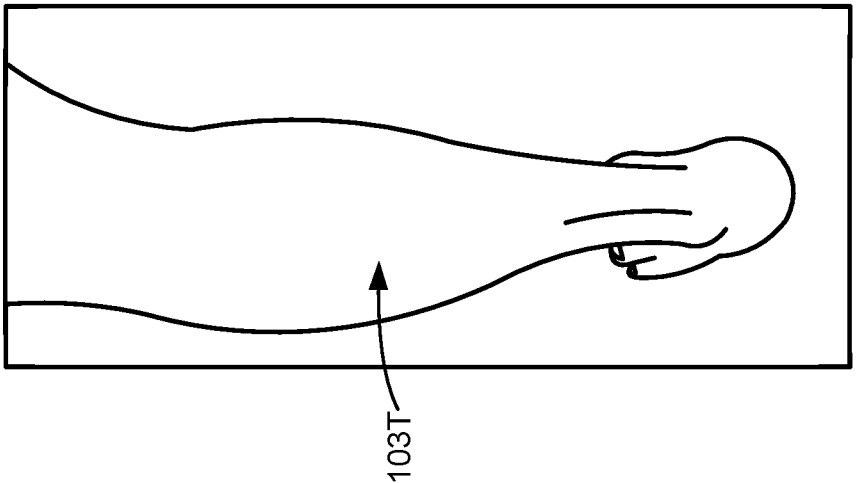
FIG. 20A₄

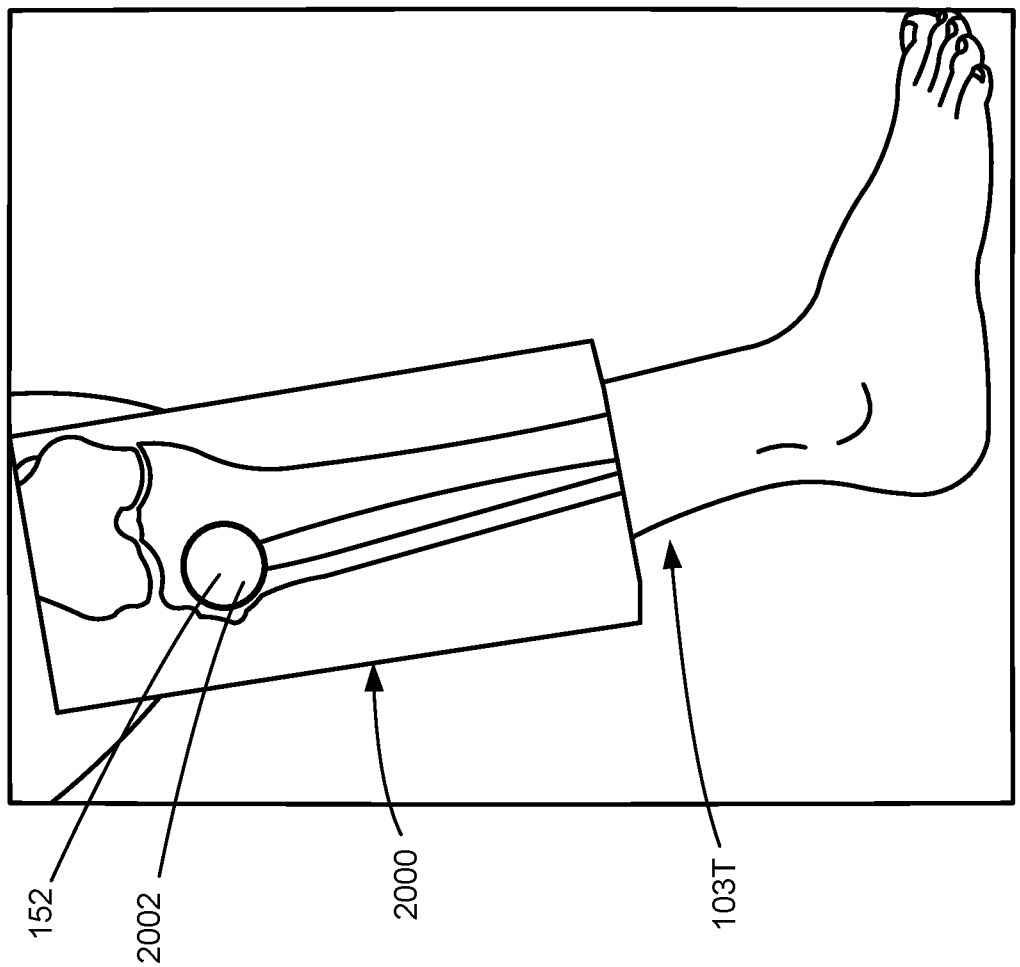
FIG. 20C₄ₓ

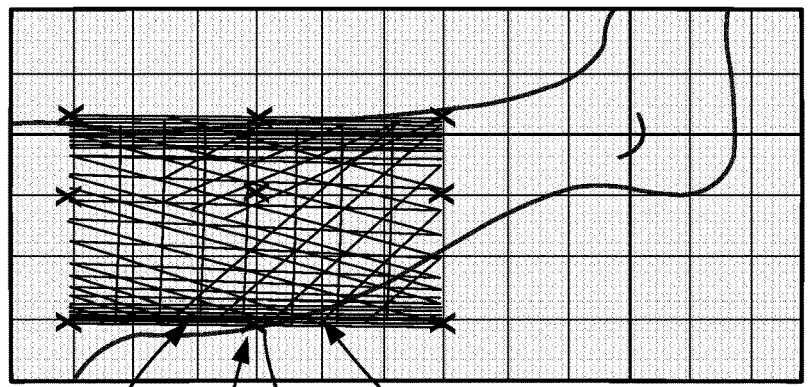
FIG. 20C₅
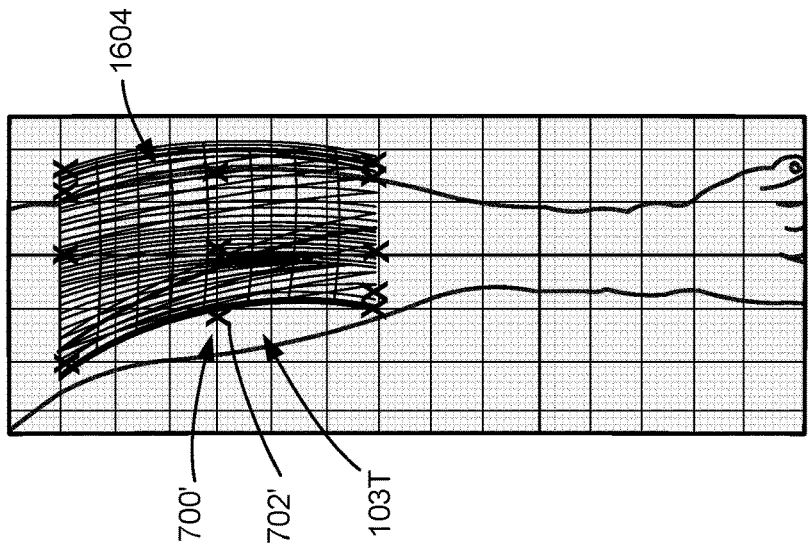
FIG. 20B₅
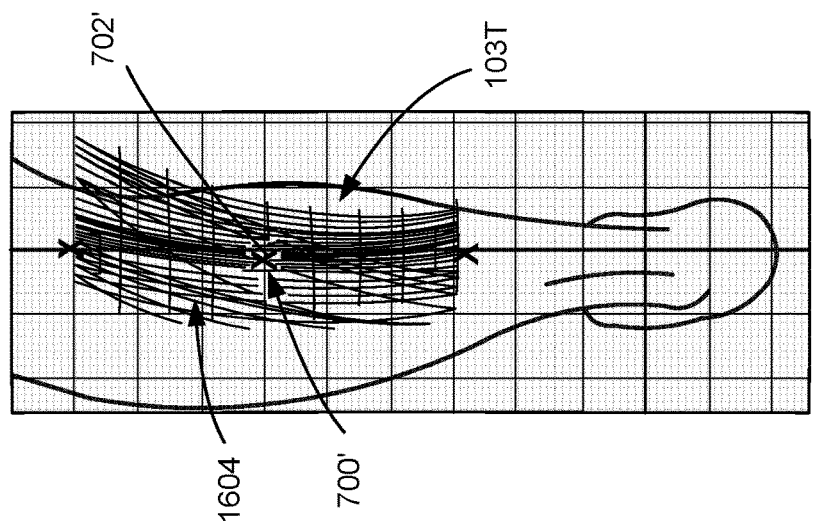
FIG. 20A₅

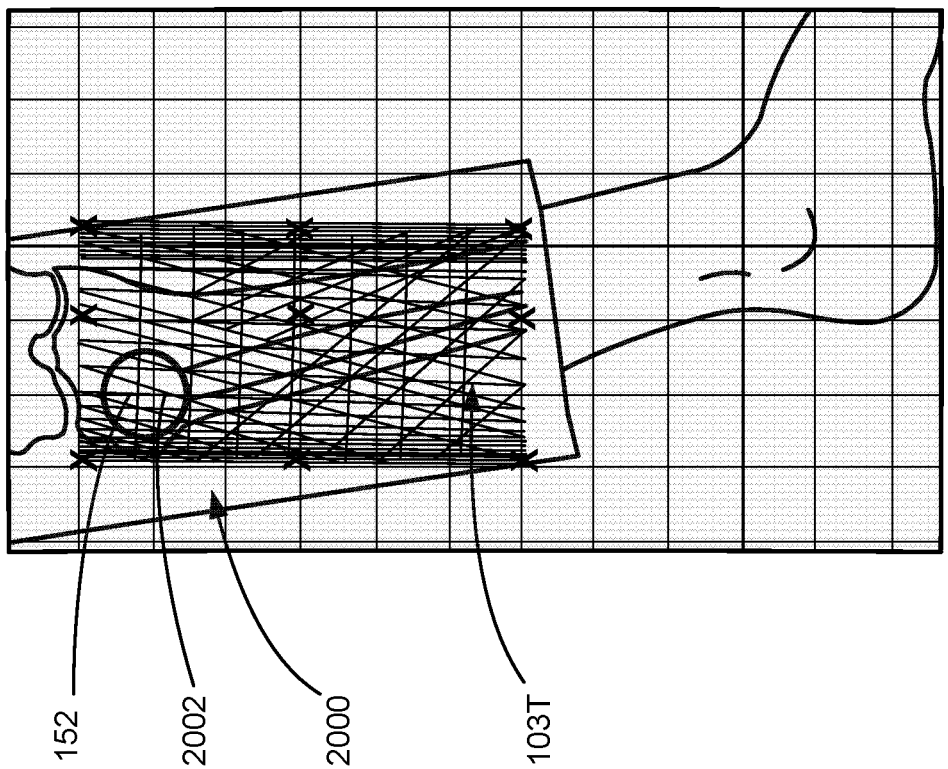
FIG. 20C$_{5x}$

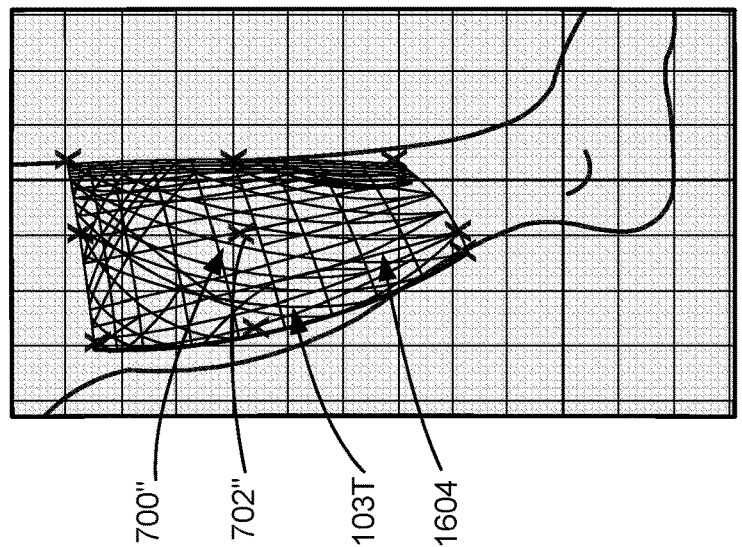
FIG. 20C₆
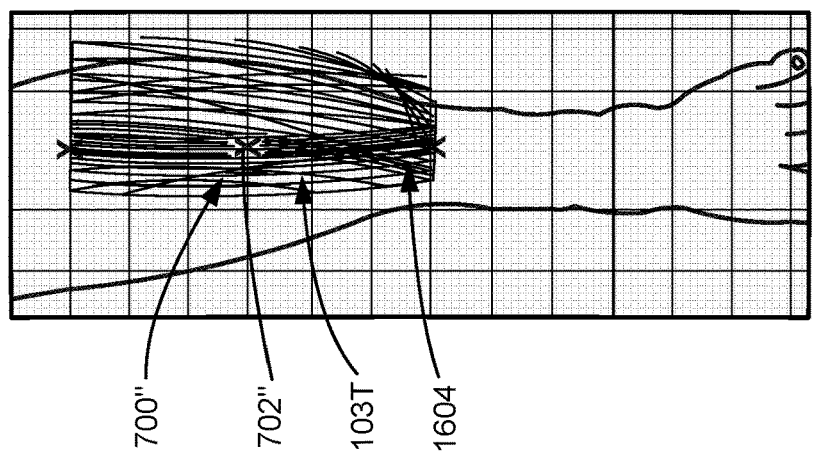
FIG. 20B₆
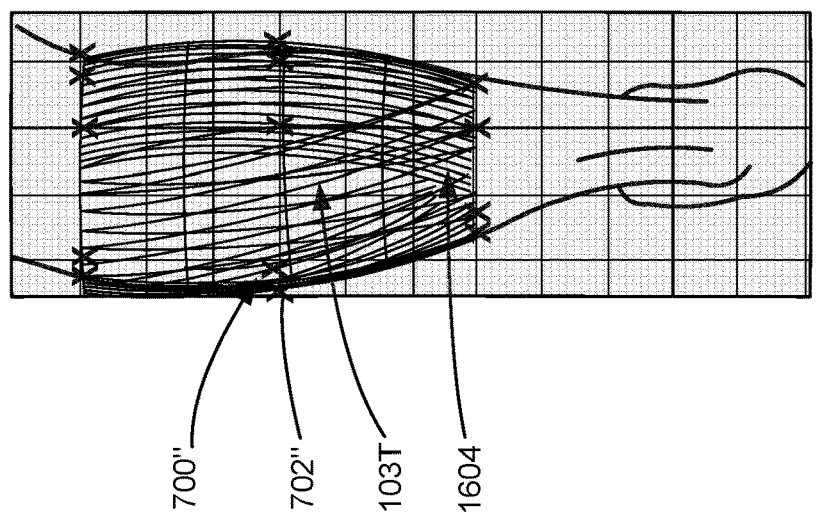
FIG. 20A₆

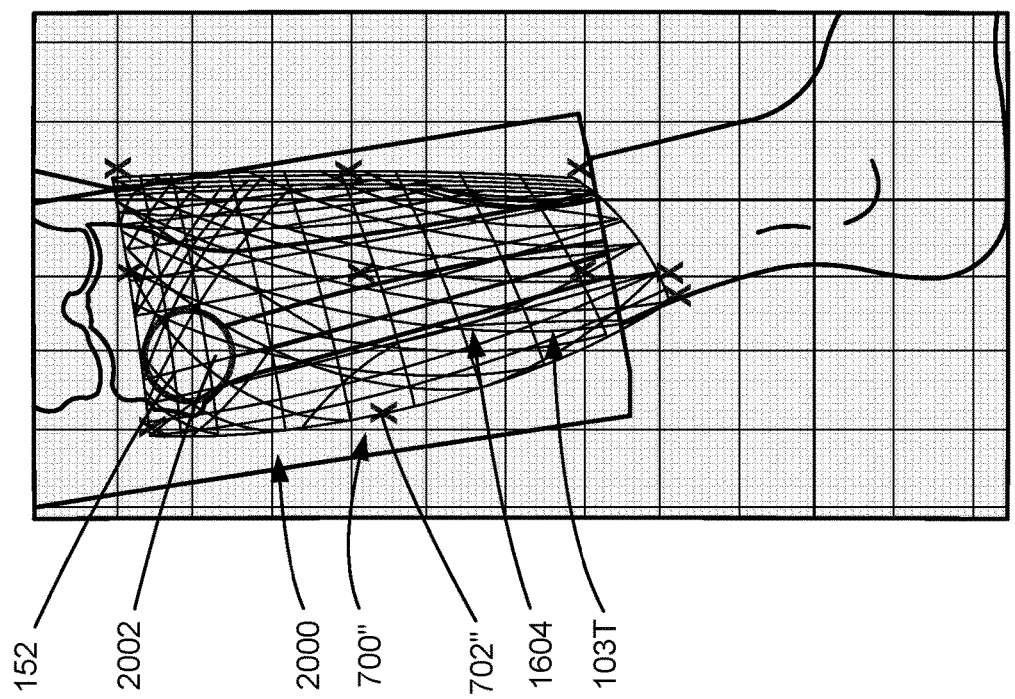
FIG. 20C₆ₓ

3D MODELING SYSTEMS AND METHODS

CROSS-REFERENCE TO RELATED APPLICATION

This application claims priority to U.S. Provisional Application No. 62/428,004 filed Nov. 30, 2016, which is herein incorporated by reference in its entirety for all purposes.

BACKGROUND

1. Technical Field 3D modeling systems and methods of using the same are disclosed. More specifically, systems and methods for creating geometric design definitions and generating 3D models based on these definitions are disclosed.

2. Background of the Art 3D modeling is the process of creating digital mathematical representations of 3D objects, known as 3D models. 3D Computer Aided Design (CAD) modeling is a technique for creating 3D models. There are many computer applications for 3D CAD modeling that provide the tools for designers to create these 3D representations (models) of objects. 3D models are also created computationally, using data from 3D scanners, sensors, and other forms of input data.

The 3D models are often subsequently manufactured with 3D printers, CNC machines, and other milling machines to be used in physical environments, or used as 2D or 3D rendering of 3D models in digital environments for games, animated movies, virtual reality applications, augmented reality applications, etc.

Creating 3D models that are custom fit to an object is a popular application of 3D modeling. Though the degree of accuracy required may differ based on the specific use-case, these 3D models are designed to exactly fit unique physical or digital objects. Existing methods that use 3D CAD modeling to create custom fit models are time-consuming, error prone, and require expensive human resources. Existing methods that use computational methods to create custom fit 3D models are created in sizes using measurements, which have a low accuracy. Current methods also involve individually designing each 3D model for each product, which results in large variations in 3D model accuracy since each 3D model is being designed by a user sitting at a software interface and prone to human error.

This disclosure relates to modeling 3D models that computationally adapt to fit unique physical or digital objects and iteratively improving the accuracy of such fits, and to providing improved mass customization techniques for the creation of 3D models.

BRIEF SUMMARY

This disclosure relates generally to generating 3D models.
More specifically, this disclosure relates to generating 3D models at least partly from a geometric design definition.

Methods of creating 3D models of structures are disclosed. For example, a method is disclosed that can include acquiring a digital representation of a first object. The method can include determining a geometric design definition of a structure first 3D model, where the structure first 3D model is configured to fit the first object. The method can include acquiring a digital representation of a second object. The method can include computing the geometric design definition to generate a structure second 3D model, where the structure second 3D model is configured to fit the second object. The method can include validating the structure second 3D model upon confirming that the structure second 3D model satisfies fit accuracy parameters.

Methods for creating 3D models are disclosed. For example, a method is disclosed that can include acquiring a digital representation of a reference object. The method can include determining a geometric design definition of a 3D reference model configured to fit the reference object. The geometric design definition can have a fit accuracy requirement that defines the fit between the 3D reference model and the reference object. The geometric design definition can have a 3D reference coordinate map of the 3D reference model based at least partly on the fit accuracy requirement. The geometric design definition can have geometric constructs of the 3D reference model. The method can include acquiring a digital representation of a target object. The method can include computing the geometric design definition to generate a first 3D target model designed to fit the target object. Computing the geometric design definition can include determining a 3D target coordinate map for the target object. Computing the geometric design definition can include substituting the 3D target coordinate map into the geometric design definition. Computing the geometric design definition can include computing the geometric design definition with the 3D target coordinate map to generate the first 3D target model. The method can include validating the first 3D target model upon confirming that the first 3D target model satisfies the fit accuracy requirement. The method can include improving the geometric design definition using one or more learning modules. The learning modules can be configured to reference one or more validated 3D target models and the computed geometric design definitions associated therewith.

3D modeling systems are disclosed. For example, a system is disclosed that can have one or more data acquisition devices and a modeling unit. The modeling unit can be configured to process reference and target objects acquired from the one or more data acquisition devices. The modeling unit can be configured to design a 3D reference model to fit the reference object by determining fit accuracy parameters and creating a 3D reference coordinate map of the 3D reference model based at least partly on the fit accuracy parameters. The modeling unit can be configured to generate a first 3D target model based on a 3D target coordinate map derived at least partly from the 3D reference coordinate map. The modeling unit can be configured to validate the first 3D target model upon confirming that the first 3D target model satisfies the fit accuracy parameters. The modeling unit can be configured to improve the derivation of the 3D target coordinate map using one or more learning modules. The learning modules can be configured to reference one or more validated 3D target models and the computed geometric design definitions associated therewith.

BRIEF DESCRIPTION OF THE DRAWINGS

The drawings shown and described are exemplary embodiments and non-limiting. Like reference numerals indicate identical or functionally equivalent features throughout.

FIG. 13A is a variation of the 3D coordinate map of FIG. 12A stripped from the digital representation of the reference object.

FIG. 13B is a variation of the 3D coordinate map of FIG. 12B stripped from the digital representation of the reference object.

FIG. 13C is a variation of the 3D coordinate map of FIG. 12C stripped from the digital representation of the reference object.

Figure 8A:
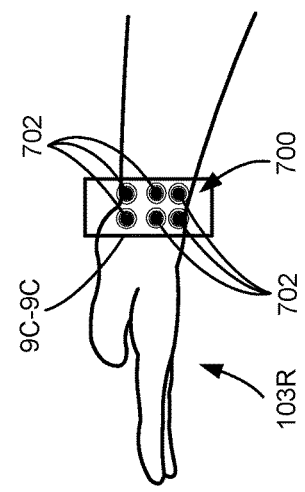
FIG. 8A illustrates a variation of a 3D coordinate map applied to the digital representation of FIG. 7A.

FIG. $14A_1$ illustrates the reference object and 3D coordinate mapping of FIG. 8A.

FIG. $14A_2$ illustrates the 3D coordinate map of FIG. $14A_1$ without the digital representation of the reference object.

FIG. $14A_3$ illustrates a variation of a lattice structure created from the 3D coordinate map of FIG. $14A_2$.

FIG. $14A_4$ illustrates a variation of a 3D reference model created from the lattice structure of FIG. $14A_3$.

Figure 8B:
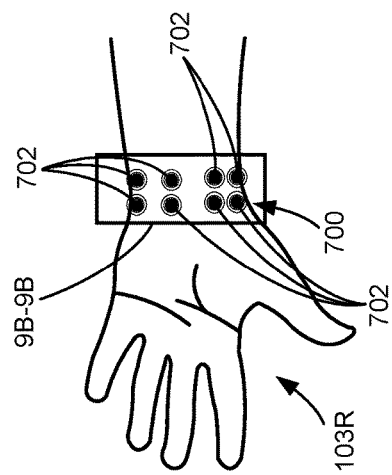
FIG. 8B illustrates a variation of a 3D coordinate map applied to the digital representation of FIG. 7B.

FIG. $14B_1$ illustrates the reference object and 3D coordinate mapping of FIG. 8B.

FIG. $14B_2$ illustrates the 3D coordinate map of FIG. $14B_1$ without the digital representation of the reference object.

FIG. $14B_3$ illustrates a variation of a lattice structure created from the 3D coordinate map of FIG. $14B_2$.

FIG. $14B_4$ illustrates a variation of a 3D reference model created from the lattice structure of FIG. $14B_3$.

Figure 8C:
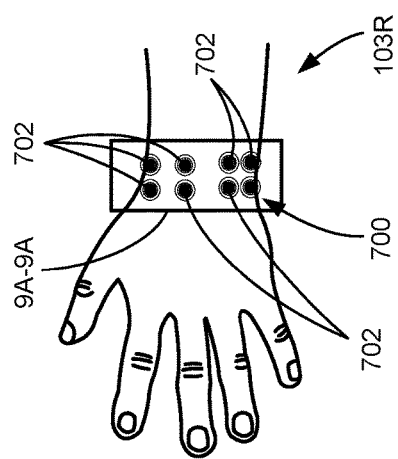
FIG. 8C illustrates a variation of a 3D coordinate map applied to the digital representation of FIG. 7C.

FIG. $14C_1$ illustrates the reference object and 3D coordinate mapping of FIG. 8C.

FIG. $14C_2$ illustrates the 3D coordinate map of FIG. $14C_1$ without the digital representation of the reference object.

FIG. $14C_3$ illustrates a variation of a lattice structure created from the 3D coordinate map of FIG. $14C_2$.

FIG. $14C_4$ illustrates a variation of a 3D reference model created from the lattice structure of FIG. $14C_3$.

Figure 15A:
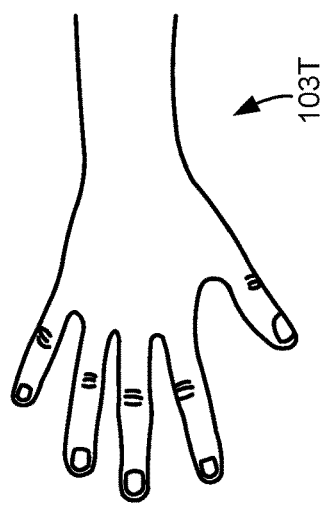

FIG. 15A illustrates a variation of a digital representation of a top view of a target object.

Figure 9C:
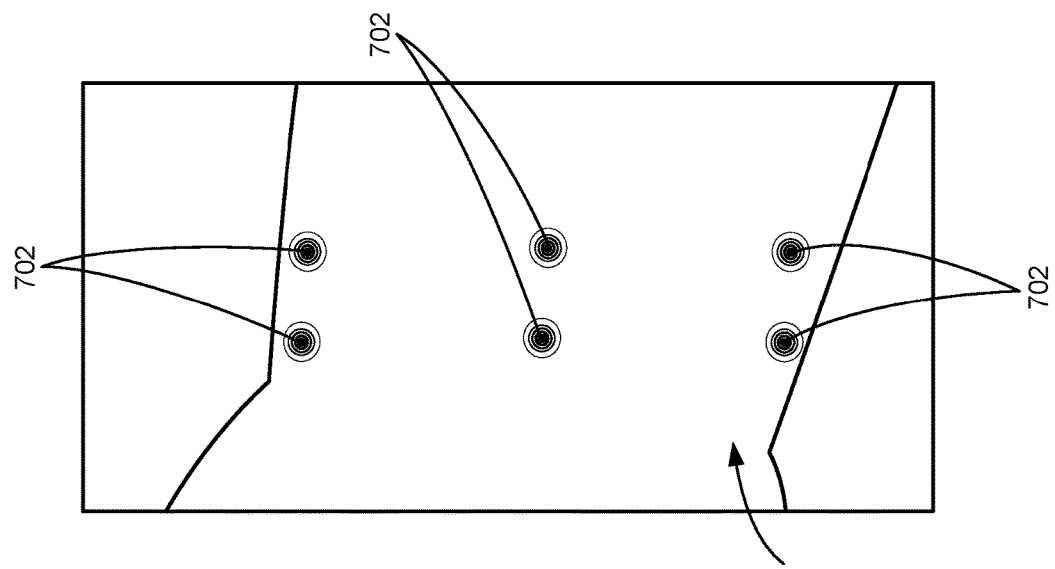
FIG. 9C is a magnified view of the 3D coordinate map of FIG. 8C at section 9C-9C.
Figure 9B:
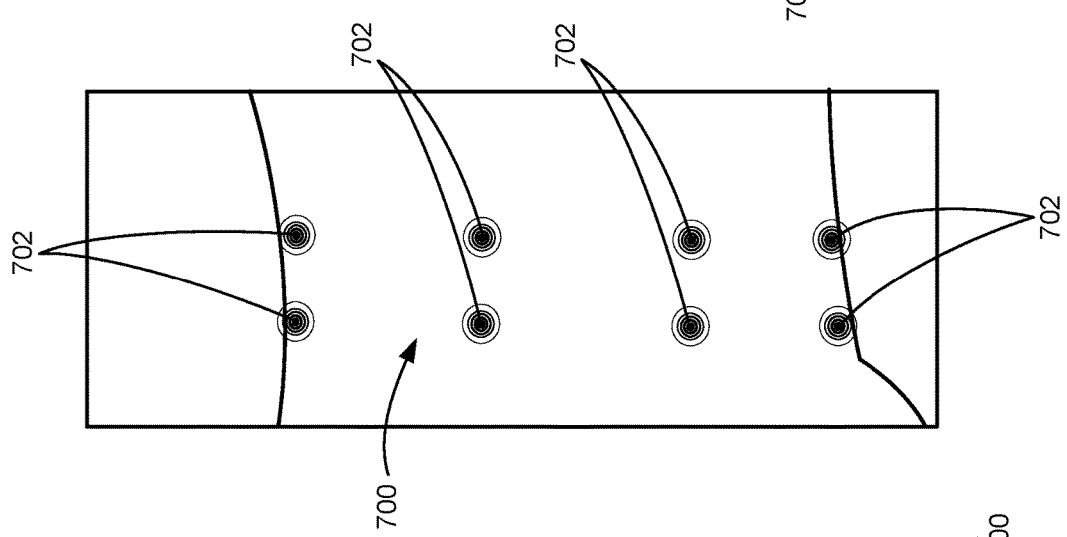
FIG. 9B is a magnified view of the 3D coordinate map of FIG. 8B at section 9B-9B.
Figure 9A:
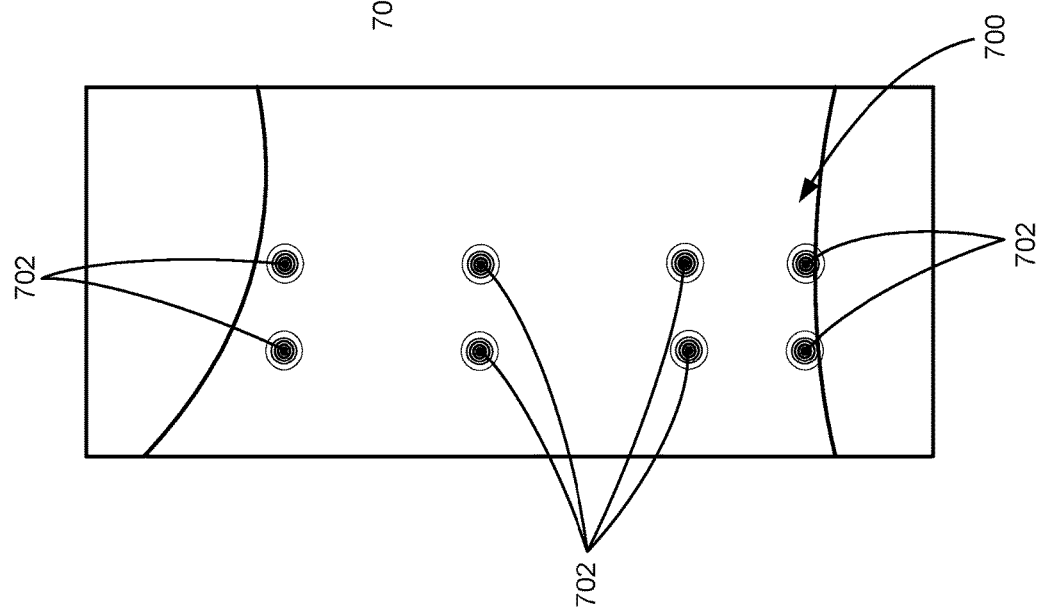
FIG. 9A is a magnified view of the 3D coordinate map of FIG. 8A at section 9A-9A.
Figure 15B:
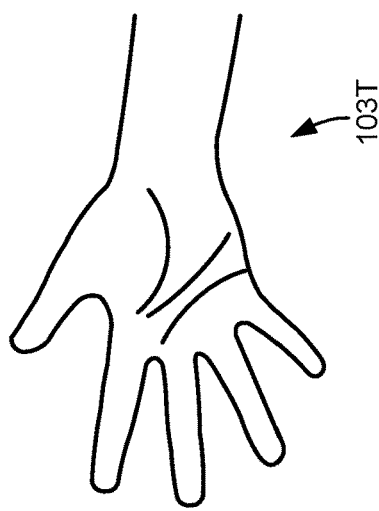

FIG. 15B illustrates a variation of a digital representation of a bottom view of the target object of FIG. 9A.

Figure 15C:
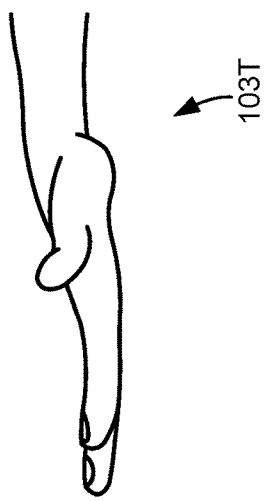

FIG. 15C illustrates a variation of a digital representation of a side view of the target object of FIG. 9A.

Figure 16A:
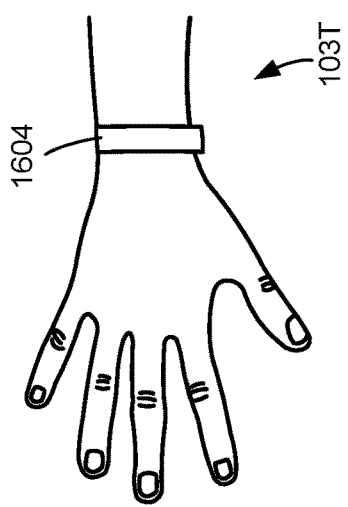

FIG. 16A illustrates a variation of a 3D model of a generated, adjusted, and/or validated 3D target model that fits the target object of FIG. 9A.

Figure 16B:
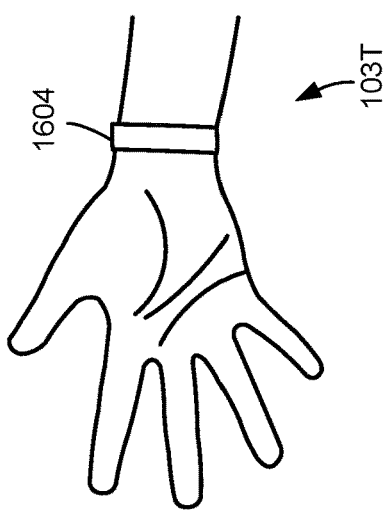

FIG. 16B illustrates a variation of a 3D model of a 3D target model that fits the target object of FIG. 15B.

Figure 16C:
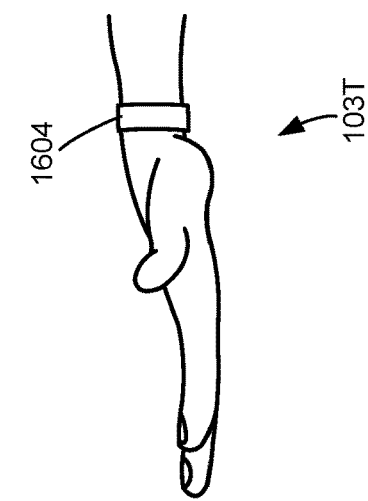

FIG. 16C illustrates a variation of a 3D model of a 3D target model that fits the target object of FIG. 15C.

FIG. $17A_1$ illustrates a 3D reference model overlaid on a digital representation of a target object.

FIG. $17A_2$ illustrates a variation of a 3D target coordinate map applied to the target object of FIG. $17A_1$.

FIG. $17A_3$ illustrates the 3D coordinate map of FIG. $17A_2$ without the digital representation of the target object.

FIG. $17A_4$ illustrates a variation of a lattice structure created from the 3D target coordinate map of FIG. $17A_3$.

FIG. $17A_5$ illustrates a variation of a 3D reference model created from the lattice structure of FIG. $17A_4$.

FIG. $17B_1$ illustrates a 3D reference model overlaid on a digital representation of a target object.

FIG. $17B_2$ illustrates a variation of a 3D target coordinate map applied to the target object of FIG. $17B_1$.

FIG. $17B_3$ illustrates the 3D coordinate map of FIG. $17B_2$ without the digital representation of the target object.

FIG. $17B_4$ illustrates a variation of a lattice structure created from the 3D target coordinate map of FIG. $17B_3$.

FIG. $17B_5$ illustrates a variation of a 3D reference model created from the lattice structure of FIG. $17B_4$.

FIG. $17C_1$ illustrates a 3D reference model overlaid on a digital representation of a target object.

FIG. $17C_2$ illustrates a variation of a 3D target coordinate map applied to the target object of FIG. $17C_1$.

FIG. $17C_3$ illustrates the 3D coordinate map of FIG. $17C_2$ without the digital representation of the target object.

FIG. $17C_4$ illustrates a variation of a lattice structure created from the 3D target coordinate map of FIG. $17C_3$.

FIG. $17C_5$ illustrates a variation of a 3D reference model created from the lattice structure of FIG. $17C_4$.

Figure 18A:
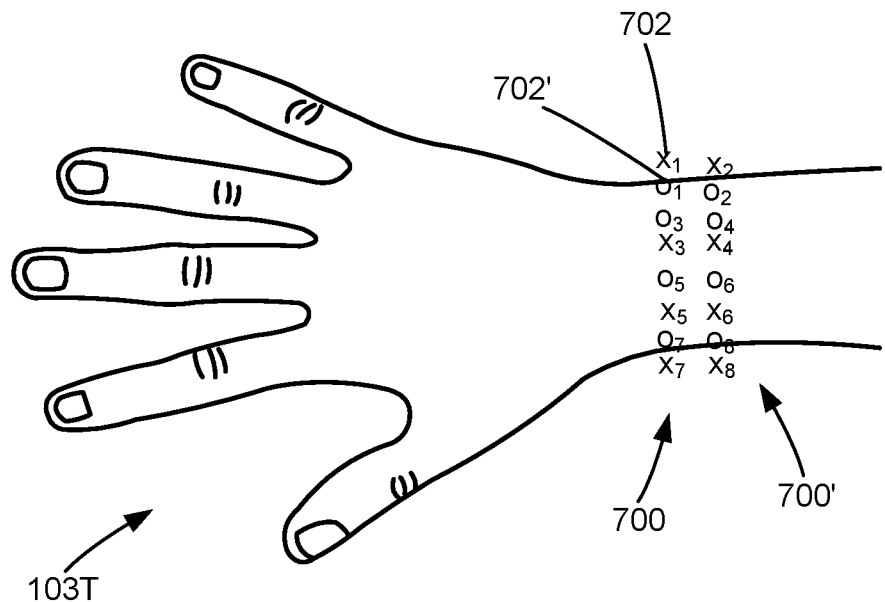

FIG. 18A illustrates variation of the relative positions of a 3D reference coordinate map and a 3D target coordinate map applied to a target object.

Figure 18B:
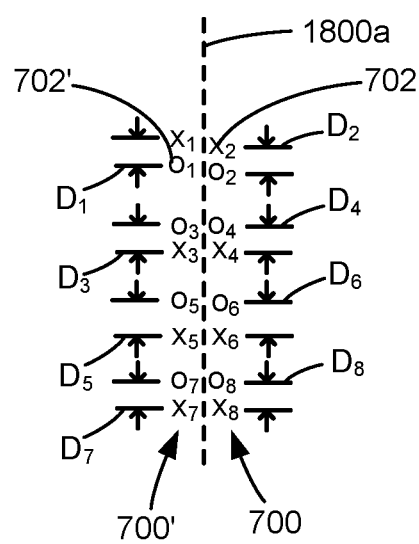

FIG. 18B illustrates the coordinate maps of FIG. 18A without the digital representation of the target object.

Figure 18C:
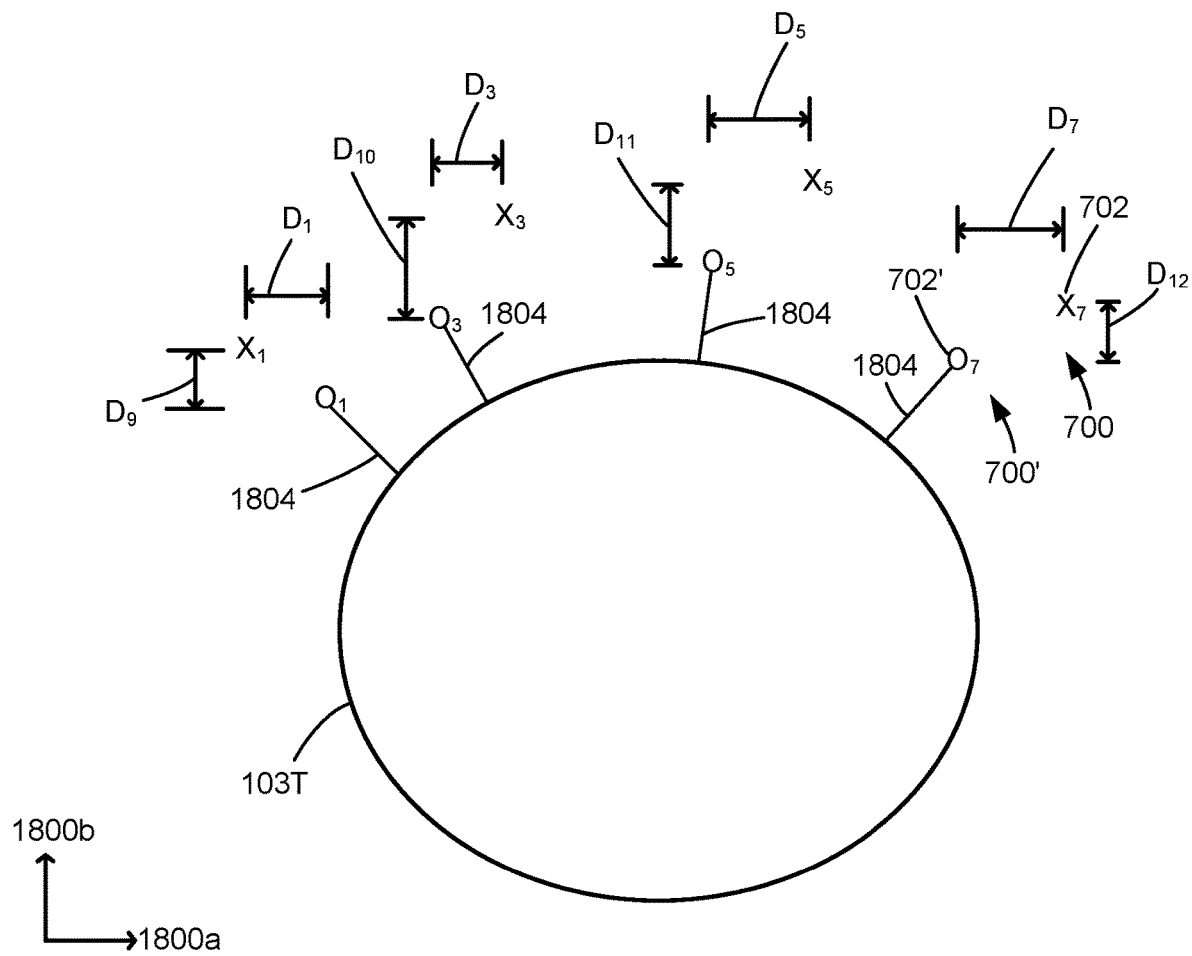

FIG. 18C illustrates a side view of FIG. 18B with a digital representation of the target object of FIG. 18A.

Figure 19:
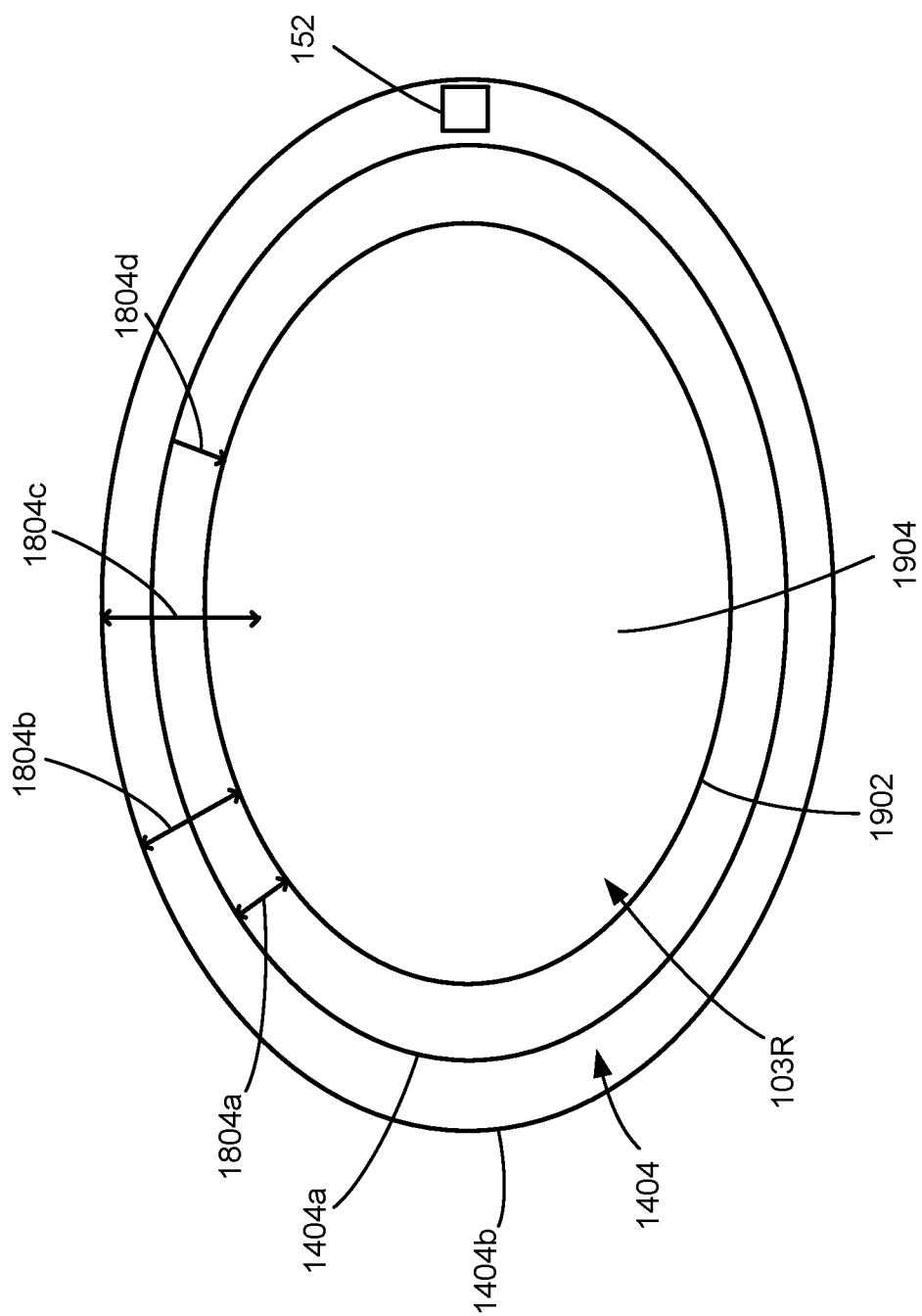

FIG. 19 illustrates variations of fit accuracy parameters.

FIG. $20A_1$ illustrates a variation of a back view of a variation of a digital representation of a reference object.

FIG. $20A_2$ illustrates a variation of a 3D reference coordinate map applied to the digital representation of the reference object of FIG. $20A_1$.

FIG. $20A_3$ illustrates a variation of a 3D reference model lattice applied to the digital representation of the reference object of FIG. $20A_1$.

FIG. $20A_4$ illustrates a variation of a back view of a variation of a digital representation of a target object.

FIG. $20A_5$ illustrates a variation of a 3D target model applied to the digital representation of the target object.

FIG. $20A_6$ illustrates a variation of an adjusted 3D target model applied to the digital representation of the target object.

FIG. $20B_1$ illustrates a variation of a front view of a variation of a digital representation of a reference object.

FIG. $20B_2$ illustrates a variation of a 3D reference coordinate map applied to the digital representation of the reference object of FIG. $20B_1$.

FIG. $20B_3$ illustrates a variation of a 3D reference model lattice applied to the digital representation of the reference object of FIG. $20B_1$.

FIG. $20B_4$ illustrates a variation of a front view of a variation of a digital representation of a target object.

FIG. $20B_5$ illustrates a variation of a 3D target model applied to the digital representation of the target object.

FIG. $20B_6$ illustrates a variation of an adjusted 3D target model applied to the digital representation of the target object.

FIG. $20C_1$ illustrates a variation of a side view of a variation of a digital representation of a reference object.

FIG. $20C_2$ illustrates a variation of a 3D reference coordinate map applied to the digital representation of the reference object of FIG. $20C_1$.

FIG. $20C_3$ illustrates a variation of a 3D reference model lattice applied to the digital representation of the reference object of FIG. $20C_1$.

FIG. $20C_4$ illustrates a variation of a side view of a variation of a digital representation of a target object.

FIG. $20C_{4X}$ illustrates a variation of an x-ray image of the target object applied to the digital representation of the target object of FIG. $20C_4$.

FIG. $20C_5$ illustrates a variation of a 3D target model applied to the digital representation of the target object.

FIG. $20C_{5X}$ illustrates a variation of a 3D target model applied to the x-ray image of FIG. $20C_{4X}$.

FIG. $20C_6$ illustrates a variation of an adjusted 3D target model applied to the digital representation of the target object.

FIG. $20C_{6X}$ illustrates a variation of an adjusted 3D target model applied to the x-ray image of FIG. $20C_{6X}$.

Figure 21:
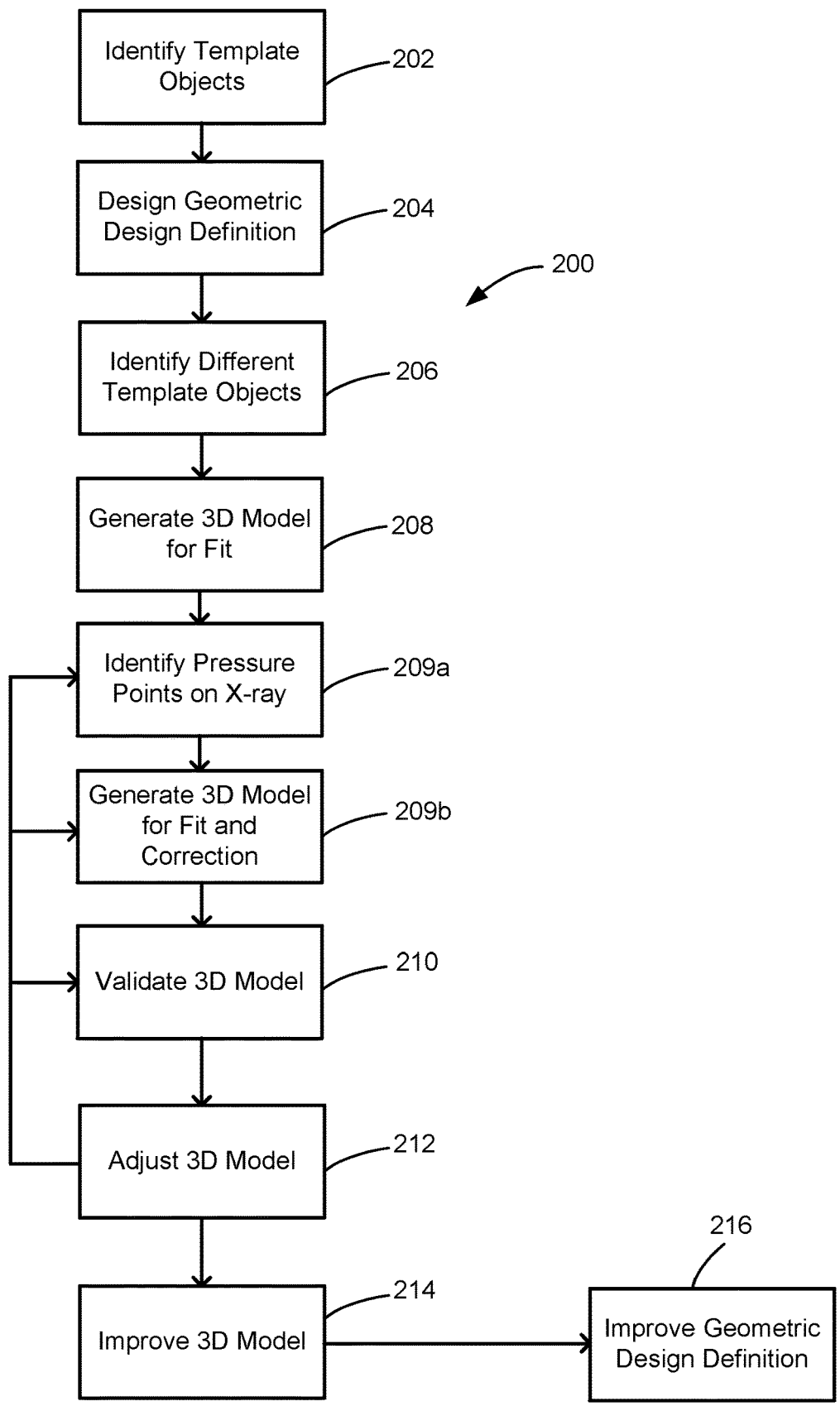

FIG. 21 illustrates a variation of a method undertaken by the system.

DETAILED DESCRIPTION

Overview

Systems and methods of 3D modeling are disclosed. For example, systems and methods are disclosed for modeling structures (also referred to as devices and manufactured 3D models) in 2D or 3D space. The structures can include, for example, orthoses, assistive devices, prostheses, implants, non-medical devices, non-medical structures, or any combination thereof. The orthoses (also referred to as orthopedic devices) can include devices and/or components that are configured to provide support to and/or correct alignment of a portion of a subject's body. For example, the orthopedic devices can include joint braces (e.g., for wrists, ankles, knees, elbows, sacroiliac joints), back braces (e.g., scoliosis braces), implants (e.g., rods, screws, pins, plates for bones, artificial discs), external fixation devices for internal and external support for bones, replacement joints (e.g., for knees, elbows, hips), splints (e.g., for bones), bone fracture repair components (e.g., rods, screws, plates), or any combination thereof. The assistive devices can include, for example, canes, crutches, walkers, wheelchairs (e.g., for subject's with cerebral palsy), or any combination thereof. The prostheses (also referred to as prosthetic devices) can include, for example, limb prostheses (e.g., arm prostheses, leg prostheses), ocular prostheses, extremity prostheses (e.g., hands, fingers, feet, toes), breast prostheses, face prostheses (e.g., nose prostheses), or any combination thereof. The implants can include medical and/or non-medical implants. For example, the medical implants can include implantable devices such as stents, vascular connectors (e.g., anastomotic connectors), artificial heart valves, artificial organs (e.g., hearts), spinal cages, or any combination thereof. Non-medical implants can include, for example, cosmetic implants. Non-medical structures can include fashion products such as clothing (e.g., dresses, pants, shirts), hats, and gloves. Non-medical products can include, for example, floor tiles, engine components (e.g., gears), building structures (e.g., stairs, beams), eating utensils, beverage cozies, or any combination thereof.

The systems and methods disclosed can include acquiring data, creating digital models, manufacturing the digitally created models, or any combination thereof. For example, data can be acquired with one or more data acquisition devices (e.g., imaging devices, sensors, computing devices, digital hand drawings, or any other image capturing technique). For example, the imaging devices can include one or multiple scanners, cameras, x-ray devices, magnetic resonance image (MRI) systems, ultrasound systems, ultrasonographic systems, computerized tomography (CT) systems, or any combination thereof. The sensors can include one or more usage sensors such as accelerometers, breathing monitors, heart rate monitors, blood pressure sensors, moisture sensors, temperature sensors, pressure sensors, displacement sensors, force sensors, or any combination thereof.

The systems and methods disclosed can include acquiring one or more reference objects (also referred to as template objects, generic template objects, and initial objects) and/or one or more target objects (also referred to as specific template objects, unique template objects and different template objects), for example, using one or more data acquisition devices. The target objects can be topologically isomorphic to the reference objects. The reference and target objects can have the same or similar structure as one another (e.g., the same or similar body part). For example, when the reference object is a wrist, the target object can be a wrist or an ankle. As another example, when the reference object is a torso, the target object can be a torso.

The modeling disclosed can include designing 3D models, generating 3D models, adjusting 3D models, validating 3D models, using validated 3D models, or any combination thereof. For example, the modeling disclosed can include designing 3D reference models, generating 3D target models, adjusting 3D target models, validating 3D target models, using validated 3D target models, or any combination thereof.

The 3D models disclosed can be designed to fit one or more reference objects. 3D models that are designed to fit reference objects are referred to as 3D reference models.

The 3D models disclosed can be designed to fit one or more target objects, for example, from data acquired and/or generated from one or more reference objects. The design of 3D models designed to fit one or more target objects can also be based on data acquired and/or generated from the target objects. 3D models that are designed to fit target objects are referred to as 3D target models.

The term 3D model can refer to 3D reference models and/or to 3D target models.

Target objects can be topologically isomorphic to the reference objects that the 3D reference models are designed to fit. For example, the 3D models disclosed can be derived from a single reference object or a set of general digital or physical objects, where each object in a set has the same or similar isomorphic topology to the other objects in the reference object set. A reference object set can include two or more reference objects, for example, from 2 to 10,000 or more reference objects, including every 1 reference object increment within this range or beyond, as well as every 10 reference object range within this range. Reference objects in a reference object set can have homomorphic topologies.

The 3D models disclosed can be created based on visual and/or mathematical data (e.g., measurements) associated with one or more reference and/or target objects. The visual and/or mathematical data can include the digital images of the objects and analyses of the digital images (e.g., measurements and/or quantifications of geometric features of the objects).

The 3D models disclosed can be designed by determining one or more geometric design definitions. The geometric design definitions can define the 3D models. For example, the geometric design definitions can visually (e.g., graphically) and/or non-visually (e.g., mathematically) define the geometric and/or non-geometric relationships between the 3D model and the object that the 3D model is designed to fit.

The geometric design definitions can be created from one or multiple components, for example, fit accuracy parameters, coordinate maps, geometric constructs, or any combination thereof. The components of the geometric design definition can be independent of one another. Additionally or alternatively, one or more of the components of the geometric design definition can be dependent on one or more (e.g., both) of the other components.

The fit accuracy parameters can include parameters that quantify the relationship between one or more reference objects and the 3D reference models that are designed to fit the reference objects. The fit accuracy parameters can include geometric and non-geometric parameters such that the geometric design definition can represent the geometric and non-geometric relationship between the reference objects and the 3D reference models designed to fit the reference objects. For example, the geometric fit accuracy parameters can include maximum and/or minimum dimensions between the 3D reference model and the reference object, relative dimensions of the 3D reference model (e.g., thickness between a first surface and a second surface of the 3D reference model), or any combination thereof. The non-geometric fit accuracy parameters can include, for example, pressure parameters, temperature parameters, moisture parameters, force parameters, flexibility parameters (also referred to as elasticity parameters), rigidity parameters (also referred to as hardness and softness parameters), or any combination thereof.

The coordinate maps can be 2D and/or 3D (more simply referred to throughout as 3D coordinate maps). The 3D coordinate maps can relate the geometry of the reference object to the geometry of the 3D target model. The 3D coordinate map can be determined independent of the fit accuracy parameters. The 3D coordinate map can be dependent on one or more of the fit accuracy parameters. The 3D coordinate map can be applied to the digital representation of the reference object. The geometric design definition can be a function of the 3D coordinate map and/or of the fit accuracy parameters. The geometric definition can be a computable mathematical representation.

The geometric constructs can be the geometric forms (e.g., points, lines, curves, shapes) that make up the 3D reference model.

The modeling disclosed can include generating 3D models using one or more of the determined geometric design definitions, for example, by computing the geometric design definitions. The geometric design definition can be computed for the object that the geometric design definition was created to fit (e.g., the reference object) and/or for another object (e.g., a target object isomorphically the same as the reference object). The 3D target models can be generated by morphing one or more 3D reference models to fit one or more different target objects by computing the geometric design definition with inputs from the target object that the 3D reference model is being morphed to fit. For example, the modeling disclosed can include determining a geometric design definition of a 3D reference model designed to fit a first object (e.g., a reference object) and then generating a 3D target model designed to fit a second object different from the first object (e.g., a target object) by computing the geometric design definition of the 3D reference model. The geometric design definition computation can transform the 3D reference model into a 3D target model, where the generated 3D target model has a geometry that fits the target object. Inputs of the geometric design definition can include, for example, coordinates of the target object and/or data representative of differences (e.g., geometric differences) between the reference and target objects.

The 3D models disclosed can be created completely or at least partly from the geometric design definitions determined from one or more reference objects. The 3D reference models defined by the geometric design definitions can be morphed to fit digital or physical target objects having the same or similar isomorphic topology as the reference object(s) from which the geometric design definition is based, for example, by computing the geometric design definition with parameters associated with the target objects and/or by graphically modifying (via a computer or manually) a visual representation of the 3D reference model to fit the target objects. For example, the geometric design definitions can be morphed to define 3D target models that fit target objects by being computed one or more times. In this way, the geometric design definitions and 3D reference models can be morphed one or more times to fit any target object that is isomorphically the same as the reference object or a set of reference objects.

The 3D models disclosed can be digitally created to fit a target object based on visual and/or mathematical inputs, using, for example, one or more images of the target object, one or more sensed and/or detected features of the target object, one or more measurements of the target object, one or more geometric design definitions of reference objects, one or more images of the reference object, one or more sensed and/or detected features of the reference object, one or more measurements of the reference object, or any combination thereof. For example, the 3D models disclosed can be computationally derived and/or visually derived from data representative of the reference object and/or representative of a structure designed to fit the reference object. Visual derivation can include overlaying (e.g., digitally overlaying) two or more images together, for example, overlaying a 3D reference model computed from a geometric design definition over a digital representation of the target object that the 3D reference model is being modified to fit. One or more parameters of the target object can be mathematical inputs of the geometric design definitions. Additionally or alternatively, one or more sensed and/or detected features in an image overlay can be mathematical inputs of the geometric design definitions. The sensed and/or detected features can include dimensions of the reference and target objects. For example, the systems and methods can identify object boundaries, can identify the differences between reference object boundaries and the target object boundaries, can identify the differences between generated 3D target model boundaries and the target object, or any combination thereof.

Systems and methods for creating 3D target models from data acquired and generated from reference objects are disclosed. Orthoses, prostheses, implants, non-medical devices, and/or non-medical structures can be modeled and/or manufactured with the systems and methods disclosed. The 3D models disclosed can be generated to form fit (also referred to as closely fit, e.g., a fit that tightly follows the contours of the reference object) a reference object, to fit an interior (e.g., an interior layer) of a reference object, to fit an exterior (e.g., an exterior layer) of a reference object, or any combination thereof. Additionally or alternatively, the 3D models disclosed can be generated to form fit (also referred to as closely fit, e.g., a fit that tightly follows the contours of the reference object) a target object, to fit an interior (e.g., an interior layer) of a target object, to fit an exterior (e.g., an exterior layer) of a target object, or any combination thereof. The 3D models disclosed can be generated to fit (e.g., form fit, interior fit, exterior fit) target objects with or without generating 3D models to fit the one or more reference objects from which the 3D model of the target object is based.

The modeling disclosed can include validating 3D target models. For example, the 3D target models can be validated against the fit accuracy parameters and/or against the target object (e.g., by digitally overlaying the generated 3D target model on the target object). Validated 3D models can be saved in a database. The validated 3D models can be manufactured for the target object. Non-validated 3D models can be adjusted to better fit the target object and then generated again. The process can repeat until the generated 3D model fits the target object, for example, according to the fit accuracy parameters.

Systems and methods are disclosed for creating geometric design definitions of reference objects, generating 3D models that fit reference objects, generating 3D models that fit topologically isomorphic target objects, improving the fit accuracy of the generated 3D models with the target objects, or any combination thereof. For example, the systems and methods disclosed can include one or more of the following processes, in no particular order, in the order listed, or in any combination: identifying one or more (e.g., a set of) reference objects; if a reference object is a physical object, extracting the digital representation of the physical reference object; determining the fit accuracy parameters (also referred to as fit accuracy requirements) for a 3D reference model; creating a coordinate map (e.g., 2D or 3D coordinate map) relating the geometry of the reference objects to the geometry of a 3D reference; creating a geometric definition for the design of a 3D reference model that fits the reference object, for example, using the coordinate map; generating a 3D target model that fits a target object having the same or similar isomorphic topology as the reference object, for example, using the geometric design definition of the 3D reference model and/or the coordinate map; validating the fit of a digital rendering of the generated 3D target model against a digital rendering of the target objects; adjusting the geometry of the generated 3D target model to better fit the target object, improving the geometry of the generated 3D target model to better fit the target object.

Systems and methods are disclosed for iteratively improving the geometric design definition of the 3D models, for example, to improve the fit of the 3D models generated for the target objects. The geometric design definitions can be iteratively improved, for example, by adjusting the 3D coordinate map and/or the geometric design definition. The geometric design definitions can be improved using computational and/or visual techniques. As described above, the geometric design definitions can define 3D reference models.

The geometric design definitions can be represented as computational data models. For example, the geometric design definitions can be computational functions having one or multiple inputs that can be iteratively optimized (also referred to as adjusted, morphed and changed). Systems and methods are disclosed that can modify the geometric design definitions of the 3D models to improve the fit of 3D models generated to fit target objects. For example, the systems and methods disclosed can use machine learning (e.g., online machine learning) to modify the geometric design definitions. Using machine learning, the geometric design definition can learn (also referred to as adapt) in response to, for example, outputs from statistical, probabilistic and/or deep learning algorithms. In such variations, the geometric design definitions can be adapted for better fit accuracy with reference objects, advantageously reducing the computational burden and/or time to generate the 3D models morphed to fit the target objects.

Systems and methods are disclosed for creating and iteratively improving geometric design definitions for 3D models of reference objects that can morph to fit a set of topological isomorphic target objects based on visual and/or mathematical inputs.

Systems and methods are disclosed for designing, generating, validating, adjusting, and/or improving 3D models that can fit target objects, for example, target objects that are topologically isomorphic to the reference objects.

The reference and target objects can be digitally represented in various formats including, for example, 2D images (e.g., photographs) of a physical object, 3D acquisitions (e.g., scans) of a physical object, mathematical descriptions of the dimensions of a physical object, 2D digital objects, 3D digital objects, 2D renderings of digital 3D objects, mathematical descriptions of the dimensions of a digital object, or any combination thereof. The 3D models disclosed can be represented in, for example, STereoLithography File Format (STL), Object File Format (OBJ), Polygon File Format (PLY), mathematical descriptions of the 3D geometry of the model, or any combination thereof.

Systems and methods are disclosed for creating 3D models that can be used in physical and digital environments. The 3D models can be manufactured as physical structures and/or can be used in digital spaces such as games, animated movies, virtual reality applications, augmented reality applications, or any combination thereof. The systems and methods disclosed can be used for mass-customization of structures.

Systems and methods are disclosed for manufacturing 3D models.

Systems and methods are disclosed for monitoring the usage of manufactured 3D models. The systems and methods disclosed can include acquiring data of structure usage, for example, when the structures are being used (e.g., when worn, when carried, when implanted). Structure usage data can be acquired using one or more usage sensors. The usage sensors can be attached to or integrated with the structures. The acquired sensor data can be used to improve the design of the structure, for example, using one or more learning methods. For example, the acquired sensor data can be processed by one or more learning modules (e.g., machine learning) to improve the geometric design definition.

Systems & Structures

FIG. 1 illustrates a schematic of a variation of a 3D modeling system 100. The system 100 can include a data acquisition device 102, a modeling unit 104, a manufacturing unit 106, or any combination thereof. The data acquisition device 102 can be in wired or wireless communication with the modeling unit 104. The modeling unit 104 can be in wired or wireless communication with the manufacturing unit 106. The modeling unit 104 can receive data from one or more data acquisition devices 102. The data acquisition devices 102 can be used to capture (also referred to as image, digitally image, or any combination thereof) reference and target objects 103R, 103T. The data acquisition devices 102 can be, for example, sensors, imaging devices, computing devices, digital hand drawings, or any other image capturing device. The imaging devices can be, for example, scanners, cameras, x-ray devices, MRI systems, ultrasound systems, ultrasonographic systems, CT systems, or any combination thereof.

The same or different data acquisition device 102 can be used to image each of the reference and/or target objects 103R, 103T. The data acquisition device 102 can be used to create an image or digital image of the entire body and/or one or more parts of the body, for example, the entire body, limbs or portions thereof, joints, the torso, or any combination thereof. The target objects 103T can be topologically isomorphic to a reference object 103R.

The modeling unit 104 can process data received and/or retrieved from the data acquisition device 102. The modeling unit 104 can be local or remote relative to the data acquisition device 102. For example, the modeling unit 104 can be on or be part of a server such as a cloud server, a cluster server, and/or a storage server. The modeling unit 104 can have a processor unit configured to process the images received from the data acquisition devices 102.

The manufacturing unit 106 can process data received and/or retrieved from the modeling unit 104. The manufacturing unit 106 can be local or remote relative to the modeling unit 104. The manufacturing unit 106 can be connected to the modeling unit 104 through a network. The manufacturing unit 106 can manufacture structures using the 2D or 3D models disclosed. The manufacturing unit 106 can manufacture the 3D reference models disclosed, the 3D target models disclosed, or any combination.

The manufacturing unit 106 can manufacture the disclosed models, for example, using 3D printing, computer numerical control (CNC) routers, industrial robots, textile machines, or any combination thereof. The 3D printing techniques used can include, for example, stereolithography (SLA), digital light processing (DLP), fused deposition modeling (FDM), selective laser sintering (SLS), selective laser melting (SLM), electronic beam melting (EBM), laminated object manufacturing (LOM), or any combination thereof. The CNC routers used can include, for example, plasma cutters, milling machines, lathes, laser cutters, mill-turn multiaxis machines, surface grinders, tool & cutter grinders (e.g. Walter, Anka), multi-axis machines, specialty machines, or any combination thereof. The industrial robots used can include, for example, cartesian coordinate robots (also called linear robots), SCARA robots (selective compliance assembly robot arm and selective compliance articulated robot arm), 6-axis robots, redundant robots, dual-arm robots, welding robots, or any combination thereof. The textile machines used can include, for example, weaving machines, knitting machines, garment machines, cutting machines, sewing machines, or any combination thereof.

Figure 1A:
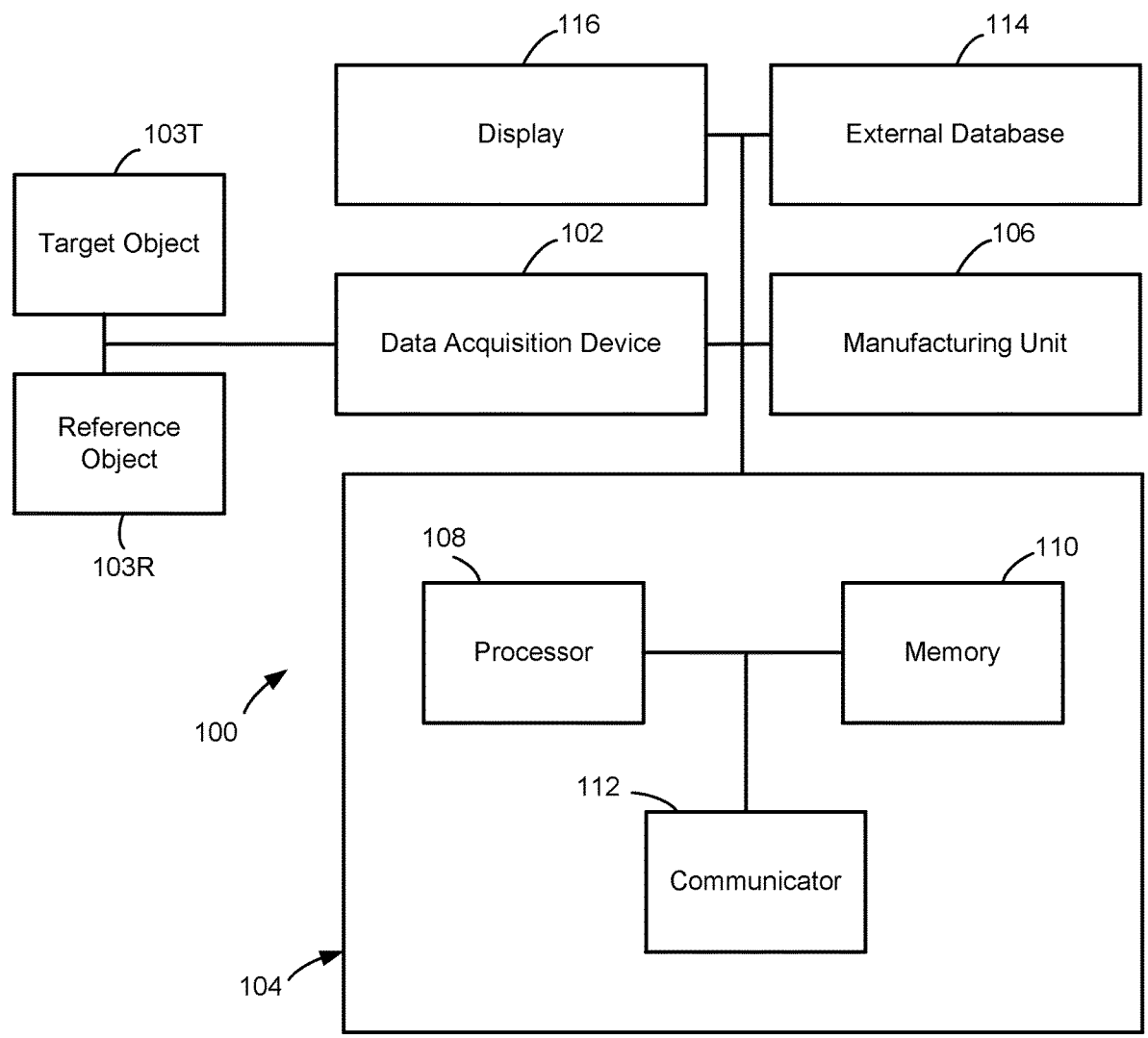
FIG. 1A illustrates a variation of a schematic of a 3D modeling system.

FIG. 1A further illustrates that the modeling unit 104 can have one or multiple processing units 108, memory units 110, communication units 112, or any combination thereof. The processing unit 108 can be coupled to the memory and communication units 110, 112 through, for example, high-speed buses.

The processing units 108 can include one or more central processing units (CPUs), graphical processing units (GPUs), application-specific integrated circuits (ASICs), field-programmable gate arrays (FPGAs), or any combination thereof. The processing units 108 can be programmable processors. The processing units 108 can execute software stored in the memory units 110 to execute the methods, instructions, and/or algorithms described herein. The processing units 108 can be an embedded processor, a processor core, a microprocessor, a logic circuit, a hardware finite state machine (FSM), a digital signal processor (DSP), or any combination thereof. As a more specific example, the processing units 108 can be a 32-bit or a 64-bit processor.

The memory units 110 can store software, data, logs, or any combination thereof. The memory units 110 can store data received from the data acquisition devices 102, as well as the output from the processing units 108. The memory units 110 can be internal memory of the modeling unit 104 as shown in FIG. 1A, or can be external memory, such as a memory residing on a storage node, a cloud server, and/or a storage server. The memory units 110 can be a volatile memory or a non-volatile memory. For example, the memory units 110 can be a non-volatile storage medium such as non-volatile random access memory (NVRAM), flash memory, disk storage, or a volatile storage such as static random access memory (SRAM). The memory units 108 can be the main storage unit for the modeling unit 104.

The communication unit 112 can be a transceiver. The communication unit 112 can include one or more wired or wireless communication interfaces. The communication unit 112 can be a network interface card of the modeling unit 104. The communication unit 112 can be a wireless modem or a wired modem, for example, a WiFi modem, a 3G modem, a 4G modem, an LTE modem. Additionally or alternatively, the communication unit 112 can be a Bluetooth™ component, a radio receiver, an antenna, or any combination thereof. For example, the communication unit 112 can be a server communication unit. The modeling unit 104 can transmit and/or receive data packets and/or messages using the communication unit 112. The communication unit 112 can connect to or communicatively couple with one or more wireless signal transceivers and/or networks.

FIG. 1A also illustrates that the system 100 can have one or more external databases 114. The external data bases 114 can be configured to store data associated with the reference and/or target objects 103R, 103T. The external databases 114 can be separate from, alternative to, and/or additional to the memory units 110. Additionally or alternatively, the external database 114 can be integrated or otherwise combined with the memory units 110. The external databases 114 can be on or be part of a server, for example, a cloud server, and/or a storage server.

The memory 110 and/or the external database 114 can be configured to store data associated with reference objects 103R and/or with target objects 103T. The target object data can correspond to patient-specific data. The reference object data can correspond to patient-specific data. The reference object data can correspond to non-patient specific data. For example, the reference object 103R can correspond to an image of a first person and the target object 103T can correspond to an image of a second person different from the first person. The data associated with the target object can also be used as reference object data, for example, to modify a geometric design definition and/or to create a new geometric design definition.

FIG. 1A also illustrates that the system 100 can have one or more displays 116. The displays 116 can display data acquisition results, modeling results, or any combination thereof. The displays 116 can be integrated with the device or system having the modeling unit 104 and/or can be part of a standalone device in wired or wireless communication with the modeling unit 104. For example, the display 116 can be part of a computer, a smartphone, a tablet, a laptop, a smartwatch, or any combination thereof. The device having the display 116 can be in communication with the data acquisition devices 102, one or more other devices, the cloud, and/or one or more networks.

Executable code can be installed on memory (e.g., memory 110) of the device having the display 116. When the executable code is executed by the system 100, the system 100 can perform the instructions, processes, methods, and operations disclosed and contemplated herein, such that the system 100 can analyze data acquisition results and perform the methods disclosed herein, for example, determining geometric design definitions, generating 3D models, adjusting 3D models, improving 3D models, or any combination thereof. For example, executable code can be downloaded onto a computer configured to carry out the various functions of the modeling unit 104. Additionally or alternatively, executable code can be located on the cloud, for example, on a server. A device (e.g., a smartphone) can query the server to run the executable code on the server to carry out the instructions, processes, methods, and operations disclosed and contemplated herein.

Additionally or alternatively, the modeling unit 104 can comprise downloadable executable code that utilizes existing processing, memory, and data storage features of a device and/or the cloud.

Figure 1B:
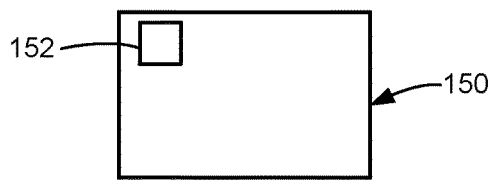
FIG. 1B illustrates a variation of a schematic of a manufactured 3D model.

FIG. 1B illustrates that a manufactured 3D model 150 can have one or multiple sensors 152, for example, 1 to 25 sensors 152, 1 to 50 sensors 152, or 1 to 100 sensors 152, including every 1 sensor increment within these ranges. The sensors 152 can be attached to and/or integrated with the structure 150. The sensors 152 can be flexible or rigid. The sensors 152 can be attached to one or multiple flexible circuits (e.g., flexible PCB) that can be attached or integrated with the structure 150, for example, 1 to 100 flexible circuits. The sensors 152 can comprise a sensor array. The sensor array can be rigid or flexible. The sensors 152 can be on an inner surface, on an outer surface, in an interior, and/or along one or more edges of the structure 150. Data from the sensors 152 and/or sensor arrays can be communicated wired or wirelessly, for example, to one or more controllers, networks, servers, modeling units 104, or any combination thereof.

The sensors 152 can include, for example, one or more accelerometers, breathing monitors, heart rate monitors, blood pressure sensors, moisture sensors, temperature sensors, pressure sensors, displacement sensors, force sensors, or any combination thereof. The sensors 152 can be usage sensors configured to acquire data when the manufactured 3D models are being used (e.g., when worn, when carried, when implanted). Additionally or alternatively, the sensors can be sensors configured to acquire data when the manufactured 3D models are not being used. Data from the sensors can be used to help improve the design of the structure 150, for example, to improve the structure's function and/or to increase a user's comfort when using the structure.

The one or more accelerometers 152 can monitor movement of the user (not shown) and/or structure 150. The accelerometers can be configured to check or monitor the user's mobility (e.g., range of motion, changes in position, changes in movement) while using the structure. Accelerometer data can be used to improve the geometric design definition so that the mobility associated with subsequent structures can be improved (e.g., so that a user's range of motion is increased, so that user movement is easier, so that the structure provides less resistance to user movement).

The one or more breathing monitors 152 can monitor breathing of a user while using the structure 150. The breathing data acquired can be analyzed to determine breathing patterns, changes in breathing patterns, breathing rates, and/or changes in breathing rates of the user. Breathing data can be used to improve the geometric design definition so that the breathing of users associated with subsequent structures can be improved or made more comfortable.

The one or more heart rate sensors 152 can monitor a user's heart rate and changes in heart rate while using the structure 150. The heart rate data acquired can be analyzed to determine when the structure is being used, the length of use, and whether the use is periodic (e.g., on and off wear) or continuous (e.g., all day, all night). Heart rate data can be used to improve the geometric design definition by optimizing the heart rate sensor placement on the structure 150 such that a user's heart rate can be reliably monitored.

The one or more blood pressure monitors 152 can monitor a user's blood pressure and changes in blood pressure while using the structure 150. The blood pressure data acquired can be analyzed to determine when the structure is being used, the length of use, and whether the use is periodic (e.g., on and off wear) or continuous (e.g., all day, all night). Blood pressure data can be used to improve the geometric design definition by optimizing the blood pressure sensor placement on the structure 150 such that a user's blood pressure can be reliably monitored.

The one or more moisture sensors 152 (also referred to as humidity sensors) can monitor sweating from the user. The moisture data acquired can be analyzed to determine the quantity a user is sweating, the user's sweat rate, and/or the structure's moisture content when the structure is being used. Moisture data can be used to improve the geometric design definition so that optimal sweating can be achieved (e.g., more or less sweating), and/or so that the humidity inside the structure 150 or between a user and a user contact surface of the structure 150 can be minimized or lessened.

The moisture sensors 152 can be sweat sensors. The moisture sensors can measure moisture volume, for example, the volume of moisture absorbed by the sensor, the volume of moisture absorbed by the structure adjacent the sensor, the volume of moisture that passes through the sensor, or any combination thereof.

The one or more temperature sensors 152 (also referred to as thermal sensors and heat sensors) can monitor a user's temperature and changes in temperature while using the structure 150. Additionally or alternatively, the one or more temperature sensors 152 can monitor the environment temperature and changes in the environment temperature. Temperature data can be used to improve the geometric design definition so that the structure 150 has less or more of an effect on a user's temperature, and/or so that the temperature inside the structure 150 or between a user and a user contact surface of the structure 150 can be minimized or lessened (e.g., so that the optimal temperature can be achieved between the structure 150 and the user).

The one or more pressure sensors 152 can monitor the pressure applied by the structure to the user. The pressure data acquired can be analyzed to determine the pressures that the structure is applying to the user. Pressure data can be used to improve the geometric design definition by ensuring that the desired pressures are achieved against the user at the pressure sensor contact points.

The one or more force sensors 152 can monitor the internal and external forces applied to the structure 150. The force data can be analyzed to determine the internal and/or external forces applied to the structure 150. Force data can be used to improve the geometric design definition by ensuring that the structure 150 is tolerant of internal and external impacts to the structure 150. External forces can be applied to the structure 150 from the environment such as impact forces from other objects. Internal forces can be applied to the structure from the user. Additionally or alternatively, internal forces can correspond to tensile and/or compressive forces that the structure 150 experiences.

The location of the sensors can be adjusted, or any component of the geometric design definition can be adjusted in response to data acquired and/or analyzed from one or more sensors 152.

Methods

Figure 2:
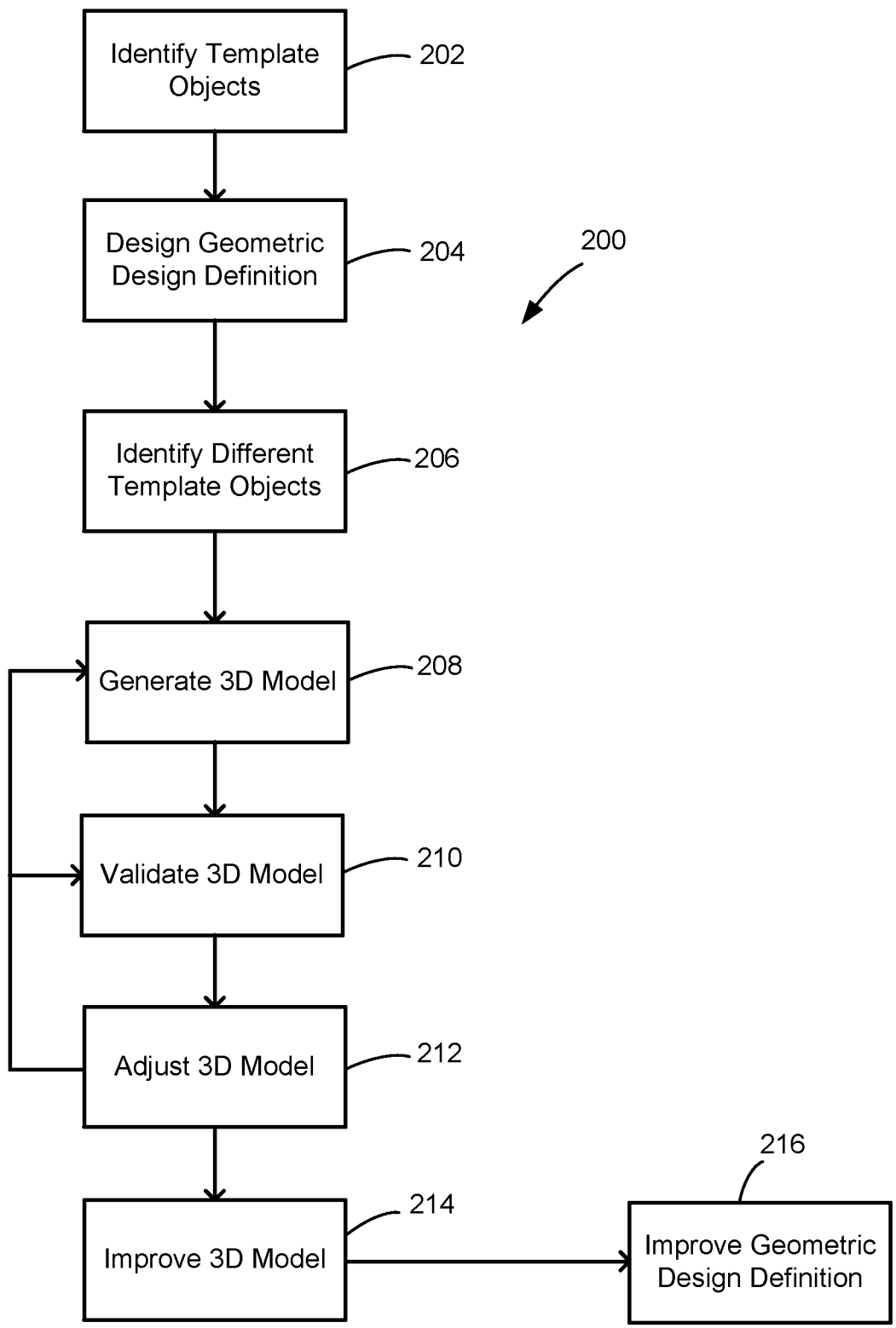
FIG. 2 illustrates a variation of a method undertaken by the system.

FIG. 2 illustrates a variation of a process 200 that is implementable using and/or performable by the system 100. The method 200 can involve identifying (e.g., sensing, imaging) objects, creating geometric design definitions, designing 3D models, modifying (e.g., optimizing) 3D models, modifying (e.g., improving) geometric design definitions, or any combination thereof.

For example, FIG. 2 illustrates that the method 200 can involve identifying (also referred to as acquiring) one or more reference objects in operation 202. Operation 202 can include acquiring reference objects using, for example, a data acquisition device 102. Operation 202 can include identifying physical reference objects and/or digital reference objects using, for example, a data acquisition device 102. The identifying step 202 can involve sensing and/or imaging physical reference objects. The identifying step 202 can involve receiving data (e.g., images) of an object in an electronic format (e.g., digital pictures) and/or in a physical format (e.g., physical pictures). Physical images can be converted to digital images. For example, operation 202 can include extracting one or more digital representations of physical reference objects. The identifying step 202 can acquire data (e.g., images) of reference objects. The data (e.g., images) can be configured to be visually displayed, for example, as a digital representation.

The reference objects can be animate and/or inanimate objects. Animate objects can include any living organism, for example, people and/or animals. For example, operation 202 can include identifying a person's and/or animal's body, for example, the entire body, regions of the body (e.g., the torso, upper body, lower body), limbs (e.g., arms, legs), extremities (e.g., hands, feet), joints (e.g., knuckles, wrists, elbows, shoulders, ankles, knees, hips, sacroiliac joint, vertebral joints, rib joints, temporomandibular joints), or any combination thereof. Inanimate objects can include nonliving objects such as machines, robots, household items (e.g., furniture) and office equipment (e.g., chairs, desks). Animate and inanimate objects can be acquired (e.g., sensed, imaged) separately or together. The system 100 can identify animate and/or inanimate objects separately and/or simultaneously.

Operation 202 can generate data representative of the reference objects acquired. For example, operation 202 can involve mapping the boundaries and/or surfaces of the reference objects, determining the dimensions of the reference objects, determining skin thicknesses, determining tissue percentages (e.g., % muscle, % fat), determining bone density, or any combination thereof.

Operation 202 can identify one or multiple reference objects, for example, 1 to 1,000 or more reference objects, including every 1 reference object increment within this range or beyond (e.g., less than 10,000 reference objections, 10,000 or more reference objections). Multiple reference objects can be identified in operation 202 to create a set of reference objects. A set of reference objects can be initially created and/or a set of reference objects can be created over time (e.g., as each individual reference objects is acquired by the system 100 to generate geometric design definitions). The method 200 can create one or multiple sets of reference objects, for example, for each body part, for each body region, for each body, or any combination thereof. Each set of reference objects can have a homomorphic topology. For example, each reference object in a set can have the same or similar isomorphic topology to the other objects in the set. A set of reference objects can include the same or different objects. For example, a set of 5 reference objects can include digital acquisitions of 5 different animate and/or inanimate objects, digital acquisitions of the same animate object separated by a time interval (e.g., 6 months to 5 years, including every 1 month increment within this range, and/or any time period less than 6 months), or any combination thereof.

Operation 202 can identify one or multiple reference objects in a physical and/or digital representation of a data acquisition of a subject, where the subject can be an animate and/or inanimate object (e.g., a person or an animal). The reference objects can be identified by a person, by computer vision, by an analysis of the data acquisition, or any combination thereof. For example, operation 202 can identify one or multiple target objects in a single image or group of images of a single subject (e.g., a person or an animal), for example, an image or group of images of an entire body of a subject. For example, operation 202 can identify 1 to 10 or more reference objects in a subject's images, including every 1 reference object increment within this range or beyond (e.g., less than 15 reference objects, 15 or more reference objects). Where a digital representation of a subject comprises a torso, for example, the reference objects can be the vertebrae, ribs, the connections between the vertebrae and the ribs, the outer surface of the torso, or any combination thereof. Where a digital representation of a subject comprises a left arm, for example, the reference objects can be one or more of the fingers, the hand, the wrist, the forearm, or any combination thereof. Multiple reference objects can be identified in operation 202 to generate multiple geometric design definitions which can define, for example, a set of 3D reference models. The multiple 3D reference models can be independent from one another, or can be configured to interact with one another, for example, such that the multiple geometric design definitions can be adjusted individually, in two or more groups, or collectively. This can be useful where the 3D model (e.g., a brace) is configured to interact with multiple portions of the body. For example, subjects with cerebral palsy may require two or more separate 3D models to accommodate different portions of their body. The 3D models can be configured to be attached to one another, integrated with one another, or be standalone models.

Operation 202 can identify the reference objects with one or multiple views, for example, 1 to 10 views, including every 1 view increment within this range. For example, operation 202 can involve acquiring reference objects with first, second, third, and fourth views, or any combination thereof. The first, second, third, and forth views can be, for example, front, back, first side (e.g., left side), second side (e.g., right side) views of the reference object, or any combination thereof. The foreground and/or background can be distinguished from the reference object. The foreground and/or background can be filtered out of the image, ignored, or used for one or more reference points.

The reference object can be a combination of multiple reference objects (different from a series of reference objects) such that a single reference object can be representative of multiple reference objects acquired from multiple subjects (e.g., animate and/or inanimate objects). Data associated with the reference objects can be determined in operation 202, for example, when the reference object is acquired or at any point thereafter. For example, for people and animals, data such as the age, gender, body weight, body shape, body dimensions (e.g., height), body part dimensions (e.g., wrist dimensions, limb length), body mass index (BMI), reference object dimensions, or any combination thereof, associated with the reference object and/or associated with the subject of the reference object can be determined. For example, for inanimate objects, data such as dimensions and geometric features of the inanimate object can be determined.

Reference objects that incorporate data (e.g., image data) from two or more reference objects are referred to as integrated reference objects. Integrated reference objects can be created using one or more learning methods. For example, integrated reference objects can be created using machine learning (e.g., online machine learning). The integrated reference objects can be normalized using the learning methods to correspond to specific values and/or ranges in age, gender (e.g., male and female torsos can be separately classified), body weight, body shape, body dimensions (e.g., height), body part dimensions (e.g., wrist dimensions, limb length), body mass index (BMI), reference object dimensions, or any combination thereof (referred to collectively as identifying characteristics). Such normalizations can correspond to match criteria that can be used to match target objects to integrated reference objects. For example, the match criteria can be used to optimally pair target and integrated objects together such that target objects can be paired with the integrated reference object that is most similar to the target object for which the 3D target model is to be generated. Each reference object (including integrated and non-integrated reference objects) can be classified using one or more of these identifying characteristics. The reference objects and their associated classifications can be stored in a reference object database that can be used as a general pool of objects from which to create geometric design definitions.

Additionally or alternatively, integrated reference objects can be created after a target object is identified, for example, based on the geometric (e.g., dimensions, shape) and/or non-geometric properties (e.g., weight, BMI) of the target object and/or subject. Once these features of the target object are determined, the learning methods can combine multiple reference objects together that have features similar to that of the target object so that the generation of the 3D target model can be less intensive than using a non-integrated reference object for generating the 3D target model. Combining multiple reference objects together can include combining portions of one or more of the reference objects together. Each reference object can be partially or entirely incorporated into an integrated reference object.

Integrated reference objects can be desirable to create to increase the accuracy of the computation of the geometric design definition that generates the 3D target model. The use of an integrated reference object can also allow 3D target models to be more quickly generated than if a single reference object were used, for example, since the integrated reference object is a more optimized starting point than a standalone reference object. Integrated reference objects can be normalized to correspond to male and/or female subjects. Integrated reference objects can be normalized to correspond to gender neutral objects. Operation 202 can use an integrated reference object when the target object is more similar to an integrated reference object than a reference object that has not been normalized using one or more learning methods. The method 200 can involve first determining a target object and then determining which reference object to use. The reference object can be integrated or non-integrated. The integrated reference object can be selected from a database and/or can be created based on the target object acquired. The term reference object used in this disclosure can refer to non-integrated reference objects and/or integrated reference objects.

FIG. 2 further illustrates that the method 200 can involve creating (also referred to as designing, generating and constructing) a geometric design definition of a 3D reference model in operation 204. The 3D reference model can be designed to fit one or more of the reference objects acquired, for example, in operation 202. The geometric design definition can define the geometry of the 3D reference model design, for example, with a mathematical description, a mathematical formula, a non-mathematical description, or any combination thereof. The geometric design definition can also include non-geometric properties of the 3D reference model, such as, for example, pressures associated with one or more contact points between the 3D reference model and the reference object. As described above, the geometric design definition can include multiple components, for example, fit accuracy parameters, 3D coordinate maps, and geometric constructs. A geometric design definition can be created from non-integrated and integrated reference objects. Integrated geometric design definitions can define 3D reference models that are optimized to fit the integrated reference object. The integrated geometric design definition can define an optimized starting point from which to generate a 3D target model. For example, the learning methods can optimize the fit accuracy requirements, the 3D coordinate map of the 3D reference model, and/or the geometric constructs of the 3D reference model such 3D target models can be more efficiently generated for target objects that satisfy the match criteria of the integrated reference object.

The 3D reference model can be a model of one or more orthoses, prostheses, implants, non-medical devices, non-medical structures, or any combination thereof. For example, the 3D reference model can be a bracelet, a scoliosis brace, a bone screw, or any other device or structure, including floor tiles, engine gears, lower back supports for use with chairs. The 3D reference model can be custom designed to fit the reference object.

FIG. 2 further illustrates that the method 200 can involve identifying (also referred to as acquiring) one or more target objects in operation 206. Operation 206 can include acquiring target objects using, for example, a data acquisition device 102. The target objects can have the same or similar isomorphic topology as the one or more reference objects from which the 3D reference model is designed to fit.

Operation 206 can include identifying physical target objects and/or digital target objects using, for example, a data acquisition device 102. The identifying step 206 can involve sensing and/or imaging physical target objects. The identifying step 206 can involve receiving data (e.g., images) of an object in an electronic format (e.g., digital pictures) and/or in a physical format (e.g., physical pictures). Physical images can be converted to digital images. For example, operation 206 can include extracting one or more digital representations of physical target objects. The identifying step 206 can acquire data (e.g., images) of target objects. The data (e.g., images) can be configured to be visually displayed, for example, as a digital representation.

The target objects can be animate and/or inanimate objects. Animate objects can include any living organism, for example, people and/or animals. For example, operation 206 can include identifying a person's and/or animal's body, for example, the entire body, regions of the body (e.g., the torso, upper body, lower body), limbs (e.g., arms, legs), extremities (e.g., hands, feet), joints (e.g., knuckles, wrists, elbows, shoulders, ankles, knees, hips, sacroiliac joint, vertebral joints, rib joints, temporomandibular joints), or any combination thereof. Inanimate objects can include nonliving objects such as machines, robots, household items (e.g., furniture) and office equipment (e.g., chairs, desks). Animate and inanimate objects can be acquired (e.g., sensed, imaged) separately or together.

Operation 206 can generate data representative of the target objects acquired. For example, operation 206 can involve mapping the boundaries and/or surfaces of the target objects, determining the dimensions of the target objects, determining skin thicknesses, determining tissue percentages (e.g., % muscle, % fat), determining bone density, or any combination thereof.

Operation 206 can identify one or multiple target objects in a physical and/or digital representation of a data acquisition of a subject, where the subject can be an animate and/or inanimate object (e.g., a person or an animal). The target objects can be identified by a person, by computer vision, by an analysis of the data acquisition, or any combination thereof. For example, operation 206 can identify one or multiple target objects in a single image or group of images of a single subject (e.g., a person or an animal), for example, an image or group of images of an entire body of a subject. For example, operation 206 can identify 1 to 10 or more target objects in a subject's images, including every 1 target object increment within this range and/or beyond (e.g., less than 15 target objects, 15 or more target objects). Where a digital representation of a subject comprises a torso, for example, the target objects can be the vertebrae, ribs, the connections between the vertebrae and the ribs, the outer surface of the torso, or any combination thereof. Where a digital representation of a subject comprises a left arm, for example, the target objects can be one or more of the fingers, the hand, the wrist, the forearm, or any combination thereof. Multiple target objects can be identified in operation 206 to generate multiple 3D target models. The multiple 3D target models can be independent from one another, or can be configured to interact with one another.

Operation 206 can identify the target objects with one or multiple views, for example, 1 to 10 views, including every 1 view increment within this range. For example, operation 206 can involve acquiring target objects with first, second, third, and fourth views. The first, second, third, and forth views can be, for example, front, back, first side (e.g., left side), second side (e.g., right side) views of the target object, or any combination thereof. The foreground and/or background can be distinguished from the target object. The foreground and/or background can be filtered out of the image, ignored, or used for one or more reference points.

Operations 202 and 206 can identify the target and reference objects with the same views, the same set of views, with different views, with different sets of views, or any combination thereof. For example, operation 202 can acquire a reference object with a reference object first view, a reference object second view, and a reference object third view, and operation 206 can acquire a target object first view, a target object second view, and a target object third view. The reference and target object first views can be the same (e.g., top views) or different (top and bottom) from one another. The reference and target object second views can be the same (e.g., bottom views) or different (top and bottom) from one another. The reference and target object second views can be the same (e.g., left side views) or different (left and right side views) from one another.

The target object identified in step 206 can have the same or similar isomorphic topology as the one or more reference objects acquired in operation 202. The reference object acquired in operation 202 and the target object acquired in operation 206 can be acquired on the same day or on different days. The reference object acquired in operation 202 and the target object acquired in operation 206 can be acquired by the same data acquisition device 102 or by different data acquisition devices 102 (e.g., two different digital cameras, two different data acquisition techniques, for example, MRI and x-ray, digital camera and x-ray). The system 100 can reacquire the target object at any frequency depending on the subject's needs, including, for example, every 6 months to 5 years, including every 1 month increment within this range), and/or any time period less than 6 months. The reacquired target object can be a new target object, where the previous target object and/or previous reference object can be the new reference object. The target object can be reacquired where, for example, a new 3D target model is to be created and manufactured to accommodate the subject's anatomy, which may be needed where the subject's anatomical makeup has improved or deteriorated relative to when the 3D target model was first manufactured for the subject (e.g., where the curvature associated with scoliosis has worsened by becoming more curved).

The target objects can be the same or different from one or more of the reference objects. For example, the target and reference objects can be the same object where the same subject (e.g., person or animal) is acquired (e.g., imaged) in operations 202 and 206. Using the same subject in both the target and reference object identification operations 202, 206 can allow a subject's skeletal conditions (e.g., scoliosis), musculoskeletal conditions (e.g., polio), and/or response to treatment (e.g., with an implant, orthosis, prosthesis) to be tracked, for example, by comparing a subsequent target data representation (e.g., subsequent target image data) to a previously acquired target data representation (e.g., previous target image data) such that the previous target data representation becomes the new reference object in a second execution of operations 202 and 206. Imaging a different subject (e.g., person or animal) in operations 202 and 206 can also allow the target subject's skeletal conditions (e.g., scoliosis), musculoskeletal conditions (e.g., polio), and/or response to treatment (e.g., with an implant, orthosis, prosthesis) to be tracked, for example, by comparing subsequent target data representations (e.g., subsequent target image data) to one or more previously acquired target objects, to the previously used reference objects (e.g., non-integrated or integrated), to a new reference object (e.g., non-integrated or integrated), or any combination thereof. The new reference object can also be previously acquired but different from the previously acquired reference object(s) in some aspect, for example, by being acquired from a different subject (e.g., person), or by representing a machine learned optimization (e.g., an integrated reference object) of the previously acquired reference object(s) that is different from the previous reference object.

The reference and target objects can be associated with different subjects (e.g., different animate and/or inanimate subjects) where each subject can comprise one or multiple acquirable objects. For example, a limb or a torso of an animate subject (e.g., person or animal) can have one or multiple objects that can be acquired. A target object can be associated with a target subject and a reference object can be associated with one or more reference subjects different from the target subject. The reference and target subjects can be animate and/or inanimate, for example, people, animals, machines, robots, household items (e.g., furniture) and office equipment (e.g., chairs, desks). For example, the target object can be a left wrist of a first person and the reference object can be the right wrist of a second person. As another example, the target object can be the torso of a first person and the reference object can be the torso of a second person. The reference object can also be an integrated reference object. For example, the target object can be a left wrist of a first person and the integrated reference object can be a combination of two or more wrist reference objects of two or more people different from the first person. The integrated wrist reference object can be, for example, a combination of only left wrists, of only rights wrists, or of left and right wrists of the two or more people different from the first person. As another example, the target object can be a torso of a first person and the integrated reference object can be a combination of two or more torso reference objects of two or more people different from the first person.

Where the same subject is used for both the target object and the reference object, the images acquired in operations 202 and 206 can be on the same day and/or can be separated by a period of time, for example, from 1 day to 5 or more years, including every 1 day, 1 month, and 1 year increment within this range. For example, when designing a 3D model for a posture correction device the subject can first be acquired with their "bad" or "normal" posture and then again acquired with their "good" or "best attempted" posture, or vice versa. Using the same subject to create a brace (e.g., a first brace in a series of two or more braces) can help ensure that the first brace does not cause too much discomfort by correcting the posture in two or more increments instead of all at once, thereby encouraging the subject to regularly wear the brace. For example, to create a model for a shoulder posture brace, one brace or a series of braces can be created so that the correction can be implemented in stages and not cause too much discomfort to the subject. The series of braces can be created based solely on an initial (also referred to as first and baseline) reference and target object acquisitions. The series of braces can be created as the subject returns for more acquisitions, where a second target acquisition (operation 206) can be compared to a previous target object of the same subject, one or more reference objects of a different subject, an integrated reference object (which can include data from the target object subject), or any combination thereof.

Where a set of reference objects is used, the target objects can be the same object or a different object as compared to at least one of the objects in the reference object set.

As described above, reference and target objects can be any physical or digital object from a set of topologically isomorphic physical or digital objects. Physical objects can be any object which exists in 3D physical space. Examples of physical objects include the torso of a human, a surface of a chair, a torso of a dog, a knee of a human, a leg of a human, a back of a chair, a leg of a chair, a tail of a dog, a leg of a dog. Digital objects can be any 2D or 3D object represented in a format that can be parsed and rendered by any modern computing device and has been designed using Computer Aided Design (CAD) software and/or by a computer algorithm. Examples of digital objects include a drawing of a torso of a cat, a drawing of a leg of a dog, a drawing of a tail of a cat, a 3D degree rendering of a desk, a 3D degree rendering of the raised surface of a desk, a 2D image of cup of coffee, a 3D rendering of coffee in a cup, a 2D image of a knee of a human, a drawing of a subject's body or a portion thereof, or any digital model of a physical object.

A digital representation of a physical object can be any physical object captured as data acquired, for example, by sensors, imaging devices, computing devices, digital hand drawings, or any other image and/or data capturing technique. The digital representation can be of the form, or any combination of the form, including, for example, one or more of one or more of the following representations: (a) a digital 3D model rendering of a physical reference object and/or of a physical target object; (b) a 2D photograph of a physical reference object and/or of a physical target object; (c) a 2D illustration, 2D rendering and/or 2D image of a physical reference object and/or of a physical target object; (d) a 3D point cloud of a physical reference object and/or of a physical target object; (e) an x-ray image of a physical reference object and/or of a physical target object; (f) a magnetic resonance image (MRI) of a physical reference object and/or of a physical target object; (g) an ultrasound image of a physical reference object and/or of a physical target object; (h) an ultrasonographic image of a physical reference object and/or of a physical target object; (i) a computerized tomography (CT) scan of a physical reference object and/or of a physical target object (j) any other system or method of image capture of any physical or digital object, or any combination thereof.

FIG. 2 further illustrates that the method 200 can involve generating a 3D target model in operation 208 to fit the target object acquired in operation 206. The 3D target model can be generated, for example, by computing the geometric design definition determined in operation 204.

FIG. 2 further illustrates that the method 200 can involve validating the 3D target model in operation 210. For example, the 3D target model can be validated according to one or more fit accuracy parameters that are defined by the geometric design definition and/or defined by any further computation and/or iteration of the geometric design definition). The generated 3D target model can be compared to the digital representation of the target object that the 3D target model is generated to fit to determine whether or not the generated 3D target model fits the target object according to the fit accuracy parameters.

FIG. 2 further illustrates that the method 200 can involve adjusting the 3D target model in operation 212, for example, when the 3D target model generated in operation 208 does not satisfy the fit accuracy requirements with respect to the target object. Operation 210 can determine that the generated 3D target model does not satisfy the fit accuracy parameters when one or more of the parameters of the 3D target model are not within one or more threshold tolerances, upper threshold values, lower threshold values, threshold ranges, or any combination thereof, of one or more of the corresponding fit accuracy parameters associated with the geometric design definition and/or the 3D target model. The geometry of the generated 3D target model can be adjusted to better fit the target object in accordance with the fit accuracy requirements of the 3D reference model or a 3D target model design definition. The 3D target model design definition can be computed from the geometric design definition using, for example, one or more parameters of the target object (e.g., target object dimensions) as inputs.

FIG. 2 further illustrates that the method 200 can involve using the 3D target model validated in operation 210 in operation 214. Once the 3D target model is validated, one or more structures can be manufactured according to the 3D target model. For example, a single structure can be manufactured according to the validated 3D target model. The structure can provide support and/or can be a fashion product that does not provide support (e.g., a dress, a hat, gloves). As another example, a series of structures can be designed to progressively reposition or progressively provide more or less support to a portion of a person's body (e.g., back, shoulder) in two or more successive steps. Each structure in a series can correspond to a 3D target model that has a geometry that corresponds to an intermediate or end body (e.g., back, shoulder) arrangement intended for the structure in the series. A series of structures can have geometries designed to progressively reposition a portion of a person's body (e.g., back, shoulder) from a first arrangement through one or more successive intermediate arrangements to a final arrangement. The series can include any structure modeled (e.g., orthoses, prostheses, implants, non-medical structures). For example, a series of shoulder posture brace 3D target models can be created. As another example, a series of scoliosis brace 3D target models can be created. Each series can be manufactured all at once or as desired. Each structure in the series can correspond to a different 3D target model derived from a validated 3D target model. A series of structures can have 1 to 100 structures, including every 1 structure increment within this range.

FIG. 2 further illustrates that the method 200 can involve improving the geometric design definition in operation 216, for example, using one or multiple learning methods (e.g., using machine learning). For example, for improving the geometric design definition, operation 216 can use supervised and/or unsupervised online learning with machine learning techniques such as computer vision, statistical learning, deep learning, differential geometry, mathematical topology, natural language processing, including, regression, Markov models, support vector machines, Bayes Classifier, clustering, decision trees, neural networks, or any combination thereof.

The generation, validation and adjustment operations 208, 210, 212 can be repeated until the 3D target model fits the target object in accordance with the fit accuracy parameters.

The method 200 can further involve repeating and performing operations 202, 204, 206, 208, 210, 212, 214, 216, or any combination thereof.

The operations 202, 204, 206, 208, 210, 212, 214, and 216 can be interchangeably combined, rearranged, substituted, and/or omitted in any combination, and can be executed in any order, for example, in the order shown in FIG. 2. Additional operations that are not shown can be added to the method 200 or can be part of a separate implementable and/or performable method, for example, determining fit accuracy parameters, creating 3D coordinate maps, defining geometric constructs of the geometric design definition, adjusting fit accuracy parameters, adjusting 3D coordinate maps, adjusting geometric constructs of the geometric design definition, iteratively computing geometric design definitions, iteratively computing adjusted geometric design definitions, or any combination thereof, as well as any other process or operation described or contemplated herein.

Figure 3:
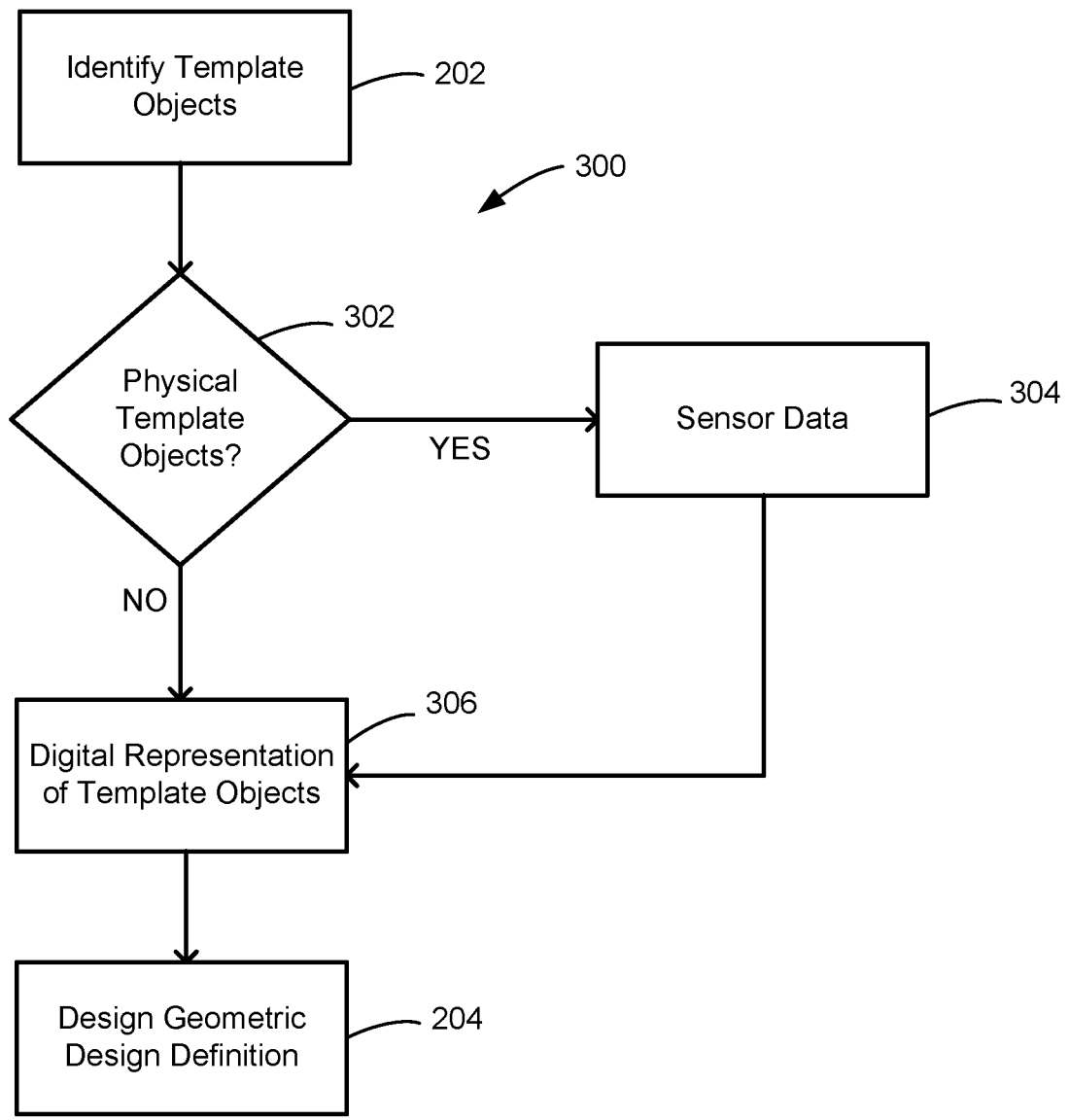
FIG. 3 illustrates a variation of a method undertaken by the system.

FIG. 3 illustrates a variation of a process 300 of capturing and/or generating a digital representation of one or more reference objects identified, for example, in operation 202. The process 300 can be a sub-routine of method 200, can be part of method 200, and/or can be a standalone process. FIG. 3 illustrates that once a reference object is identified a determination can be made whether or not the identified reference object is a physical object in operation 302. This determination can be made by a user of the method 200 or a processor configured to recognize the difference between physical and digital objects (e.g., using computer vision). If the reference object is a physical object (indicated by the "YES"), data from one or more data acquisition devices 102 (e.g., sensors) can be acquired and/or referenced in operation 304. The data acquired and/or referenced in operation 304 can be used to create a digital representation of the physical reference object in operation 306. If the reference object is not a physical object (indicated by the "NO"), the data acquired from one or more data acquisition devices 102 (e.g., sensors) in operation 202 of the reference object can be recognized as the digital representation of the reference object in operation 306. Additionally or alternatively, the data acquired in operation 202 can be referenced in operation 306 to create a digital representation of the reference object. The formulation of the geometric design definition in operation 204 can be based partly or entirely on the digital representation of the reference object generated, received, and/or acquired in operation 306. For example, the geometric design definition can be based on the digital representation of the reference object, one or more features sensed and/or detected on the reference object (e.g., measurements of one or more dimensions, areas, volumes), one or more parameters of the desired 3D reference model designed to fit the reference object (which can include the geometric design definition and one or more of the components thereof, including the fit accuracy parameters, the 3D coordinate map, the geometric constructs), or any combination thereof.

Figure 4A:
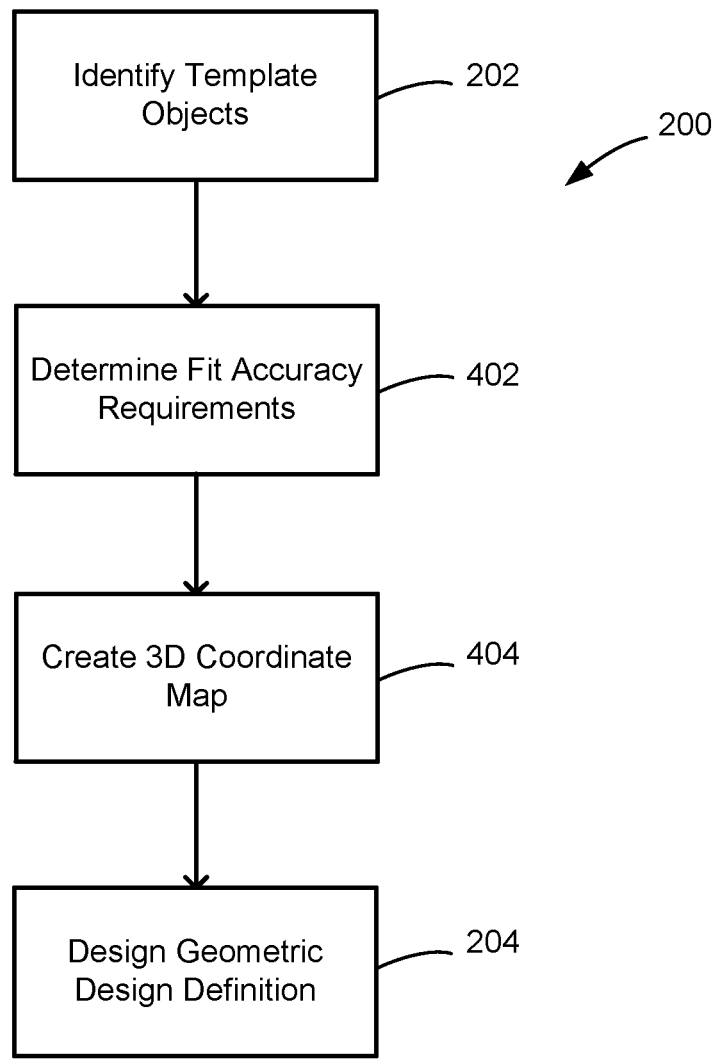
FIG. 4A illustrates a variation of a method undertaken by the system.

FIG. 4A illustrates that the method 200 can further involve determining fit accuracy parameters in operation 402. As described above, the fit accuracy parameters can include parameters that quantify the relationship between the reference objects and the 3D reference models that are designed to fit the reference objects. The fit accuracy parameters can include geometric and non-geometric parameters such that the geometric design definition can represent the geometric and non-geometric relationship between the reference objects and the 3D reference models designed to fit the reference objects. For example, the fit accuracy parameters can include dimensional parameters, pressure parameters, movement parameters, temperature parameters, moisture parameters, flexibility parameters, hardness parameters, or any combination thereof. Each fit accuracy parameter will depend on the design of the 3D reference model (e.g., the type of orthosis, prosthesis, and/or implant) and the reference object that the 3D reference model is designed to fit.

The fit accuracy parameters can comprise maximum and/or minimum parameter values. For example, the geometric fit accuracy parameters can include maximum and/or minimum dimensions between the 3D reference model and the reference object, relative dimensions of two or more portions of the 3D reference model (e.g., thickness between a first surface and a second surface of the 3D reference model), or any combination thereof. The non-geometric fit accuracy parameters can include maximum and/or minimum parameter values for pressure, temperature, moisture, force, flexibility, rigidity, or any combination thereof. For example, the pressure parameters can include maximum and/or minimum pressures applied by the 3D reference models to the reference object. The temperature parameters can include maximum and/or minimum temperatures tolerated between the reference object and the 3D reference model, for example, between a reference object contact surface and a 3D reference model contact surface, and/or maximum and/or minimum temperatures tolerated within a region of the 3D target model. The moisture parameters can include maximum and/or minimum moisture content values (e.g., volumes) tolerated between the reference object and the 3D reference model and/or at a 3D reference model contact surface that is designed to contact the reference object. The moisture parameters can depend on a sweat estimate from the reference object against a reference object contact surface of the 3D reference model. The force parameters can include internal force parameters and/or external force parameters, where maximum and/or minimum values can be associated with each. For example, the external force parameters can be the minimum and maximum external forces that the 3D reference model can tolerate. The internal force parameters can be the minimum and/or maximum internal forces that the 3D reference model can tolerate. The flexibility parameters (also referred to as elasticity parameters) can include maximum and/or minimum angles of deflection, for example, between first and second points of the reference model. The rigidity parameters (also referred to as hardness and softness parameters) can include maximum and/or minimum stiffness values, where the stiffness can be a measure (e.g., in pounds per inch) of the resistance of the 3D reference model to deflection from an applied force (e.g., stiffness=applied force/displacement of 3D reference model from applied force).

The fit accuracy parameters can include geometric proximity parameters that represent the geometric proximities between the reference object and the 3D reference model designed to fit the reference object. The geometric proximity parameters can be dimension dependent (also referred to as dimension-based). For example, the proximity parameters can include minimum distances between points of the reference object and points of a 3D reference model designed to fit the reference object, maximum distances between points of the reference object and points of a 3D reference model designed to fit the reference object, or any combination thereof. The geometric proximity points associated with the 3D reference model can be on a surface (e.g., interior or exterior surface) of the 3D reference model and/or within the 3D reference model. The geometric proximity points associated with the reference object can be on a surface (e.g., interior or exterior surface) of the reference object and/or within an interior region of the reference object. The interior surface and/or interior region of the reference object can correspond to, for example, a blood vessel surface, a bone surface, or a muscle surface.

The minimum distances can be determined between surface points associated with the 3D reference model designed to fit the reference object and surface points of the reference object and/or interior points of the reference object. The minimum distances can be determined between interior points associated with the 3D reference model designed to fit the reference object and surface points of the reference object and/or interior points of the reference object. The maximum distances can be determined between surface points associated with the 3D reference model designed to fit the reference object and surface points of the reference object and/or interior points of the reference object. The maximum distances can be determined between interior points associated with the 3D reference model designed to fit the reference object and surface points of the reference object and/or interior points of the reference object. The minimum and/or maximum distances can be determined between two or more surfaces, for example, between a first point on a first surface and a second point on a second surface. A portion of a first surface or an entire first surface can be a uniform or non-uniform minimum and/or maximum distance from a portion of a second surface or an entire second surface such that fit accuracy parameter can require that a surface of the 3D reference model be a uniform or non-uniform minimum and/or maximum distance from a surface of the 3D reference object. The maximum distances can be measured along a straight and/or curved line between two points. The minimum and maximum distances will depend on the design of the 3D reference model (e.g., the type of orthosis, prosthesis, and/or implant) and the reference object that the 3D reference model is designed to fit. The minimum distances can range, for example, from about 0 mm to about 10 mm, including every 0.1 mm increment within this range. The maximum distances can range, for example, from about 0 mm to about 1,000 mm, including every 0.1 mm increment within this range. For example, where the 3D reference model is a bracelet, the minimum and maximum distances can be 0.0 mm and 5.0 mm, respectively. Where the 3D reference model is a brace (e.g., scoliosis brace, shoulder posture brace), the minimum and maximum distances can be 0.0 mm and 2.0 mm, respectively. However, the minimum and maximum distances can depend on where the distance is being measured between. For example, different minimum and maximum distances can correspond to different points, surfaces and/or regions of the 3D reference model. For example, the maximum distance between a first wristband portion and a first wrist portion can be 2.0 mm and the maximum distance between a second wristband portion and a second wrist portion can be 5.0 mm. For example, the first wristband and wrist portions can a top and or bottom of each and the second wristband and wrist portions can be a side of each.

The fit accuracy parameters can include non-geometric fit accuracy parameters such as pressure parameters (also referred to as pressure-based parameters) that represent the pressure relationships between the reference object and a 3D reference model designed to fit the reference object. For example, the pressure parameters can include minimum pressures applied by surfaces of a 3D reference model to surfaces of the reference object, maximum pressures applied by surfaces of a 3D reference model to surfaces of the reference object, or any combination thereof. The pressure points associated with the 3D reference model can be on a surface (e.g., interior or exterior surface) of the 3D reference model and/or within the 3D reference model. The pressure points associated with the 3D reference model can be on a surface (e.g., interior or exterior surface) of the 3D reference model and/or within the 3D reference model. The pressure points associated with the reference object can be on a surface (e.g., exterior surface) of the reference object.

The minimum and maximum pressures will depend on the design of the 3D reference model (e.g., the type of orthosis, prosthesis, and/or implant) and the reference object that the 3D reference model is designed to fit. The minimum pressure can range from about −20.0 psi to about 20.0 psi (e.g., about 0.0 psi to about 20.0 psi), including every 0.1 psi increment within this range. The maximum pressure can range from about −40.0 psi to about 40.0 psi (e.g., about 0.0 psi to about 40.0 psi), including every 0.1 psi increment within this range. For example, where the 3D reference model is a bracelet, the minimum and maximum pressures can be 0.0 psi and 4.0 psi, respectively. Where the 3D reference model is a brace (e.g., scoliosis brace, shoulder posture brace), the minimum and maximum pressures can be 0.0 psi and 20.0 psi, respectively. However, the minimum and maximum pressures can depend on where the pressure is being measured on the 3D reference model relative to the reference object. For example, for a torso brace (e.g., scoliosis brace), the maximum pressure can be about 6.0 psi on ribs.

The minimum and/or maximum pressures can be negative, for example, when the 3D reference model is configured to receive negative pressure. Negative pressure can be below a reference pressure such as atmospheric pressure. The 3D reference model can be designed to receive negative pressure when the system 100 has a vacuum source (e.g., a pump). The 3D reference model can be designed so that the vacuum source can be attached to and/or integrated with a structure (e.g., structure 150). One or more portions of the 3D reference model can be configured to be brought to a negative pressure. For example, the 3D reference model can have one or more internal channels (also referred to as pressure channels) that extend partially or entirely around a perimeter (e.g., circumference) of a 3D reference model. The pressure channels can be configured to be brought to a negative pressure when the 3D reference model is used. The internal channels can be designed to follow the contours or a portion of the shape of a reference object. For example, the pressure channels can form one or more pressure rings and/or pressure arcs.

The pressure channels can be configured to apply force to the reference object. For example, the 3D reference model can be designed with pressure channels configured support one or more ribs of the left and/or right rib cages when brought to a negative pressure. The pressure channels can be configured to constrict when filled with negative pressure. The pressure channels can advantageously provide force (when at a negative pressure) against a reference object. The pressure channels can advantageously allow the 3D reference model (and the manufactured 3D reference models) to focus the force applied against the reference object by the 3D reference model when at a negative pressure. The pressure channels can supplement the tensile force and/or compressive forces that the 3D reference model can be designed to apply to the reference object. The pressure channels can be the only force against the reference object at the location of the pressure channels. Additionally or alternatively, one or more pressure channels can be brought to a positive pressure. The pressure channels can be configured to expand when filled with positive pressure. An outer surface of the pressure channel can be rigid or resistant to expansion away from the reference object, forcing the expansion toward the reference object to apply a compressive force against the reference object.

The 3D reference models can have one or multiple fit accuracy parameters, for example, multiple maximum distances, multiple minimum distances, multiple maximum pressures, multiple minimum pressures, or any combination thereof. The different fit accuracy parameters can correspond to different points, surfaces, and/or regions of the 3D reference model in relation to the one or more reference objects that the 3D reference model is designed to fit.

One or more of the fit accuracy parameters can be critical parameters for the 3D reference models. Critical fit accuracy parameters can be parameters that must be satisfied by a generated 3D target model to be validated in operation 210. Any or all of the fit accuracy parameters can be a critical fit accuracy parameter. For example, the dimension-based and the pressure-based fit accuracy parameters can be critical parameters, where the 3D target model must satisfy every dimension-based fit accuracy parameter (e.g., maximum distances, minimum distances) and/or every pressure-based fit accuracy parameter (e.g., maximum pressures, minimum pressures) to be validated in operation 210. Additionally or alternatively, one or more of the dimension-based parameters can be critical and/or non-critical parameters, one or more of the pressure-based parameters can be critical and/or non-critical parameters, or any combination thereof. For example, the dimension-based parameters between a first surface of a reference object and a first surface of a 3D reference model can be critical parameters whereas the dimension-based parameters between the first surface (or a second surface) of the reference object and a second surface of the 3D reference model can be non-critical parameters. For example, one or more dimension-based parameters between an inner surface of the 3D target model and an outer surface of the target object can be critical parameters (e.g., between an inner surface of a wristband and the skin of a wrist reference object), one or more dimension-based parameters between an outer surface of the 3D target model and an outer surface of the target object can be non-critical parameters (e.g., between an outer surface of a wristband and the skin of a wrist reference object), or any combination thereof.

FIG. 4A further illustrates that the method 200 can involve creating a 3D coordinate map in operation 404. The 3D coordinate map can include multiple points (also referred to as markers) that represent the geometric relationship between the reference objects and the 3D reference models designed to fit the reference objects. The 3D coordinate points can be automatically generated by the system 100 in operation 404. Additionally or alternatively, one or multiple 3D coordinate points can be manually input into the system, for example, from a user using a control interface. The computer generated 3D coordinate points and/or the manually input 3D coordinate points can be applied to the digital representation of the reference object. One or more of the points can be critical to the design of the 3D reference model. For example, each point can be critical to the design of the 3D reference model. The 3D coordinate map can include for example, 2 markers to 1,000,000 or more markers, including every 1 marker increment within this range, as well as every 1,000 marker range within this range (e.g., 2-1002 markers, 1002-2002 . . . 999,002-1,000,000). The point density of the 3D coordinate map can range from, for example, 0 to 1,000 markers per 100 mm², including every 1 marker increment within this range or beyond.

The 3D coordinate map can be created, for example, based on the fit accuracy parameters determined in operation 402, the geometric features of the reference object, user input, or any combination thereof. The 3D coordinate map can be a function of the one or more (including all) of the fit accuracy parameters determined in operation 402. The 3D coordinate map can be independent of one or more (including all) of the fit accuracy parameters determined in operation 402.

The 3D coordinate points created in operation 404 can be a point frame of the 3D reference model being designed to fit the reference object. For example, the 3D coordinate points created in operation 404 can function as digital scaffolding for the geometric constructs and/or fit accuracy parameters determined in operations 402 and 204, respectively.

The 3D coordinate points created in operation 404 can be created to reflect the fit accuracy parameters, such as the various distance and/or pressure parameters, the geometric constructs of the 3D reference model, the geometric features of the reference object, or any combination thereof. For example, the 3D coordinate points can be independent of or dependent on (e.g., partly or entirely based on) the fit accuracy parameters and/or the geometric constructs of the 3D reference model. The 3D coordinate map can be applied to the digital representation (e.g., digital image) of a reference object. For example, the points of the 3D coordinate map can be digitally superimposed on the digital representations of the reference objects. The 3D coordinate points can represent a mathematical and visual mapping between the reference object and a 2D and/or 3D coordinate system for creating the 3D reference model.

FIG. 4A further illustrates that the geometric design definition of the 3D reference model can be created in operation 204. The geometric design definition can be created with one or more geometric constructs (also referred to as geometric definition elements). The geometric constructs determined in operation 204 can be created independent of or dependent on (e.g., partly or entirely based on) the fit accuracy parameters and/or the 3D coordinate map determined in operations 402 and 404, respectively. The geometric design definition quantitatively (e.g., mathematically) and/or qualitatively (e.g., descriptively) define the geometric constructs of the 3D reference model. The geometric design definition of the 3D model can define (also referred to as have) one or more geometric constructs, for example, points (e.g., 2D points, 3D points), lines, polylines, arcs, polyarcs, polynomial splines, ellipse arc splines, curves, bezier curves, free-form points, free-form lines, free-form arcs, free-form curves, nurbs curves, nurbs surfaces, extruding, lofting, sweeping, revolving, extruding along a curve, sweeping along a curve, lofting curves, lofting surfaces, extruding along a surface, surfaces (e.g., flat, curved, parametric, non-parametric), 2D shapes (e.g., circles, ellipses, triangles, stadiums, squares, rectangles, polygons), 3D shapes, solids, volumes, or any combination thereof. Such geometric constructs can be represented visually, descriptively and/or mathematically (e.g., by one or more mathematical equations.

One or more of the geometric constructs can include the coordinate points created in operation 404, can be derived from the coordinate points created in operation 404, can include markers representative of the fit accuracy requirements determined in operation 402, can be derived from the fit accuracy requirements determined in operation 402, or any combination thereof. For example, the geometric construction of the 3D reference model (also referred to as the geometric design definition) can be entirely or at least partly based on the 3D coordinate map of the 3D reference model generated, for example, in operation 404. The specific geometric design definitions created in operation 204 will depend on the desired geometric features of the 3D reference models designed to fit the reference objects.

The geometry of the 3D reference model can be represented as a mathematical description. For example, the geometric design definition can be a mathematical 3D definition comprising human and/or computer readable text. A geometric design definition file can be used to transmit data objects comprising geometric features that represent the underlying geometric structure of the 3D object defined by the text (e.g., the 3D reference model). The geometric design definition can be rendered, digitally viewed, and/or manufactured using the geometric design definition file, for example, by executing the file (also referred to as computing the geometric design definition). Computing the geometric design definition file can be directly rendered into a 3D object model, for example, a 3D target model.

Once one or more target objects are identified (e.g., in operation 206), 3D target models can be generated to fit target objects using one or more geometric design definitions (e.g., in operation 208). The geometric design definitions can define the 3D reference models based on one or more reference objects as data inputs. The reference objects can be identified in operation 202. The one or more reference objects can be retrieved from a library of stored reference objects. The geometric design definition can include descriptions of the geometric constructs of the 3D reference model, can reference the 3D coordinate mapping generated in operation 404, can reference the fit accuracy parameters in operation 402, or any combination thereof.

Generating 3D target models in operation 208 can involve creating a modified 3D coordinate map (also referred to as a 3D target coordinate map) between the 3D reference model and the target objects. The 3D coordinate mapping generated in operation 404 (also referred to as a 3D reference coordinate map) can be modified to fit one or multiple target objects. For example, the geometric design definition of the 3D reference model and/or the 3D coordinate mapping of the 3D reference object can be used to map the 3D reference model to the target objects. The 3D target model can be generated by computing the geometric design definition of the 3D reference model with the modified 3D coordinate map for the target objects as inputs. For example, the geometric design definition of the geometry of the 3D reference model can include reference variables corresponding to the 3D coordinate map of the 3D reference model. To generate 3D target models, these reference variables can be substituted with the points (e.g., the X, Y, and Z Cartesian coordinate values of each point) of the modified 3D coordinate map associated with the target objects, and the resulting geometry can be processed to generate a 3D target model that fits the target objects.

To determine the modified 3D mapping coordinates for one or more target objects, the geometric design definitions of the 3D reference models can be first computed with the 3D coordinate maps created between the 3D reference models and the reference objects, which will generate digital representations of the 3D reference models. A rendering (e.g., 2D or 3D rendering) of the generated 3D reference models, the fit accuracy requirements, the 3D reference coordinate maps, or any combination thereof, can be overlaid on the digital representations of the target objects. The 3D reference models can be rendered with or without the fit accuracy requirements and/or the 3D reference coordinate maps from which the 3D reference models can be based. The 3D target coordinate maps that represent the geometric relationship between the 3D target models and the target objects can be determined based on measurements and differences determined by analyzing the computed geometric design definition and/or overlaid data. For example, the measurements and/or differences can be distances between one or more points of the 3D reference map and the target object, can be distances between one or more points of the geometric constructs of the 3D reference model and the target object, or any combination thereof.

The 3D target coordinate maps can be manually and/or automatically (e.g., with a processor) created based on the visual and/or mathematical data derived from the overlaid data and/or derived from the rendered 3D reference model without overlaying the fit accuracy requirements and/or the 3D reference coordinate maps. Additionally or alternatively, the 3D target coordinate maps between the 3D target models and the target objects can be manually and/or automatically (e.g., with a processor) created based on mathematical data of non-rendered 3D reference models (e.g., non-rendered geometric constructs of the geometric design definition), non-rendered fit accuracy requirements, non-rendered 3D reference coordinate maps, or any combination thereof. The overlaid renderings can be scaled to have the same scale or to have sizes proportionate to one another (e.g., scaled to their actual size, less than their actual size, or larger than their actual size) and can be viewed on any modern computing device including, for example, a desktop computer, a laptop computer, a tablet computing device, a smartphone computing device, a network of one or more computing systems which can be accessed over Internet-based networks, or any combination thereof.

The geometric design definition of the 3D reference model can be computed with the 3D target coordinate maps for the target objects, thereby generating 3D target models to fit the target objects.

The 3D reference coordinate maps and/or the 3D target coordinate maps can be created with, for example, computer vision, statistical learning, deep learning, differential geometry, mathematical topology, or any combination thereof, including, for example, feature detection, feature extraction, object detection, object recognition, edge detection, context-based image classification, pose estimation, 3D reconstruction, photogrammetry. Such techniques can be used to estimate, calculate, and determine the 3D reference coordinate map between the 3D reference model and the reference objects. Such techniques can be used to estimate, calculate, and determine the 3D target coordinate map between the 3D reference model and the target objects with or without overlaying the 3D reference model on the target object. Such techniques can be used to estimate, calculate, and/or determine the measurements and differences between one or more points of the 3D reference map and the target object, between one or more points of the geometric constructs of the 3D reference model and the target object, or any combination thereof. The geometric design definition of the 3D reference model can be computed with the modified 3D coordinate map to generate a 3D target model designed to fit target objects.

Additionally or alternatively, the geometric design definition of the 3D reference model can be computed with target object parameters unaffiliated with the 3D reference coordinate map such that the 3D target model can be generated with or without determining a 3D target coordinate map. The target object parameters can include geometric and/or non-geometric parameters. The geometric target object parameters can correspond to the geometry of the target object. Target object geometry parameters can be any observable, measureable, derivable, and/or detectable feature of the target object, for example, dimensions, boundaries, edges, points, lines, points of inner surfaces, points of inner edges, points of outer surfaces, points of outer edges, points of target interiors, surface areas, and volumes. The target geometry parameter points can be 2D or 3D points (e.g., 2D or 3D Cartesian coordinate points). The target geometry parameter lines and surfaces can be mathematical equations. The target geometry lines and surfaces can be represented as a group of points. The non-geometric target object parameters can correspond to, for example, the age, weight, gender, physical condition of the target object, long-form input (e.g., user narrative, medical professional narrative), or any combination thereof. Non-geometric parameters can be useful where the geometric design definition is configured to change one or more features of the 3D reference model (e.g., the thickness of the 3D reference model, change the pressure-based fit accuracy parameters of the 3D reference model) based on such non-geometric parameters. For example, the geometric design definition can be defined to increase the thickness of the 3D reference model for people above an age threshold (e.g., above 50 years old, above 60 years old, above 70 years old) to increase the 3D reference model's insulative effect, and/or where long-form data was entered into the system (e.g., system 100) indicating that the subject lives in a cold climate. As another example, the geometric design definition can be defined to decrease one or more of the pressure-based fit accuracy requirements where long-form data has been entered that the subject has sensitive skin or is above an age threshold (e.g., above 50 years old, above 60 years old, above 70 years old). The geometric design definition can include object input variables for the geometric and non-geometric constructs. The target object geometric and/or non-geometric parameters can be inserted into the geometric design definition as the object input variables and then computed to generated a 3D reference model.

The geometric design definition can be computed within any input from the operations disclosed, illustrated, and/or contemplated. For example, the geometric design definition can be computed with target object parameters, reference object parameters, 3D target model parameters, 3D reference model parameters, fit accuracy parameters, 3D coordinate maps (e.g., 3D reference coordinate maps, 3D modified coordinate maps, 3D adjusted coordinate maps), geometric constructs, or any combination thereof. For example, the 3D coordinate map for the target object can be determined, 3D target coordinate map can be substituted into the geometric design definition, and the geometric design definition can be computed with the 3D target coordinate map to generate a 3D target model.

Figure 4B:
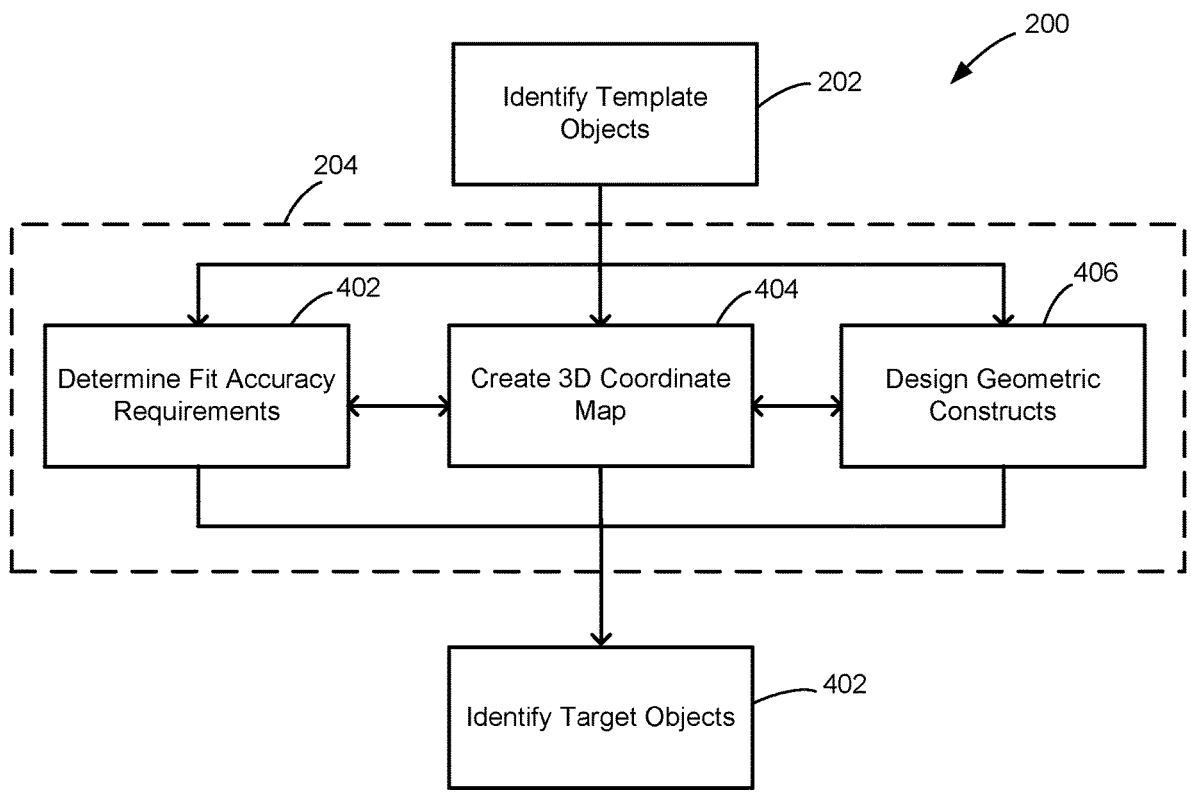
FIG. 4B illustrates a variation of a method undertaken by the system.

FIG. 4B illustrates that the method 200 can further involve determining fit accuracy parameters in operation 402, creating a 3D reference coordinate map in operation 404, and/or designing geometric constructs of the 3D reference model in operation 406. FIG. 4B further illustrates that determining the geometric design definition in operation 204 can include operations 402, 404, and/or 406. Operations 402, 404, and/or 406 can be determined, created, and/or designed independent of and/or dependent on one another.

Figure 5:
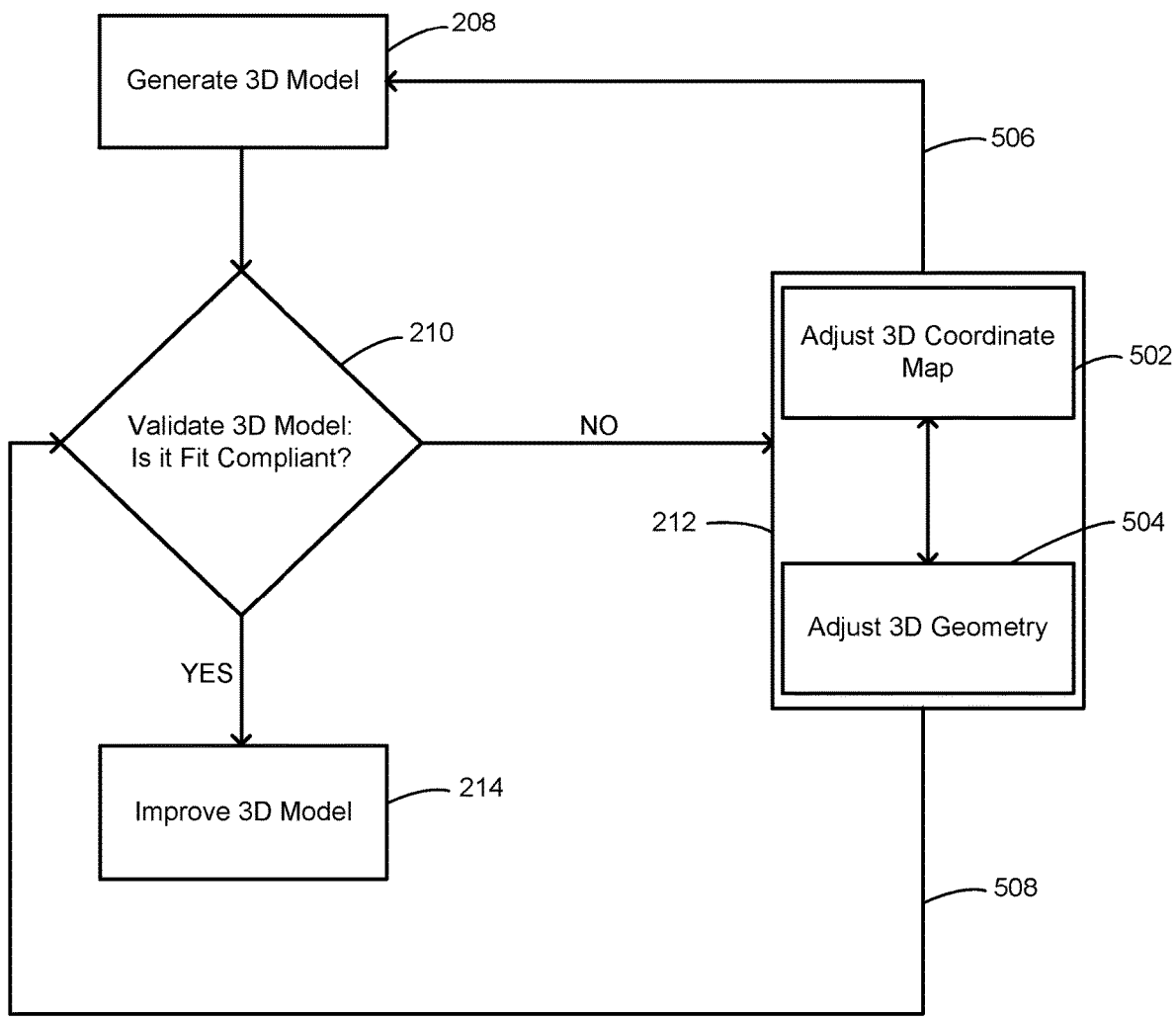
FIG. 5 illustrates a variation of a method undertaken by the system.

FIG. 5 illustrates a variation of the validation and adjustment operations 210, 212. For example, a determination can be made in operation 212 whether or not the 3D target model is fit compliant. The 3D target model can be fit compliant when the 3D target model satisfies each of the critical fit accuracy requirements associated with the geometric design definition. Additionally or alternatively, the 3D target model can be fit compliant when the 3D target model satisfies one or more non-critical fit accuracy requirements. The critical fit accuracy requirements can be the dimension-based fit accuracy parameters (e.g., maximum distances, minimum distances) and the pressure-based fit accuracy parameters (e.g., maximum pressures, minimum pressures). The non-critical fit accuracy requirements can be non-dimension based and/or non-pressure based fit accuracy parameters (e.g., temperature and/or moisture fit accuracy parameters). The 3D target model can be fit compliant when one or more parameters of the 3D target model are within, above, and/or below one or more validation thresholds (e.g., threshold tolerances, upper threshold values, lower threshold values, threshold ranges, or any combination thereof) associated with the critical fit accuracy requirements and/or the non-critical fit accuracy requirements. The validation thresholds can correspond to, for example, maximum and minimum values. For example, the validation thresholds can correspond to the fit accuracy parameters associated with the geometric design definition and/or the 3D reference model.

The 3D target model can have multiple validation points (also referred to as target model validation points), for example, from 1 to 1,000,000 or more validation points, including every 1 validation point increment within this range, as well as every 100 and 1,000 validation point range within this range (e.g., 1-100, 101-200 . . . 999,901-1,000,000 points and 1-1000 validation points, 1001-2000 . . . 999,001-1,000,000). Each validation point can correspond to a geometric or non-geometric parameter of the 3D target model. The target model validation points can be validated using one or more of the fit accuracy parameter thresholds. If a validation point satisfies a threshold, the validation point can be validated. If a validation point does not satisfy a threshold, the validation point can be electronically marked for adjustment. The points marked for adjustment can be adjusted in operation 212. The points marked for adjustment can be graphically displayed prior to adjustment in operation 212.

The 3D target model can be validated if every one of the critical fit accuracy requirement is satisfied by the validation points that are compared against the critical fit accuracy requirements. Some or all of the validation points of the 3D target model can be tested against the critical fit accuracy requirements. For example, some or all of the validation points can be tested against one type of critical fit accuracy requirement (e.g., a dimension- or pressure-based requirement), multiple types of critical fit accuracy requirements (e.g., dimension- and pressure-based requirements), or any combination thereof. Additionally or alternatively, the 3D target model can be validated if some or all of the non-critical fit accuracy requirements are satisfied by the validation points compared against the non-critical fit accuracy requirements. For example, the 3D target model can be validated if a validated point threshold percentage associated with the critical and/or non-critical fit accuracy requirements is matched or exceeded. For example, the 3D target model can be validated if about 75% to about 100% of the validation points are validated against non-critical fit accuracy requirements, including every 1% increment within this range (e.g., 75%). As another example, the 3D target model can be validated if about 75% to about 100% of the validation points are validated against critical fit accuracy requirements, including every 1% increment within this range (e.g., 100%).

The 3D target model can be separated into multiple validation regions (e.g., 2 to 1,000 regions, including every 1 region within this range), where each region can have between 10 validation points and 100,000 or more validation points, including every 1 validation point within this range. More critical regions can have more validation points than less critical regions. The 3D target model can be validated if each of the validation regions satisfies the validation point threshold percentage. For example, the 3D target model can be validated if about 75% to about 100% of the validation points are validated against the critical and/or non-critical fit accuracy requirements within each of the validation regions, including every 1% increment within this range. The 3D target model can be marked for adjustment if one or more of the validation regions do not satisfy the threshold percentage associated with the critical thresholds and/or the non-critical thresholds.

3D target models that are validated (indicated by the "YES" line between operations 212 and 214 in FIG. 5) can be marked as improved in operation 214, for example, by virtue of being validated in operation 210 (e.g., if the 3D target model is not adjusted prior to validation) or by virtue of being adjusted in operation 212 (e.g., one or more times) and then validated in operation 210. 3D target models that are not validated (indicated by the "NO" line between operations 210 and 212 in FIG. 5) can be adjusted in an adjustment step 212, for example, by adjusting the location of one or more points of the modified 3D coordinate map that was used to generate the 3D target model that was marked for adjustment. After the adjustment, a subsequent (e.g., a second) 3D target model can be digitally generated by again executing operation 208, after which the validation operation 210 can be performed again. The generation, validation and adjustment operations 208, 210, 212 can be repeated (also referred to as iterated) until the 3D target model generated in operation 208 fits the target object in accordance with the fit accuracy parameters. As described above, the fit of the 3D target model can be determined by comparing the 3D target model to the fit accuracy parameters, which can involve comparing a difference between the 3D target model parameters and the target object parameters to critical and/or non-critical fit accuracy parameter thresholds (also referred to as validation thresholds).

The fit accuracy requirements can have tolerances associated with the fit accuracy thresholds, for example, plus and/or minus about 0.1% to about 5% or more, including every 0.1% increment within this range, or more broadly, from about 0.1% to about 250% or more, including every 0.1% increment within this range (e.g., 6.8%, 7.9%, 10.3%, 50.0%, 102.4%, 250.0%, 300%). The "plus" and "minus" percentages can be the same or different as one another (e.g., plus and minus 2.0%, plus 2.0% and minus 5.0%). If the 3D target model validation points satisfy the fit accuracy requirements within the associated tolerance, the validation point of the 3D target model can be validated. The validation points that do not satisfy the fit accuracy requirements within the associated tolerance can be marked for adjustment. One or all of the fit accuracy parameters can have a tolerance. For example, the dimension-based fit accuracy requirements can have a tolerance of plus and/or minus about 0.1% to about 5.0%. For example, the maximum distance thresholds can have a tolerance of minus 2.0% such that if the maximum distance threshold is 10.0 mm, the validation point will comply with the maximum distance fit accuracy parameter if the validation point is a distance of about 9.8 mm to about 10.0 mm from the validation point to wherever the maximum distance is being measured against (e.g., the target object). As another example, the maximum distance threshold can have a tolerance of plus 2.0% such that if the maximum distance threshold is 10.0 mm, the validation point will comply with the maximum distance fit accuracy parameter if the validation point is a distance of about 10.0 mm to about 10.2 mm from the validation point to wherever the maximum distance is being measured against (e.g., the target object). As yet another example, where the minimum distance thresholds have a tolerance of plus and minus 1.0% and the minimum distance threshold is 1.0 mm, the validation point will comply with the maximum distance fit accuracy parameter if the validation point is a distance of about 0.99 mm to about 1.01 mm from the validation point to wherever the maximum distance is being measured against (e.g., the target object). The pressure-based fit accuracy requirements can have a tolerance of plus and/or minus about 0.1% to about 25.0%. For example, the maximum pressure threshold can be minus 10% such that if the maximum pressure fit accuracy parameter is 15.0 psi, the validation point will comply with the maximum pressure fit accuracy parameter if the validation point applies a pressure to the target object between about 13.5 psi and about 15.0 psi.

The one or multiple threshold values and/or ranges of the fit accuracy requirements can include, for example, dimensional values, dimensional ranges, pressure values, pressure ranges, temperature values, temperature ranges, expected moisture from underlying skin, or any combination thereof.

The lower threshold values can correspond to the minimum distance and/or pressure accuracy fit parameters associated with the geometric design definition. Additionally or alternatively, the lower threshold values can correspond to the minimum distance and/or pressure accuracy fit parameters associated with the 3D target model. The fit accuracy parameters of the 3D target model can be proportionately the same as the fit accuracy parameters (e.g., the minimum distance and/or pressure accuracy fit parameters) associated with the 3D reference models. For example, as described above, the minimum distance accuracy fit parameters can range from about 0 mm to about 10 mm, including every 0.1 mm increment within this range. The minimum pressure fit accuracy parameters can range from about 0 psi to about 20 psi, including every 1 psi increment within this range.

The upper threshold values can correspond to the maximum distance and/or pressure accuracy fit parameters associated with the geometric design definition. Additionally or alternatively, the upper threshold values can correspond to the maximum distance and/or pressure accuracy fit parameters associated with the 3D target model. The fit accuracy parameters of the 3D target model can be proportionately the same as the fit accuracy parameters (e.g., the maximum distance and/or pressure accuracy fit parameters) associated with the 3D reference models. For example, as described above, the maximum distance accuracy fit parameters can range from about 0 mm to about 100 mm, including every 0.1 mm increment within this range. The maximum pressure fit accuracy parameters can range from about 0 psi to about 40 psi, including every 1 psi increment within this range.

The threshold validation ranges for the distance-based fit accuracy parameters can be, for example, plus and/or minus about 0.1 mm to about 5 mm from a minimum and/or maximum distance, including every 0.1 mm increment within this range. The "plus" and "minus" amounts can be the same or different as one another (e.g., plus and minus 0.1 mm, plus 0.2 mm and minus 0.1 mm). For example, the threshold range for a maximum distance fit accuracy parameter can be minus 0.1 mm such that if the maximum distance fit accuracy parameter is 10.0 mm, the validation point will comply with the maximum distance fit accuracy parameter if the validation point is a distance of about 9.9 mm to about 10.0 mm from the validation point to wherever the maximum distance is being measured against (e.g., the target object). The threshold validation ranges for the pressure-based fit accuracy parameters can be, for example, from about 1 psi to about 10 psi from a minimum and/or maximum pressure, including every 1 psi increment within this range. For example, the threshold range for a maximum pressure fit accuracy parameter can be minus 1.0 psi such that if the maximum pressure fit accuracy parameter is 15.0 psi, the validation point will comply with the maximum pressure fit accuracy parameter if the validation point applies a pressure to the target object between about 14.0 psi and about 15.0 psi.

Operation 212 can determine that the generated 3D target model does not match (also referred to as comply with) the fit accuracy parameters when one or more of the parameters of the 3D target model are not within a threshold tolerance, below a threshold value, and/or above a threshold value of one or more of the corresponding fit accuracy parameters associated with the geometric design definition and/or the 3D reference model.

When a 3D target model is not fit compliant, the method can further involve adjusting the parameters of the 3D target model in operation 212.

For example, operation 212 can involve validating the compliance of 3D target models with the fit accuracy parameters of the 3D reference model. Fit accuracy parameters can be used (e.g., created) that allow for 3D target models to be generated that fit target objects that are in the same or similar isomorphic topology as one or multiple reference objects. The generated 3D target models can be analyzed (manually or via computer) in relation to the target objects upon which the 3D target models are generated to fit to determine if the fit of the generated 3D models are compliant with the fit accuracy requirements of the 3D reference model design.

To validate the fit between the generated 3D target model and the target object, a 2D or 3D rendering of the generated 3D target model can be overlaid on the digital representation of the target object. The overlaid rendering and digital representation data can be compared to one another visually and/or mathematically to determine the compliance of the 3D target model with the fit accuracy parameters associated with the geometric design definition. However, the 3D target model and the digital representation of the target object can be compared to one another with or without being overlaid. Fit compliance of the 3D target model can determined based on measurements and differences between the 3D target model and the target object. These measurements and differences can be compared against the fit accuracy parameters. The measurements and differences can be determined, for example, using validation points of the 3D target model. The renderings of the target object and the 3D target model can be scaled to have the same scale or to have sizes proportionate to one another (e.g., scaled to their actual size, less than their actual size, or larger than their actual size) and can be and viewed using any modern computing device including, for example, a desktop computer, a laptop computer, a tablet computing device, a smartphone computing device, a network of one or more computing systems which can be accessed over internet-based networks, or any combination thereof. Where the generated 3D target model is not compliant with the fit accuracy parameters, the geometry of the generated 3D target model can be adjusted (e.g., in operation 212). The geometry of generated 3D target models can be adjusted to increase compliance with the fit accuracy parameters of the 3D reference model design with respect to one or more specific target objects.

FIG. 5 further illustrates that the adjustment operation 212 can include adjusting the 3D coordinate map of the target object in operation 502, adjusting the 3D geometry of the 3D target model in operation 504, or any combination thereof. For example, in operation 502, the method 200 can involve adjusting the modified coordinates that were mapped for the target objects in operation 208. The 3D coordinate map of the 3D target model can include validation points and/or non-validation points. Non-validation points can be points of the 3D coordinate map that did not undergo fit compliance validation analysis in operation 210. The 3D target coordinate map validation and/or non-validation points can be adjusted to better fit the target objects. Additionally or alternatively, operation 502 can involve adjusting coordinate points of the 3D target model unaffiliated with the 3D target coordinate map. These unaffiliated coordinate points can likewise correspond to validation and/or non-validation points.

The validation and/or non-validation points of the 3D target model can correspond to geometric and/or non-geometric parameters of the 3D target model. The geometric parameters can be any observable, measureable, derivable, and/or detectable feature of the 3D target model, for example, dimensions, boundaries, edges, points, lines, points of inner surfaces, points of inner edges, points of outer surfaces, points of outer edges, points of target interiors, surface areas, and volumes. The points of the 3D target model can be 2D or 3D points (e.g., 2D or 3D Cartesian coordinate points). The 3D target model lines and surfaces can be mathematical equations. The 3D target model lines and surfaces can be represented as a group of points. The non-geometric target object parameters can correspond to, for example, the non-dimension based fit accuracy parameters (e.g., pressures, expected moisture).

The validation points marked for adjustment in operation 210 can be adjusted in operation 502 using one or more adjustment techniques, for example, computer vision, statistical learning, deep learning, differential geometry, mathematical topology, user input, or any combination thereof, including, for example, feature detection, feature extraction, object detection, object recognition, edge detection, context-based image classification, pose estimation, 3D reconstruction, photogrammetry. One or more non-validation points can be adjusted using such techniques. The validation points marked for adjustment can be manually and/or automatically adjusted based on visual and/or mathematical data of the 3D target model, the digital representations of the target objects, the computed geometric design definition (e.g., the fit accuracy parameters, the 3D target coordinate map, the geometric constructs of the 3D target model), or any combination thereof.

For example, a 2D or 3D rendering of the 3D target model with marked validation points can be overlaid on the digital representations of the target objects. The marked points can be adjusted to better fit the fit accuracy parameters associated with the geometric design definition, threshold validation thresholds, or any combination thereof, using visual and/or mathematical data of the 3D target model and/or the target object. The overlaid renderings can be scaled to have the same scale or to have sizes proportionate to one another (e.g., scaled to their actual size, less than their actual size, or larger than their actual size) and can be viewed on any modern computing device including, for example, a desktop computer, a laptop computer, a tablet computing device, a smartphone computing device, a network of one or more computing systems which can be accessed over internet-based networks, or any combination thereof.

Validation and/or non-validation points can be adjusted independently from one another and/or together. For example, validation points can be adjusted independently from non-validation points. Non-validation points can be adjusted independently from validation points. Adjustment of any coordinate point (e.g., validation point, non-validation point) can affect one or more other coordinate points of the 3D target model in operation 502. In this way, the 3D target model coordinate points can be actively and/or passively adjusted, where an active adjustment does not depend on an adjustment of one or more other coordinate points (but may or may not affect the adjustment of one or more other coordinate points), and where a passive adjustment depends on an adjustment of one or more other coordinate points. For example, adjusting validation points in a first region can also result in a passive adjustment of other validation points in the first region, of non-validation points in the first region, and/or other coordinate points (e.g., validation and/or non-validation points) in one or multiple other regions. The other regions can be adjacent to (e.g., immediately next to) the first region and/or can be separated from the first region by a gap or another region of the 3D target model.

When 3D target model coordinate points are adjusted, they can be displaced along one or multiple paths, for example, between an initial unadjusted position to a final adjusted positioned. One or more intermediate adjusted positions can be between the initial and final positions. The displacement paths of the points can be curved, straight, include polyline paths (e.g., two or more straight and/or curved paths, for example, a zig-zag, or any combination thereof. The displacement paths can be angled to one another. For example, a validation point can have an initial unadjusted position, a first adjusted position, and a second adjusted position in operation 502. The path between the initial unadjusted position and the first adjusted position can be the same or different as the path between the first adjusted position and the second adjusted position. The adjustment of validation and/or non-validation points can be dependent on one another for example, based on one or more of the fit accuracy parameters.

The system 100 can link (also referred to as digitally associate) two or more points together in a group so that an adjustment of one or more first points in the group can affect the coordinate position of one or more second points in the group. Point linking can advantageously reduce processing time and make the adjustment process of the 3D target model and/or of the coordinate mapping of the 3D target model in operation 502 faster (e.g., relative to without point linking).

Two or more points can be rigidly linked together (e.g., distance between them is associated with a ratio) and/or flexibly linked together (e.g., distance between them is within a range). For example, a first point can be rigidly linked to a second point and flexibly linked to a third point, and the second and third points can be rigidly or flexibly linked together. For the rigidly linked first and second points, an adjustment of the first point can result in a corresponding adjustment of the second point. The adjustment of the second point relative to the first point can be a function of a displacement ratio, where the first point:second point displacement ratio can be 0.1:1.0 to 10.0:1.0 and/or 1.0:0.1 to 1:10.0, including every 0.1 increment within these ranges. For example, for a 1:1 displacement ratio, if the first point is displaced by 1.0 mm, then the second point is displaced by 1.0 mm. For flexibly linked first and second points, an adjustment of the first point can result in adjustment of the second point after a threshold displacement of the first point has been exceeded, after which the second point can be displaced relative to the remaining displacement that the first point undergoes, for example, according to the displacement ratio described above. The threshold displacement can range from about 0.1 mm to about 10.0 mm, including every 0.1 mm increment within this range. For example, for a 2.0 mm threshold displacement and a 1:1 displacement ratio, if the first point is displaced by 3.0 mm, then the second point is displaced by 1.0 mm.

Linked points can be displaced along the same or different vectors, for example, collinear vectors, parallel vectors, opposite vectors, angled vectors, or any combination thereof, where the angle between angled vectors can be from 1 degree to about 180 degrees, including every 1 degree increment within this range. Linked points can be displaced with a combination of displacements, for example, in 2D or 3D space. For example, linked points can be displaced in the same direction or different directions relative to one another.

FIG. 5 further illustrates that the adjustment operation can involve adjusting the 3D geometry of the 3D target model in operation 504, also referred to as the 3D target model geometric constructs and geometric features. For example, geometric features affected and/or unaffected by the coordinate points adjusted in 502 can be adjusted in operation 504. 3D target model geometric constructs can be manually and/or automatically adjusted based on visual and/or mathematical data of the 3D target model, the digital representations of the target objects, the other components of the computed geometric design definition (e.g., the fit accuracy parameters, the 3D target coordinate map), adjusted coordinate points (e.g., adjusted validation and/or non-validation points), or any combination thereof. 3D target model geometric constructs can include, for example, points (e.g., 2D points, 3D points), lines, polylines, arcs, polyarcs, polynomial splines, ellipse arc splines, curves, bezier curves, free-form points, free-form lines, free-form arcs, free-form curves, nurbs curves, nurbs surfaces, extruding, lofting, sweeping, revolving, extruding along a curve, sweeping along a curve, lofting curves, lofting surfaces, extruding along a surface, surfaces (e.g., flat, curved, parametric, non-parametric), 2D shapes (e.g., circles, ellipses, triangles, stadiums, squares, rectangles, polygons), 3D shapes, solids, volumes, or any combination thereof. Such 3D target model constructs can be affected by the adjustments made to the 3D target model and/or to the 3D target coordinate map in operation 502.

A 3D target model geometric feature can be considered affected by an adjustment in operation 502 if it is within a proximity threshold of an adjustment point. A geometric feature can be considered unaffected by an adjustment in operation 502 if it is outside a proximity threshold of an adjustment point. The proximity threshold can be, for example, from about 0.1 mm to about 50 mm, including every 0.1 mm increment within this range. In this way, adjusting coordinate points in operation 502 can also result in an adjustment one or multiple geometric features operation 504. An affected geometric feature can be directly or indirectly associated with the one or more coordinate points which affects the geometric feature. Geometric features are directly associated with a coordinate point where the coordinate point is on or within the geometric feature. Geometric features are indirectly associated with a coordinate point where the coordinate point is not on or within the geometric feature, but where an adjustment of another coordinate point creates a ripple effect through the coordinate mapping and/or one or more geometric features that ultimately affects a coordinate point that is directly associated with the geometric feature. Geometric features of the 3D target model can be adjusted in operation 212, for example, in operations 502 and 504. For example, a 2D or 3D rendering of this generated 3D target model can be overlaid upon the digital representations of the target objects having adjusted coordinate points. The geometric features can be manually and/or automatically adjusted based on visual and/or mathematical data of the 3D target model, the digital representations of the target objects, the computed geometric design definition (e.g., the fit accuracy parameters, the 3D target reference map), adjusted coordinate points (e.g., adjusted validation and/or non-validation points), or any combination thereof.

Additionally or alternatively, operation 504 can involve modifying the geometric constructs of the 3D target model to conform to or otherwise adopt the adjustments made in operation 502.

The coordinate mapping adjustments and/or the geometric feature adjustments can be used as inputs to generate an adjusted 3D target model in operation 208. For example, as indicated by arrow 506, FIG. 5 illustrates that the 3D target model can be generated by computing the geometric design definition of the 3D reference model with an adjusted 3D coordinate map and/or with an adjusted 3D geometry for the target objects. Additionally or alternatively, as indicated by arrow 508, FIG. 5 illustrates that the 3D target model generated with the adjusted coordinate mapping and/or adjusted 3D geometry can be validated in operation 210. However, operations 208 and/or 210 can receive any output from operation 212, for example, the adjusted 3D coordinate map output from operation 502 and/or the adjusted 3D geometric feature output from operation 504.

The modified 3D coordinate map between the 3D reference model and the target objects can be adjusted in operation 212 in accordance with the fit accuracy requirements of the 3D reference model design and the target objects, for example, with the coordinate points adjusted in operation 502 and/or with the geometric features adjusted in operation 504. A new 3D target model can be generated with the adjustments made in operation 212 (e.g., the adjusted 3D coordinate map and/or the adjusted geometric features).

The geometry of the generated 3D target model can be modified (e.g., operation 208) and/or adjusted (e.g., operation 212) in accordance with the fit accuracy parameters of the 3D reference model design and the target objects. As another example, the geometry of the generated 3D target model can be modified (e.g., operation 208) and/or adjusted (e.g., operation 212) according to the targets objects and the fit accuracy parameters of the 3D reference model design definition. As yet another example, the mathematical geometric design definition of the 3D reference model and/or of the 3D target model can be modified according to the geometric features of the target objects and/or the fit accuracy requirements of the 3D reference model design. As described above, adjustments in operation 212 can involve computer vision, statistical learning, deep learning, differential geometry, mathematical topology, human input, or any combination thereof.

The method 200 can involve performing operations 208, 210, 212, and/or 214 one or multiple times. For example, the generation, validation, adjustment and/or improvement operations 208, 210, 212, 214 can be repeatedly iterated (also referred to as cycled through and repeated) until the 3D target model fits the target object in accordance with the fit accuracy parameters. For example, operations 208, 210, 212 and/or 214 can be iterated until the threshold validation thresholds are satisfied. As an example, each iteration can involve executing (1) operations 208-210-212 (e.g., first executions 208i-210i-212i, followed by one or more subsequent executions: 208ii-210ii-212ii . . . 208N-210N-212N, where N can be from 2 to 100 or more, including every 1 execution increment within this range); (2) operations 210-212 (e.g., first execution 208i-210i-212i, followed by one or more subsequent executions: 210ii-212ii . . . 210N-212N, where N can be from 2 to 100 or more, including every 1 iteration increment within this range), or any combination thereof, such that the iteration through the operations can include generating a subsequent 3D target model in operation 208 according to execution pattern (1) and/or can include bypassing operation 208 after operation 212 such that the output from the adjustment operation 212 (e.g., steps 502 and/or 504) can be input into the validation operation 210 in execution pattern (2). Each iteration can include operations 502 and/or 504. Each iteration can include process paths 506 and/or 508.

FIG. 5 further illustrates that the generated 3D target models validated in operation 210 can be used as improved 3D target models in operation 214. As described above, until the rendering of the generated 3D target model meets (also referred to as satisfies) the fit accuracy requirements of the 3D reference model design with respect to the target object, steps 208, 210, and/or 212 can be repeated.

Figure 6:
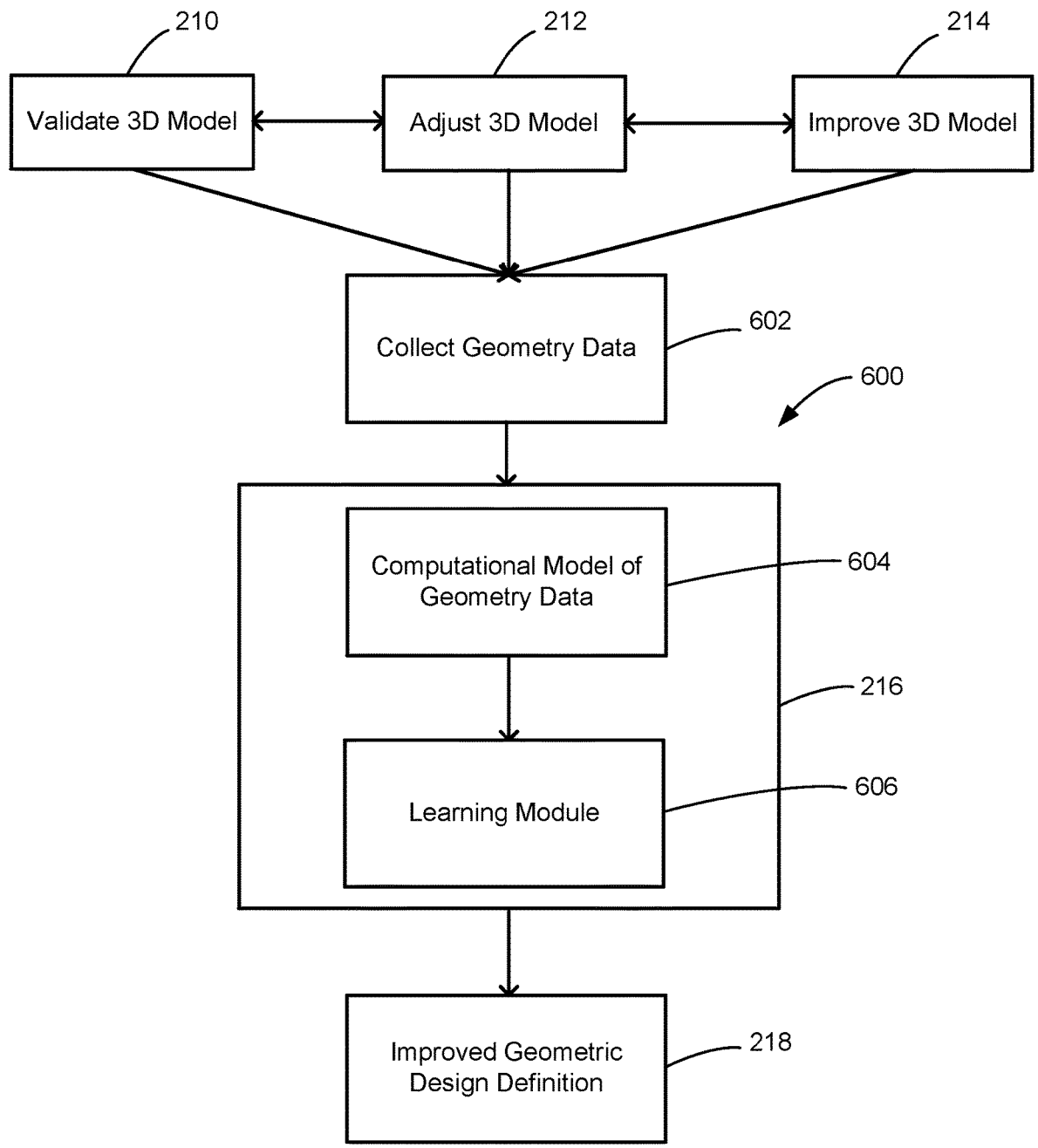
FIG. 6 illustrates a variation of a method undertaken by the system.

FIG. 6 illustrates a variation of a method 600 of processing data from the method 200, for example, from validating operation 210, from adjusting operation 212, from improving operation 214, or any combination thereof. Although not shown in FIG. 6, the method 600 can include processing data from any of the operations of method 200, including, for example, operations 202, 204, 206, 208, 210, 212, 214, 216, 304, 306, 402, 404, 502, 504, or any combination thereof, including any of the operations not explicitly listed (e.g., operations illustrated, described, and/or contemplated herein). The process 600 can be a sub-routine of method 200, can be part of method 200, and/or can be a standalone process.

FIG. 6 illustrates that in operation 602 the data (e.g., geometry data) from the validating, adjusting and/or improving operations 210, 212, 214 can be collected and stored in a database (e.g., memory 110, database 114) after each iteration of operations 210, 212, and/or 214. This data can be referred to as validation data, adjustment data, and improvement data, respectively. The geometry data can include the visual, mathematical and/or descriptive representations of the geometric design definition (e.g., the accuracy fit parameters, the 3D reference coordinate map, the 3D reference model geometric constructs), computed geometric design definitions (e.g., the fit accuracy requirements, the 3D reference and/or target coordinate maps, the 3D target model geometric constructs), the 3D reference models, the 3D target models, the reference objects, the target objects, or any combination thereof. For example, the geometry data can include the 3D coordinate mappings created. For example, the 3D coordinate mapping data can include the 3D reference coordinate mappings associated with the one or more reference objects, the 3D modified coordinate mappings associated with the target objects (e.g., generated in operation 208), the 3D adjusted coordinate mappings associated with the target objects (e.g., generated in operation 212), or any combination thereof. The geometry data can include the validation and/or non-validation points. The geometry data can include the adjustments made in operation 212, for example, the displacements and/or vectors of the coordinate points and/or the geometry features affected and/or unaffected by coordinate mapping changes. The vectors can have the direction and magnitude of each change to the 3D target model. The data can collected can be represented visually, mathematically, descriptively, or any combination thereof, where a descriptive representation can correspond to a non-mathematical description. The data collected can be represented as vector fields and/or as matrices.

FIG. 6 illustrates that in operation 218 the geometric design definition improved in operation 216 (e.g., operation 604 and/or 606) can be used in method 200 to determine 3D reference models and 3D target models.

Improving the geometric design definition can involve iteratively improving the fit of the geometric design definition of 3D reference models (also referred to as the reference geometric design definition) according to the fit accuracy parameters of the corresponding 3D reference model using, for example, the geometry data collected during the validating, adjusting and improving operations 208, 210, 212. Improving the geometric design definition can involve iteratively improving the fit of the geometric design definition of 3D target models (also referred to as the target geometric design definitions) according to the fit accuracy parameters of the corresponding 3D reference and/or target model using, for example, the geometry data collected during the validating, adjusting and improving operations 208, 210, 212, 214.

The method 600 can further involve representing the geometric design definition as computational data models in operation 604.

The method 600 can further involve applying one or more learning methods (also referred to as learning modules) to the computational data models of the geometric design definition and to the data collected during the validating, adjusting and improving operations 210, 212, 214 to iteratively improve the fit of the 3D reference models and/or of the generated 3D target models in operation 606. For example, operation 606 can involve applying learning methods to the computational data models of the geometric design definitions and to the data collected during the validating, adjusting and improving operations 210, 212, 214. The learning methods can include machine learning, online machine learning, online learning, or any combination thereof. For example, operation 606 can use supervised and/or unsupervised online learning with machine learning techniques such as computer vision, statistical learning, deep learning, differential geometry, mathematical topology, natural language processing, including, regression, Markov models, support vector machines, Bayes Classifier, clustering, decision trees, neural networks, or any combination thereof. The system 100 can use such learning algorithms to iteratively improve the estimation and/or determination of 3D coordinate maps (e.g., the 3D reference coordinate map, the 3D target coordinate map). The system 100 can use such learning algorithms to iteratively improve the geometric design definition such that operations 208, 210, and/or 212 can be executed 1 to 10 times before a generated 3D target model is validated, including every 1 execution within this range. For example, the system 100 can use such learning algorithms so that the first 3D target model generated is validated in operation 210 (e.g., perfect fits the target object) without the need for any subsequent iterations.

As described above, methods are disclosed for validating, adjusting, and improving the fit of the generated 3D target models to the target objects that they are generated to fit. The geometry data can be collected in operation 602 before, during, and/or after each time that the 3D target model is improved, for example before, during, and/or after operations 210, 212, and/or 214. The geometry data collected can be received by one or more learning modules in operation 606. The computational data models of the geometric design definitions can also be received by the learning methods in operation 606. The learning methods (e.g., machine learning, online machine learning, online learning) can use, for example, statistical, probabilistic, and/or deep learning techniques to learn from the differences between the geometry of the 3D target and/or reference models to dynamically modify the computational data model that represents the geometric design definition of the 3D reference model to better fit the target objects with respect to the fit accuracy requirements of the 3D reference model design. For example, the online machine learning can include the learning methods in operations 216 and 606. For example, the learning methods can learn the differences between the geometry of one or more of the following: the generated 3D target models (e.g., created in operation 208); the adjusted 3D target models (e.g., created in operation 208 based at least partly on the adjustments determined in operation 212); the improved 3D target model (e.g., validated in operation 210); the 3D reference model (e.g., created in operation 204); or any combination thereof.

The geometric design definition can be iteratively improved by executing operations 602, 604, and/or 606 one or multiple times. For example, operations 602, 604, and/or 606 can be used to iteratively improve the fit of the geometric design definition to one or multiple reference objects.

The operations illustrated in FIGS. 1-6 can be executed and repeated in any order and in any pattern.

The operations 202, 204, 206, 208, 210, 212, 214, and 216 can be interchangeably combined, rearranged, substituted, and/or omitted in any combination, and can be executed in any order, for example, in the order shown in FIG. 2. Additional operations that are not shown can be added to the method 200 or can be part of a separate implementable and/or performable method, for example, determining fit accuracy parameters, creating 3D coordinate maps, defining geometric constructs of the geometric design definition, adjusting fit accuracy parameters, adjusting 3D coordinate maps, adjusting geometric constructs of the geometric design definition, iteratively computing geometric design definitions, iteratively computing adjusted geometric design definitions, or any combination thereof, as well as any other process or operation described or contemplated herein.

Figure 7A:
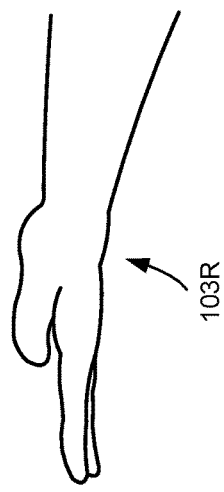
FIG. 7A illustrates a variation of a digital representation of a top view of a reference object.
Figure 7B:
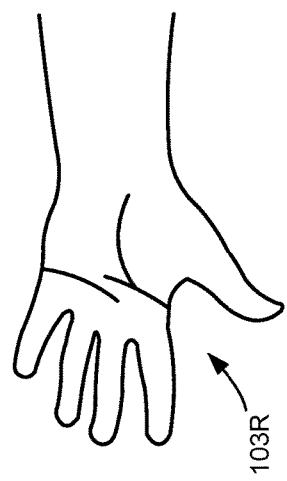
FIG. 7B illustrates a variation of a digital representation of a bottom view of the reference object of FIG. 7A.
Figure 7C:
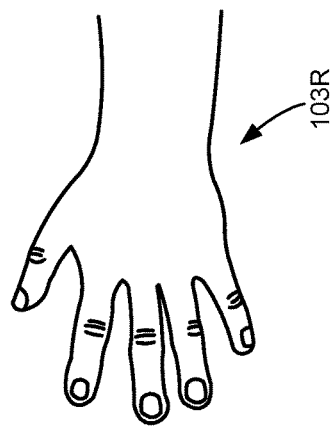
FIG. 7C illustrates a variation of a digital representation of a side view of the reference object of FIG. 7A.

FIGS. 7A-7C illustrate exemplary views of a variation of a reference object 103R. FIGS. 7A-7C illustrate that the reference object 103R can be a partial view of a person's body, for example, a left hand, a left wrist, and a portion of the left forearm. The reference object 103R can be the left hand, the left wrist, the portion of the left forearm in the figure, or any combination thereof. For example, the left wrist can be identified as the reference object 103R in operation 202. FIGS. 7A, 7B, and/or 7C each illustrate that the system 100 can identify a physical reference object 103R (e.g., a physical human wrist) upon which one or more geometric design definitions of 3D reference models can be designed to fit. The images in FIGS. 7A-7C can be captured with a data acquisition device 102. For example, the images in FIGS. 7A-7C can be 2D photographs captured with a camera (e.g., an 8 megapixel digital camera). The images in FIGS. 7A-7C can be digital representations of the physical object in the images. FIGS. 7A-7C illustrate that first, second and third views can be, for example, top, bottom and side views, respectively. The reference object 103R can be a male or female reference object.

FIGS. 8A-8C illustrate a variation of a 3D coordinate map 700 applied to the reference object 103R (e.g., left wrist) of FIGS. 7A-7C. The coordinate map 700 can be represented in 2D or 3D digital and/or physical space. The coordinate map can be visually and/or mathematically represented. For example, FIGS. 8A-8C illustrate variations of 2D visual digital representations of a variation of the coordinate map 700, as shown by the points 702 (represented as dots).

The 3D coordinate map (e.g., map 700) can include multiple points 702 (also referred to as markers) that represent the geometric relationship between the reference object 103R and the 3D reference model (not shown) designed to fit the reference object. As described above, the map 700 can include, for example, 2 markers to 1,000,000 or more markers, including every 1 marker increment within this range, as well as every 1,000 marker range within this range (e.g., 2-1002 markers, 1002-2002 markers . . . 999,002-1,000,000 markers). For example, FIG. 8A illustrates that 8 points 702 can be mapped onto the top view of the reference object 103R, FIG. 8B illustrates that 8 points 702 can be mapped onto the bottom view of the reference object 103R, and FIG. 8C illustrates that 6 points 702 can be mapped onto the side view of the reference object 103R. The points 702 can correspond to validation and/or non-validation points. The points 702 represent the 3D coordinate map between the reference object 103R and the 3D reference model to be created. The points 702 of the coordinate map 700 can correspond to points of an orthosis, prosthesis, and/or implant, non-medical device, non-medical structure, or any combination thereof. For example, the points 702 in FIGS. 8A-8C can correspond to a bracelet (also referred to as a wristband). The bracelet can be a fashion bracelet, a medical bracelet, a fashion bracelet with medical information inscribed on it, or any combination thereof.

FIG. 9A illustrates a close-up view of the 3D coordinate map 700 of FIG. 8A at section 9A-9A.

FIG. 9B illustrates a close-up view of the 3D coordinate map 700 of FIG. 8B at section 9B-9B.

FIG. 9C illustrates a close-up view of the 3D coordinate map 700 of FIG. 8C at section 9C-9C.

Figure 10C:
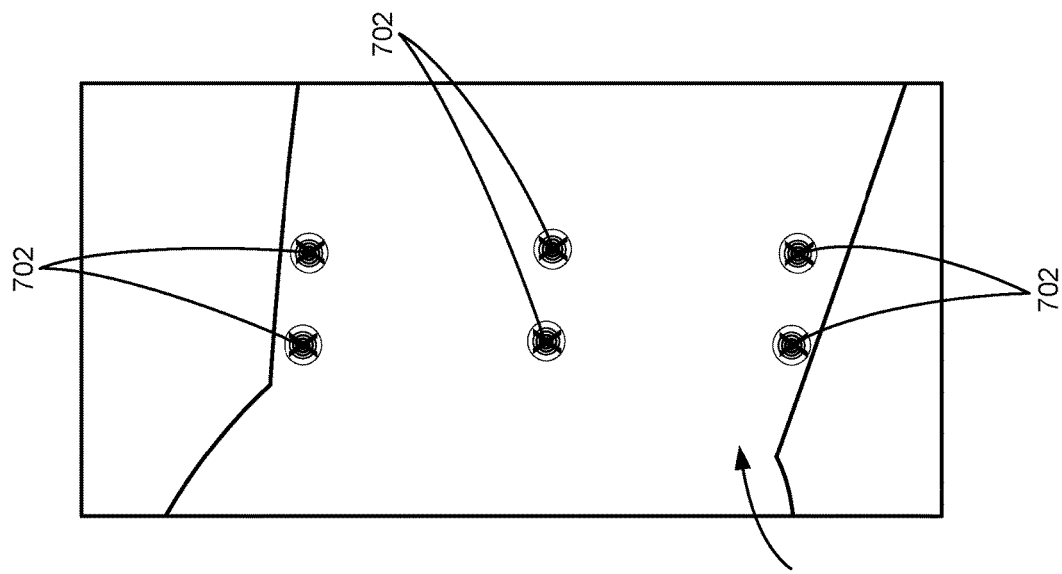
FIG. 10C is a view of FIG. 9C with the coordinate map marked as "X's."
Figure 10B:
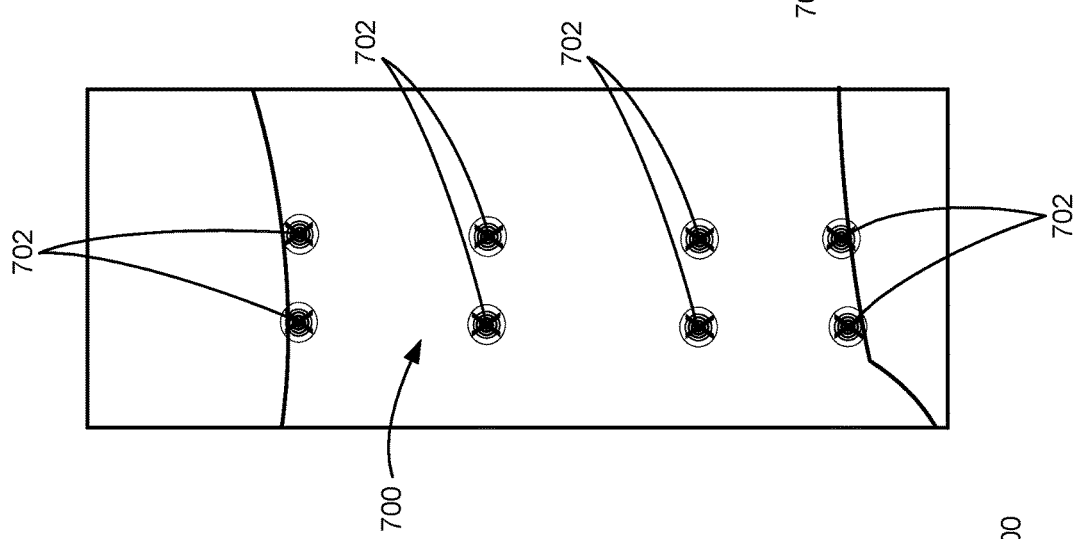
FIG. 10B is a view of FIG. 9B with the coordinate map marked as "X's."
Figure 10A:
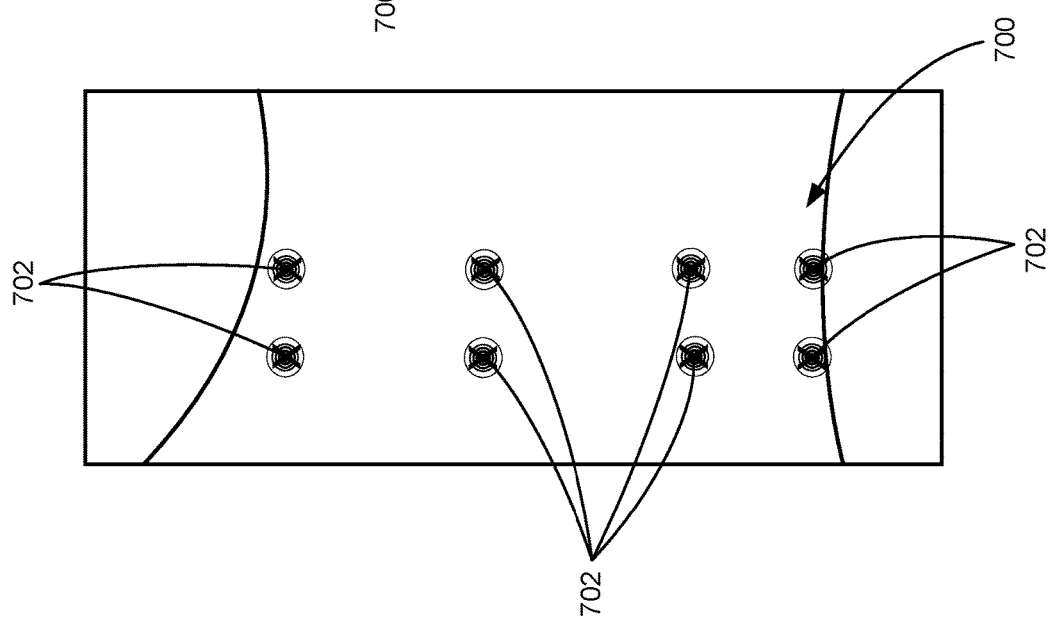
FIG. 10A is a view of FIG. 9A with the coordinate map marked as "X's."

FIG. 10A illustrates the points 702 of the 3D coordinate map 700 of FIGS. 8A and 9A as "X's."

FIG. 10B illustrates the points 702 of the 3D coordinate map 700 of FIGS. 8B and 9B as "X's."

FIG. 10C illustrates the points 702 of the 3D coordinate map 700 of FIGS. 8C and 9C as "X's."

Figures 11A, 11B, 11C:
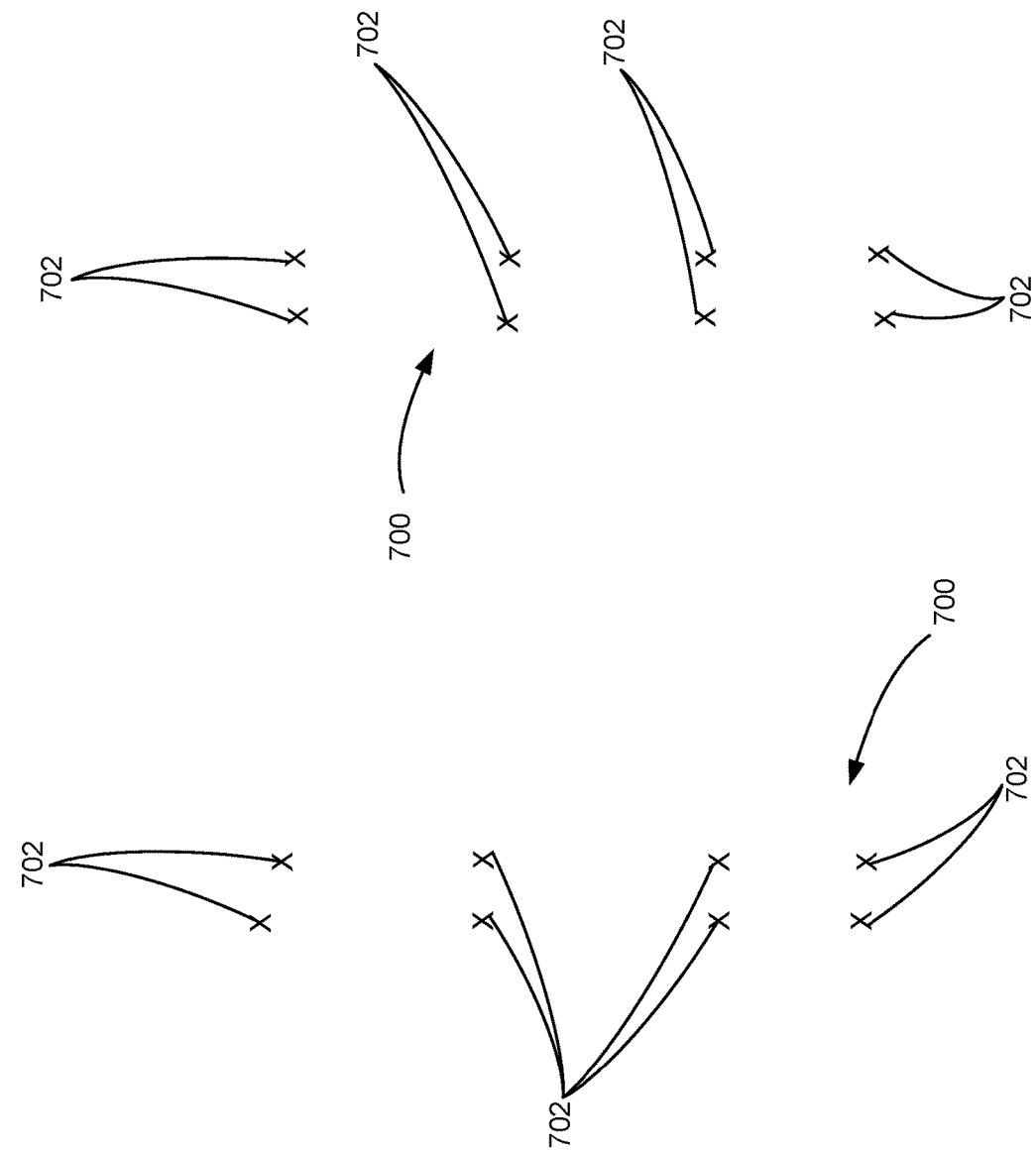
FIG. 11A is a variation of the 3D coordinate map of FIGS. 9A and 10A stripped from the digital representation of the reference object.
FIG. 11B is a variation of the 3D coordinate map of FIGS. 9B and 10B stripped from the digital representation of the reference object.
FIG. 11C is a variation of the 3D coordinate map of FIGS. 9C and 10C stripped from the digital representation of the reference object.

FIG. 11A illustrates the 3D coordinate map 700 of FIG. 10A with the points 702 isolated from the digital image of the reference object 103R.

FIG. 11B illustrates the 3D coordinate map 700 of FIG. 10B with the points 702 isolated from the digital image of the reference object 103R.

FIG. 11C illustrates the 3D coordinate map 700 of FIG. 10C with the points 702 isolated from the digital image of the reference object 103R.

The point density in FIGS. 11A-11C can be 0-2 points per 100 mm$^2$.

The coordinate mapping 700 can have more or less points 702 than shown in FIGS. 8A-11C and/or can have a greater or lesser point density, for example, per 100 mm$^2$.

Figure 12C:
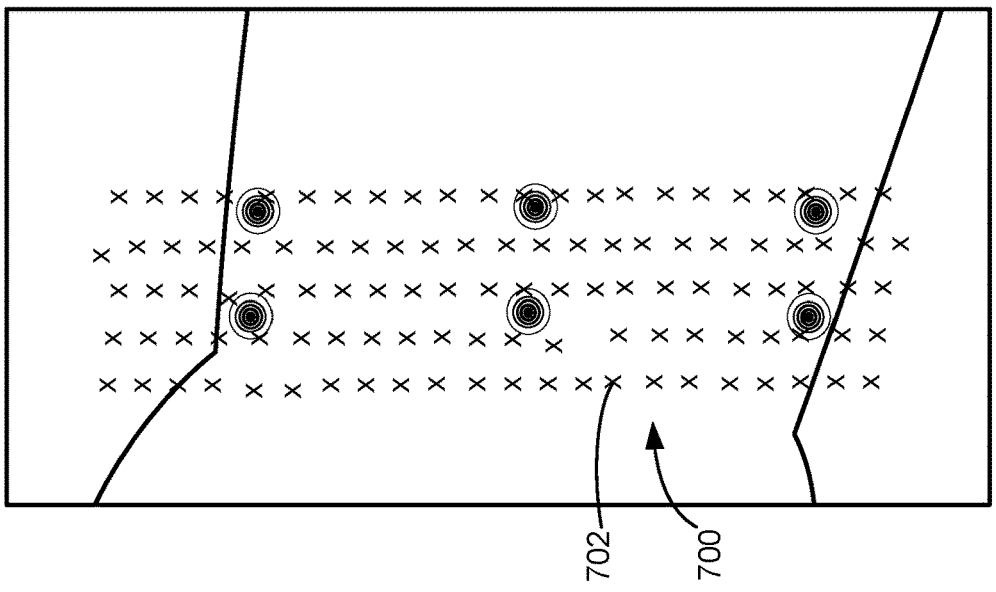
FIG. 12C illustrates a variation of a 3D coordinate map applied to the digital representation of FIG. 7C at section 9C-9C of FIG. 8C.
Figure 12B:
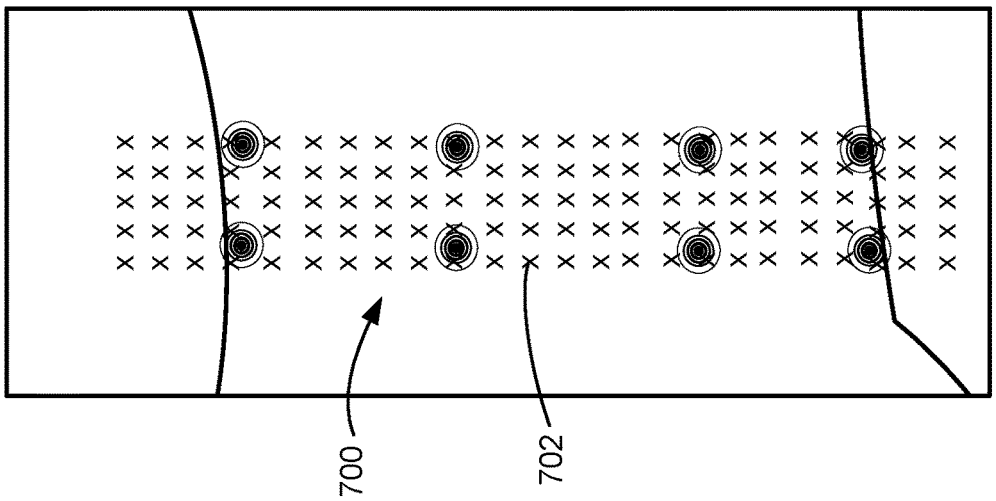
FIG. 12B illustrates a variation of a 3D coordinate map applied to the digital representation of FIG. 7B at section 9B-9B of FIG. 8B.
Figure 12A:
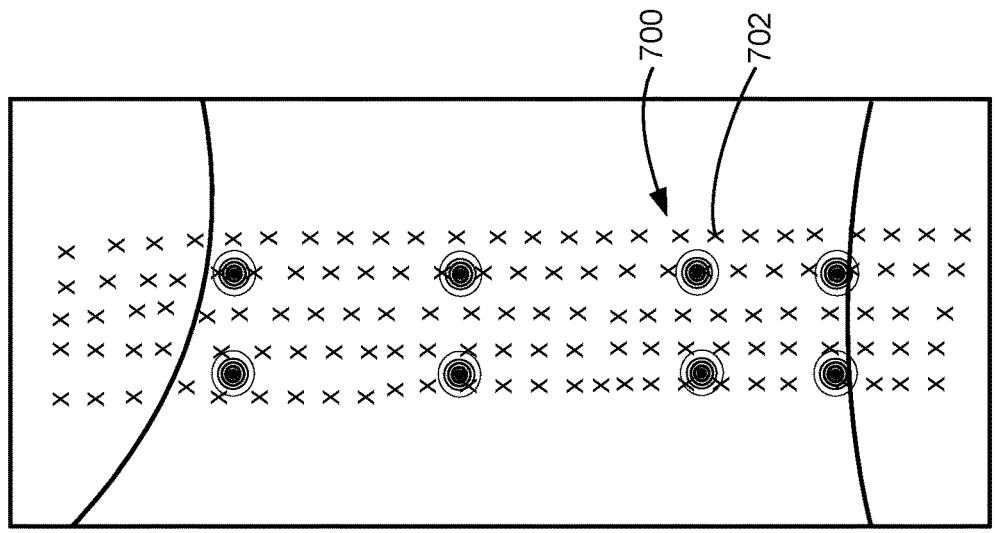
FIG. 12A illustrates a variation of a 3D coordinate map applied to the digital representation of FIG. 7A at section 9A-9A of FIG. 8A.

For example, FIGS. 12A-12C illustrate that the mapping 700 can comprise a greater number of points 702 and a greater point density relative to FIGS. 8A-11C. FIGS. 12A-12C illustrate that the density of the points 702 can be from 1 to 30 points per 100 mm$^2$. The coordinate mappings 700 in FIGS. 12A-12C can produce the same fit as or a different fit than the coordinate mappings 700 in FIGS. 8A-11C.

The distribution of the points 702 can be the same or different for other target objects (not shown).

As discussed above, the placement of the 3D reference points 702 can depend on the fit accuracy parameters determined in operation 402, the geometric features of the reference object, user input, or any combination thereof.

FIG. 13A illustrates the 3D coordinate map 700 of FIG. 12A with the points 702 isolated from the digital image of the reference object 103R.

FIG. 13B illustrates the 3D coordinate map 700 of FIG. 12B with the points 702 isolated from the digital image of the reference object 103R.

FIG. 13C illustrates the 3D coordinate map 700 of FIG. 12C with the points 702 isolated from the digital image of the reference object 103R.

FIGS. 14A$_1$-14C$_4$ illustrate variations of a process for creating digital visual representations of the geometric design definition for a reference object (e.g., reference object 103R) for one or more of the views acquired of the reference object (e.g., of each of the views acquired). The digital visual representations of the geometric design definition are also referred to as the 3D reference model. For example, FIGS. 14A$_1$-14A$_4$, FIGS. 14B$_1$-14B$_4$, and FIGS. 14C$_1$-14C$_4$ each illustrate a variation of a process of designing a 3D reference model to fit the reference object 103R digitally represented in FIG. 14A$_1$, FIG. 14B$_1$, and FIG. 14C$_1$, respectively, including: determining a 3D coordinate map 700 (e.g., in operation 204) and applying the map 700 to the reference object 103R (FIGS. 14A$_1$, 14B$_1$, and 14C$_1$); stripping the digital images of the reference object 103R from the coordinate mappings 700 (FIGS. 14A$_2$, 14B$_2$, and 14C$_2$); creating a 3D reference model lattice 1402 (also referred to as lattice structure) based at least partly on the 3D coordinate map 700 (FIGS. 14A$_3$, 14B$_3$, and 14C$_3$); creating a 3D reference model 1404 at least partly based on the 3D coordinate map 700 and/or the lattice 1402 (FIGS. 14A$_4$, 14B$_4$, and 14C$_4$); or any combination thereof. The intersecting first and second perpendicular lines in each of FIGS. 14A$_2$-14C$_4$ can be quadrant axes. This example does not limit the present disclosure in any way to wristbands or the particular order of these steps as listed. For example, these steps can be performed in any order or one or more steps can be omitted or added. As another example, these steps can be used to create 3D reference models 1404 of any structure, including 3D reference models of orthoses, prostheses, implants, non-medical devices, non-medical structures, or any combination thereof.

FIGS. 15A-15C illustrate exemplary views of a variation of a target object 103T. FIGS. 15A-15C illustrate that the target object 103T can be a partial view of a person's body, for example, a right hand, a right wrist, and a portion of the right forearm. The target object 103T can be the right hand, the right wrist, the portion of the right forearm in the figure, or any combination thereof. For example, the right wrist can be identified as the target object 103T in operation 206. FIGS. 15A, 15B, and/or 15C each illustrate that the system 100 can identify a physical target object 103T (e.g., a physical human wrist) for which one or more geometric design definitions of 3D reference models can be computed to generate a 3D target model, for example, in operation 208. The images in FIGS. 15A-15C can be captured with a data acquisition device 102. For example, the images in FIGS. 15A-15C can be 2D photographs captured with a camera (e.g., an 8 megapixel digital camera). The images in FIGS. 15A-15C can be digital representations of the physical object in the images. FIGS. 15A-15C illustrate that first, second and third views can be, for example, top, bottom and side views, respectively. The target object 103T can be a male or female target object.

FIGS. 15A-15C illustrate that the target object 103T (e.g., a right wrist) can have the same or similar isomorphic topology as the reference object 103R (e.g., a left wrist). For example, reference and target objects 103R, 103T on the same side of the respective subjects from which they are imaged can have the same isomorphic topology as one another, such as, for example, a left side of a first reference object (e.g., a left limb, a left joint) and a left side of a first subject (e.g., a left limb, a left joint). As another example, reference and target objects 103R, 103T on opposite sides of the respective subjects from which they are imaged can have a similar isomorphic topology as one another, such as, for example, a left side of a first subject (e.g., a left limb, a left joint) and a right side of a second subject (e.g., a right limb, a left joint). The subjects having the reference and target objects 103R, 103T can be the same or a different age and/or gender from one another.

FIG. 16A-16C illustrate a variation of a generated 3D target model 1604 designed to fit a target object 103T. The 3D target model 1604 can be generated, for example, in operation 208. The generated 3D target model 1604 can be the initial 3D model generated using method 200, or can be any subsequent modification of an initial generated target model, for example, using operations 208, 210, and/or 212 until the 3D target model generated in operation 208 is validated in operation 210. For example, a subsequent iteration of an initial 3D target model can be an adjusted 3D target model generated in operation 208 with one or more adjustments from operation 212. Subsequent iterations of 3D target models generated in operation 208 can be generated with the adjustments identified in operation 212. The initial 3D target model or any subsequent iteration of the initial 3D target model can be validated in operation in operation 210. The improved 3D target model used in operation 214 can be any validated 3D target model, for example, the initial 3D target model and/or any adjusted 3D target model that has been validated. The initial 3D target model can be validated without any adjustments from operation 212. Where the initial 3D target model is adjusted, any subsequently generated 3D target model in operation 208 can be validated in operation 210, for example, with the adjustments identified in operation 212. Adjusted 3D target models that have been validated in operation 210 are also referred to as improved 3D models in operation 216.

The 3D target model 1604 can be any 3D target model in the process, including a not-yet-validated 3D target model, a validated 3D target model, or any combination thereof.

The 3D target model 1604 can be an orthosis, prosthesis, and/or implant, non-medical device, non-medical structure, or any combination thereof. For example, the 3D target model in FIGS. 16A-16C can correspond to a bracelet. The bracelet can be a fashion bracelet, a medical bracelet, a fashion bracelet with medical information inscribed on it, or any combination thereof.

FIGS. $17A_1$-$17C_5$ illustrate variations of a process (e.g., method 200) for generating the 3D target model 1604 of FIGS. 16A-16C. For example, FIGS. $17A_1$-$17A_5$, FIGS. $17B_1$-$17B_5$, and FIGS. $17C_1$-$17C_5$ each illustrate a variation of a process of generating a 3D target model to fit the target object 103T digitally represented in FIG. $17A_1$, FIG. $17A_2$, and FIG. $17A_3$, respectively, including: overlaying a 3D reference model 1404 computed with a 3D reference coordinate map 700 (e.g., the 3D reference model 1404 computed with the 3D reference coordinate map 700 determined in FIGS. $14A_1$, $14A_2$, and $14A_3$) onto the target object 103T (FIGS. $17A_1$, $17B_1$, and $17C_1$); determining a 3D target coordinate map 700' by (e.g., in operation 208) and applying the modified 3D coordinate map 700' to the target object 103T (FIGS. $14A_1$, $14B_1$, and $14C_1$), where the modified 3D coordinate map 700' has coordinate points 702' marked as "O's"; stripping the digital images of the target object 103T from the coordinate mappings 700' (FIGS. $14A_3$, $14B_3$, and $14C_3$); creating a 3D target model lattice 1602 (also referred to as lattice structure) based at least partly on the 3D target coordinate map 700' (FIGS. $14A_4$, $14B_4$, and $14C_4$); creating a 3D target model 1604 at least partly based on the 3D coordinate map 700 and/or the lattice 1602 (FIGS. $14A_5$, $14B_5$, and $14C_5$); applying the generated 3D target model 1604 to the target object 103T (FIGS. 16A-16C); or any combination thereof. The generated 3D target models 1604 can be validated in operation 210 and/or adjusted in operation 214. The 3D target coordinate map 700' can be determined with or without overlaying 3D reference model data (e.g., 3D reference coordinate map 700) on the target object 103T.

The 3D target coordinate map 700' can be determined manually or via a computer by determining measurements and/or differences between one or more points of the 3D reference map and the target object, between one or more points of the geometric constructs of the 3D reference model and the target object, or any combination thereof. These measurements and differences can be estimated, for example, using computer vision, statistical learning, deep learning, differential geometry, mathematical topology, or any combination thereof, including, for example, feature detection, feature extraction, object detection, object recognition, edge detection, context-based image classification, pose estimation, 3D reconstruction, photogrammetry, or any combination thereof. The intersecting first and second perpendicular lines in each of FIGS. $17A_3$-$17C_5$ can be quadrant axes.

The example in FIGS. $17A_1$-$17C_5$ does not limit the present disclosure in any way to wristbands or the particular order of these steps as listed. For example, these steps can be performed in any order or one or more steps can be omitted or added. As another example, these steps can be used to create 3D target models 1604 of any structure, including 3D target models of orthoses, prostheses, implants, non-medical devices, non-medical structures, or any combination thereof.

FIG. 18A illustrates variation of the relative positions of the 3D reference and target coordinate maps 700, 700' (e.g., of FIGS. $17A_1$ and $17A_2$) applied to the target object 103T.

FIG. 18B illustrates that modification distances can be measured and/or estimated between each coordinate point 702 and a corresponding modified coordinate point 702'. The distances can range from about 0.0 mm to about 100.0 mm or more, including every 0.1 increment within this range and beyond, as the exact modification distance. The distances between two points (e.g., a 702-702' point pair) can be measured along 1, 2, and/or 3 axes (e.g., Cartesian coordinate axes X, Y, and/or Z). For example, FIG. 18B illustrates that the distances can be measured along a first axis 1800a. FIG. 18B illustrates that the 3D reference coordinate points $X_1$-$X_8$ can be modified by distances $D_1$-$D_8$ to create the 3D target coordinate points $O_1$-$O_8$, respectively. The distances $D_1$-$D_8$ can be the same or different from one another. For example, the distances $D_1$-$D_8$ can each range from about 0.0 mm to about 100.0 mm, including every 0.1 increment within this range. The distances $D_1$-$D_8$ can be determined manually by a person looking at overlay data (e.g., the overlay in FIG. $17A_1$) can be determined by a computer by analyzing overlay data (e.g., the overlay in FIG. $17A_1$), and/or can be estimated using machine learning based on a comparison between the geometry of the target and reference objects 103T, 103R relative to the 3D reference model (e.g., 1404) with or without analyzing overlay data (e.g., the overlay in FIG. $17A_1$).

FIG. 18C illustrates that the 3D reference coordinate points $X_1$, $X_3$, $X_5$, $X_7$ can be modified by distances $D_9$-$D_{12}$ along a second axis 1800b to create the 3D target coordinate points $O_1$, $O_3$, $O_5$, $O_7$, respectively. The 3D reference coordinate points $X_2$, $X_4$, $X_6$, $X_8$ and the 3D target coordinate points $O_2$, $O_4$, $O_6$, $O_8$ have been omitted from FIG. 18C for purposes of clarity. The first and second axes 1800a, 1800b can form an angle of about 1 degree to about 90 degrees relative to one another. For example, FIG. 18C illustrates that the first and second axes 1800a, 1800b can be perpendicular to one another. FIG. 18C can be a side view of FIG. 18A.

FIG. 18C further illustrates that the 3D reference coordinate points (e.g., points 702) can be modified to satisfy one or more of the fit accuracy parameters. For example, the 3D target coordinate points $O_1$, $O_3$, $O_5$, and $O_7$ can been moved from the reference point locations of coordinate points $X_1$, $X_3$, $X_5$ and $X_7$ to be a maximum and/or minimum distance 1804 from the surface of the target object 103T. The fit accuracy parameters 1804 can be the same or different as one another as described above (e.g., the exact dimension can correspond to the relative positions of the coordinate point and the target object).

FIG. 19 illustrates that a first fit accuracy parameter 1804a can be a maximum and/or minimum distance between a 3D reference model first surface 1404a (e.g., inner surface) and a reference object surface (e.g., outer surface) of the reference object 103R. FIG. 19 further illustrates that a second fit accuracy parameter 1804b can be a maximum and/or minimum distance between a 3D reference model second surface 1404b (e.g., outer surface) and a reference object surface 1902 (e.g., outer surface) of the reference object 103R. FIG. 19 further illustrates that a third fit accuracy parameter 1804b can be a maximum and/or minimum distance between a 3D reference model second surface 1404b (e.g., outer surface) and a reference object interior 1904 of the reference object 103R. FIG. 19 further illustrates that a fourth fit accuracy parameter 1804d (e.g., represented by compression arrow 1804d) can be a maximum and/or minimum pressure applied by the 3D reference model 1404 to the reference object 103R or configured to be applied by the 3D reference model 1404 to the reference object 103R, for example to the reference object surface 1902. FIG. 19 further illustrates that one or more sensors 152 can be digitally represented on the 3D reference and target models (e.g., sensor(s) 152 on the 3D reference model 1404 of FIG. 19).

FIGS. $20A_1$-$20C_{6X}$ illustrate a variation of using the method 200 to create a 3D target model to fit a target object. The 3D target model can be a shine brace. For example, FIGS. $20A_1$-$20A_6$, FIGS. $20B_1$-$20B_6$, and FIGS. $20A_1$-

$20C_{6X}$ illustrate back, front, and side views, respectively, of various steps of the method 200 that can be used to generate 3D target models.

FIGS. $20A_1$-$20C_1$ illustrate that a reference object 103R can be acquired using operation 202. The reference object 103R can be a leg.

FIGS. $20A_2$-$20C_2$ illustrate that a variation of a 3D reference coordinate map 700 can be created in operation 204 (e.g., using operation 404) and can be applied to the digital representation of the reference object 103R below the knee. The map 700 can have points 702 (represented as dots).

FIGS. $20A_3$-$20C_3$ illustrate that a variation of a 3D reference model lattice 1402 can be created (e.g., in operation 204) and can be applied to the digital representation of the reference object 103R. The lattice 1402 can be dependent on, for example, the 3D coordinate map 700, the fit accuracy parameters, user input, or any combination thereof. The lattice 1402 can conform to a surface of the lower leg 103R.

FIGS. $20A_4$-$20C_4$ illustrate that a target object 103T can be acquired using operation 206. For example, the target object 103T can be the crus of a leg between the knee and the ankle. FIG. $20C_{4X}$ illustrates that the method 200 (e.g., operation 206) can include acquiring one or more x-rays 2000 of the target object 103T. The x-rays 2000 can be used to identify pressure points 2002 (e.g., on or near bony protuberances). Additionally or alternatively, the x-rays 2000 can be used to position one or more sensors 152, for example, near or on pressure points 2002. For example, the sensor(s) 152 in FIG. $20C_{4X}$ can be one or more force sensors to measure impact forces against the lower leg (e.g., on the shin, for example, on a custom shin guard during a soccer game or on a custom cast while recovering from a bone break).

FIGS. $20A_5$-$20C_{5X}$ illustrate that a variation of a 3D target model 1604 can be created (e.g., in operation 208) and can be applied to the digital representation of the target object 103T. The 3D target model can be generated by computing the geometric design definition of the 3D reference model (not shown) with the 3D target coordinate map 700' having points 702'.

FIGS. $20A_6$-$20C_{6X}$ illustrate that an adjusted 3D target model 1604' can be created (e.g., in operation 210) and can be applied to the digital representation of the target object 103T (e.g., in operation 208 after the adjustment in operation 212). The 3D target model 1604 can be adjusted, for example, if the 3D target model is not validated in operation 210. For example, the 3D target coordinate map 700' can be adjusted to an adjusted 3D target coordinate map 700" having points 702" and/or the geometric constructs of the 3D target model 1604 can be adjusted (e.g., in 212). The adjusted 3D target model 1604' can be validated in operation 210 and/or be adjusted again in operation 214.

The 3D target coordinate maps 700' and 700" can be determined manually or via a computer by determining measurements and/or differences between one or more points of the 3D reference map and the target object, between one or more points of the geometric constructs of the 3D reference model and the target object, or any combination thereof. These measurements and differences can be estimated, for example, using computer vision, statistical learning, deep learning, differential geometry, mathematical topology, or any combination thereof, including, for example, feature detection, feature extraction, object detection, object recognition, edge detection, context-based image classification, pose estimation, 3D reconstruction, photogrammetry, or any combination thereof.

The points 702, 702 and 702 of 3D coordinate maps 700, 700', and 700", respectively are represented as "X's" in FIGS. $20A_1$-$20C_{6X}$.

The example in FIGS. $20A_1$-$20C_{6X}$ does not limit the present disclosure in any way to shin braces or the particular order of these steps as listed. For example, these steps can be performed in any order or one or more steps can be omitted or added. As another example, these steps can be used to create 3D target models 1604 and adjusted 3D target models 1604' of any structure, including 3D target models of orthoses, prostheses, implants, non-medical devices, non-medical structures, or any combination thereof.

FIG. 21 illustrates a variation of operation 208 in which the 3D target model (e.g., 1604) is generated for fit with or without also being designed to provide support to the target object. For example, operation 208 in FIG. 21 can be configured to generate a 3D target model for fit without any support aspect or medically corrective aspect to the fit. Operation 208 for fit only can be useful, for example, when designing fashion products (e.g., dresses, clothes, hats, wristbands) where providing support to the target object may not be desired. The 3D target model generated in operation 208 can by computing the geometric design definition determined in operation 204. FIG. 21 illustrates that the method 200 can further involve identifying pressure points on x-rays in operation 209a and generating 3D models for fit and correction in operation 209b. For example, after the 3D target model is generated for fit in operation 208, the pressure points (e.g., 2002) on the target object can be identified on the x-ray (e.g., 2000) in operation 209a. The 3D target model can be designed to apply force against the pressure points 2002 to provide support (e.g., corrective support) to the target object at the pressure points in 209b. The 3D target model generated by operation 209b can be generated independent of the 3D reference model. Additionally or alternatively, the geometric design definition can be re-computed in operation 209b when generating the 3D target model for fit and support. Operation 209b for fit and support can be useful, for example, when designing orthoses, prostheses, and/or implants (e.g., shin braces, scoliosis braces). The x-ray data can be acquired by a data acquisition device (e.g., device 102). The x-ray data can include x-rays of a subject without a manufactured 3D model (e.g., before or after first using the manufactured 3D model), x-rays of a subject wearing the manufactured 3D model, and/or x-rays after treatment using the manufactured 3D model has been successful. For example, the manufactured 3D model can be a brace or other support structure. The data from the x-rays can be used in the improvement operation 216. For example, operation 208 in FIG. 21 can correspond to FIGS. $20A_5$-$20C_5$ and/or FIGS. $20A_6$-$20C_6$. An example of operation 209b can be seen, for example, in FIG. $20C_{5X}$ and/or FIG. $20C_{5X}$.

The above disclosure focuses on the generation of a 3D wristband and shin brace target model; however, the systems and methods 100, 200, 300, 600, including any operation and/or feature described, contemplated, and/or illustrated herein, can be used to create 3D target models of orthoses, prostheses, implants, non-medical devices, non-medical structures, or any combination thereof.

For example, to illustrate the methods and techniques disclosed, the process of identifying reference and target objects for the modeling and/or manufacture of a wristband designed to exactly fit human wrists (e.g., according to fit accuracy parameters) is disclosed to illustrate a variation of designing, generating, validating, adjusting, and improving 3D target models of wrist bands to fit topologically isomorphic digital and/or physical target objects. To emphasize this point, the wristband in this disclosure is only purposed as an example to demonstrate the methods and techniques disclosed and is not intended to limit the scope of the invention in any way—the wristband examples disclosed and illustrated herein are simply exemplary applications of the methods and techniques disclosed.

The physical, digital, and digital representations of reference and target objects are exemplary only. Any reference and target objects can be imaged as described, illustrated, and contemplated herein. The reference and target objects and/or the 3D models can be represented in various forms, some of which may be quite different from those specifically referenced previously in the current embodiment without departing from the scope of this disclosure. One of ordinary skill will readily appreciate that the methods and techniques disclosed can be used with other specific arrangements of 3D models and template objects (reference and/or target objects) without departing from the scope of the present invention. For example, other variations of the description of the geometric design of the 3D model may differ from those disclosed herein without departing from the scope of the invention. The specific geometric constructs disclosed herein (e.g., geometric design definitions, 3D coordinate maps (applied to reference objects), modified 3D coordinate maps (applied to target objects), adjusted 3D coordinate maps (applied to target objects as modified, for example, in operation 212) are only representative of the geometric features used to create the 3D models. Geometric constructs different from those illustrated can be used to construct 3D reference and/or target models without departing from the scope of this invention.

The geometric features (e.g., dimensions, points, lines, surfaces, volumes) associated with the geometric design definitions, 3D coordinate mappings, lattice structures (e.g., 3D reference and/or target lattice structures), 3D models (e.g., 3D reference and/or target models), or any combination thereof) and the relative positions of such features, including the various outputs from the operations disclosed and/or contemplated herein will depend on, and can be customized to accommodate, for example, any reference and/or target object, for example, to meet a person or animal's medical and/or non-medical needs and/or desires. The orthoses, prostheses, implants, and fashion products disclosed can be custom fit to each target subject's anatomy; thus, although various geometric features, ranges and values are disclosed, each permutation of the disclosed geometric features, ranges and values and equivalents thereof is considered critical to the overall design of the 3D models (e.g., 3D reference and/or target models), as each combination of geometric features, ranges and values, when used together to create a model (and/or to manufacture a generated model) is critical to creating the 3D model desired. The design of each 3D target model will depend on a subject's unique physiological makeup. If the foregoing disclosure yet lacks clarity, every permutation of geometric features disclosed, including those features explicitly contemplated by this disclosure by way of being applicable to the creation of objects not specifically mentioned in the disclosure but nevertheless covered.

The claims are not limited to the exemplary embodiments shown in the drawings, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination, and each combination is hereby explicitly disclosed. All devices, apparatuses, systems, and methods described herein can be used for medical (e.g., diagnostic, therapeutic or rehabilitative) or non-medical purposes.

What is claimed is:

1. A method of creating a 3D model of a device, the method comprising:
    acquiring a digital representation of a first object;
    determining a geometric design definition that defines a first device 3D model configured to fit the first object, where the geometric design definition comprises geometric relationships between the first device 3D model and the first object;
    acquiring a digital representation of a second object different from the first object;
    morphing the first device 3D model to fit the second object to generate a second device 3D model configured to fit the second object;
    determining geometric relationships between the second device 3D model and the second object;
    validating the second device 3D model if the geometric relationships between the second device 3D model and the second object are proportional to the geometric relationships between the first device 3D model and the first object;
    adjusting a 3D coordinate map of the second device 3D model if the geometric relationships between the second device 3D model and the second object are not proportional to the geometric relationships between the first device 3D model and the first object;
    morphing the second device 3D model to generate a third device 3D model using the adjusted 3D coordinate map, where the third device 3D model is configured to fit the second object better than the second device 3D model based on a fit accuracy requirement;
    determining geometric relationships between the third device 3D model and the second object; and
    validating the third device 3D model if the geometric relationships between the third device 3D model and the second object are proportional to the geometric relationships between the first device 3D model and the first object.

2. The method of claim 1, where the geometric relationships between the first device 3D model and the first object comprise geometric fit accuracy parameters between the first device 3D model and the first object, and where the geometric relationships between the second device 3D model and the second object comprise geometric fit accuracy parameters between the second device 3D model and the second object.

3. The method of claim 2, where the geometric fit accuracy parameters between the first device 3D model and the first object comprise one or more maximum distances between the first device 3D model and the first object and/or one or more minimum distances between the first device 3D model and the first object.

4. The method of claim 2, where the geometric design definition further comprises non-geometric relationships between the first device 3D model and the first object, and where the method further comprises:
  determining non-geometric relationships between the second device 3D model and the second object; and
  validating the second device 3D model if the non-geometric relationships between the second device 3D model and the second object are proportional to the non-geometric relationships between the first device 3D model and the first object.

5. The method of claim 4, where the non-geometric relationships between the first device 3D model and the first object comprise non-geometric fit accuracy parameters between the first device 3D model and the first object, and where the non-geometric fit accuracy parameters between the first device 3D model and the first object comprise one or more maximum pressures applied by the first device 3D model to the first object and/or one or more minimum pressures applied by the first device 3D model to the first object.

6. The method of claim 1, where determining the geometric design definition comprises creating a 3D coordinate map of the first device 3D model comprising multiple points, where each point defines a point of the first device 3D model, and where the multiple points of the 3D coordinate map are created based at least partly on the geometric relationships between the first device 3D model and the first object.

7. The method of claim 1, where the device is at least one of an orthosis, prosthesis, implant, and non-medical device, and where the second object different from the first object comprises the second object being a modified first object or a different object altogether.

8. The method of claim 1, where morphing the first device 3D model to fit the second object comprises computing the geometric design definition with parameters associated with the second object.

9. The method of claim 8, where the parameters associated with the second object comprise coordinates of the second object and/or data representative of differences between the first object and the second object.

10. The method of claim 8, where the parameters associated with the second object comprise dimensions of the second object.

11. The method of claim 1, where morphing the first device 3D model to fit the second object comprises changing inputs of the geometric design to have parameters associated with the second object, and where the parameters associated with the second object comprise coordinates of the second object and/or data representative of differences between the first object and the second object.

12. The method of claim 1, where morphing the first device 3D model to fit the second object comprises using a geometric difference between the first object and the second object.

13. The method of claim 1, where morphing the first device 3D model to fit the second object comprises using a measurement of the first object and a measurement of the second object.

14. The method of claim 13, where morphing the first device 3D model to fit the second object comprises using a detected feature of the first object and a detected feature of the second object.

15. The method of claim 14, where morphing the first device 3D model to fit the second object comprises using an image of the first object and an image of the second object.

16. The method of claim 1, where morphing the first device 3D model to fit the second object comprises identifying a difference between a first object boundary and a second object boundary.

17. The method of claim 16, where morphing the first device 3D model to fit the second object comprises identifying a difference between a first device 3D model boundary and the second object boundary.

18. The method of claim 1, where morphing the first device 3D model to fit the second object comprises identifying a difference between a first device 3D model boundary and a second object boundary.

19. The method of claim 1, where morphing the first device 3D model to fit the second object comprises graphically modifying a visual representation of the first device 3D model to fit the second object.

20. The method of claim 1, where the first object is a first physical object, and where the second object is a second physical object.

21. A method of creating a 3D model, the method comprising:
  acquiring a digital representation of a reference object;
  determining a first geometric design definition that defines a 3D reference device model configured to fit the reference object, where the first geometric design definition comprises a fit accuracy requirement that defines the fit between the 3D reference device model and the reference object, a 3D reference coordinate map of the 3D reference device model based at least partly on the fit accuracy requirement, and geometric constructs of the 3D reference device model;
  acquiring a digital representation of a target object different from the reference object;
  mapping the 3D reference device model to the target object by modifying the 3D reference coordinate map of the 3D reference device model to fit the target object;
  changing the first geometric design definition to create a second geometric design definition that defines a first 3D target device model designed to fit the target object by substituting the 3D reference coordinate map of the first geometric design definition with the modified 3D reference coordinate map;
  validating the first 3D target device model if the fit between the first 3D target device model and the target object is the same as the fit between the 3D reference device model and the reference object as defined by the fit accuracy requirement;
  adjusting the modified 3D reference coordinate map if the fit between the first 3D target device model and the target object is not the same as the fit between the 3D reference device model and the reference object as defined by the fit accuracy requirement;
  changing the second geometric design definition to create a third geometric design definition that defines a second 3D target device model configured to fit the target object by substituting the modified 3D reference coordinate map of the second geometric design definition with the adjusted 3D reference coordinate map, where the second 3D target device model is configured to fit the target object better than the first 3D target device model based on the fit accuracy requirement;
  validating the second 3D target device model if the fit between the second 3D target device model and the target object is the same as the fit between the 3D reference device model and the reference object as defined by the fit accuracy requirement; and improving the determination of the first geometric design definition using one or more learning modules, where the one or more learning modules are configured to reference one or more validated 3D target device models, where a different geometric design definition is associated with each of the one or more validated 3D target device models, and where the one or more learning modules are configured to reference one or more of the different geometric design definitions associated with the one or more validated 3D target device models.

22. The method of claim 21, where the one or more learning modules are configured to reference one or more 3D reference device models, where a different geometric design definition is associated with each of the one or more 3D reference device models, and where the one or more learning modules are configured to reference one or more of the different geometric design definitions associated with the one or more 3D reference device models.

23. The method of claim 21, where validating the first 3D target device model comprises overlaying the 3D target device model on the digital representation of the target object and comparing one or more geometric measurements between the 3D target device model and the target object against the fit accuracy requirement.

24. The method of claim 21, where the fit accuracy requirement comprises a geometric fit accuracy requirement that defines one or more geometric relationships between the 3D reference device model and the reference object.

25. The method of claim 24, where the geometric fit accuracy requirement comprises a maximum distance between the 3D reference device model and the reference object or a minimum distance between the 3D reference device model and the reference object.

26. The method of claim 21, where the fit accuracy requirement comprises a non-geometric fit accuracy requirement that defines one or more non-geometric relationships between the 3D reference device model and the reference object.

27. The method of claim 26, where the non-geometric fit accuracy requirement comprises a maximum pressure applied by the 3D reference device model to the reference object or a minimum pressure applied by the 3D reference device model to the reference object.

28. The method of claim 21, where the 3D reference device model is at least one of an orthosis, prosthesis, implant, and non-medical device, where the first 3D target device model and the second 3D target device model are at least one of an orthosis, prosthesis, implant, and non-medical device, and where the target object different from the reference object comprises the target object being an altered version of the reference object or a different object altogether.

29. The method of claim 21, where modifying the 3D reference coordinate map of the 3D reference device model to fit the target object comprises determining dimensions between points of the 3D reference coordinate map and the target object.

30. The method of claim 29, where modifying the 3D reference coordinate map of the 3D reference device model to fit the target object comprises determining dimensions between points of the geometric constructs of the 3D reference device model and the target object.

31. The method of claim 21, where the geometric design definition comprises a computational model having inputs, and where the method further comprises morphing the 3D reference device model to fit the target object to generate the first 3D target device model by changing one or more of the inputs and computing the computational model with the one or more changed inputs.

32. The method of claim 31, where changing one or more inputs comprises substituting the 3D reference coordinate map of the first geometric design definition with the modified 3D reference coordinate map.

33. The method of claim 31, further comprising changing the one or more inputs of the computational model to have parameters associated with the target object.

34. The method of claim 21, where the reference and target objects are different people.

35. The method of claim 21, where the target object is isomorphically the same as the reference object.

36. A 3D modeling system, comprising:
one or more data acquisition devices; and
a modeling unit, wherein the modeling unit is configured to:
process a reference object and a target object acquired from the one or more data acquisition devices, where the target object is topologically isomorphic to the reference object;
design a 3D reference device model to fit the reference object by determining fit accuracy parameters, where the fit accuracy parameters comprise first relationships between the 3D reference device model and the reference object, and where the first relationships between the 3D reference device model and the reference object comprise a 3D reference coordinate map of the 3D reference device model;
compare the 3D reference device model to the target object;
determine, based on the comparison between the 3D reference device model and the target object, second relationships between the 3D reference device model and the target object;
compare the first relationships between the 3D reference device model and the reference object with the second relationships between the 3D reference device model and the target object;
generate a first 3D target device model by modifying the 3D reference device model based on the comparison between the first relationships and the second relationships, where modifying the 3D reference device model comprises generating a 3D target coordinate map of the first 3D target device model by morphing the 3D reference coordinate map to fit the target object;
compare the first 3D target device model to the target object;
determine, based on the comparison between the first 3D target device model and the target object, third relationships between the first 3D target device model and the target object;
validate the first 3D target device model if the third relationships between the first 3D target device model and the target object are within a threshold tolerance of the first relationships between the 3D reference device model and the reference object;
adjust the 3D target coordinate map of the first 3D target device model if the third relationships between the first 3D target device model and the target object are not within the threshold tolerance of the first relationships between the 3D reference device model and the reference object;
generate a second 3D target device model based at least partly on the adjusted 3D target coordinate map, where the second 3D target device model is configured to fit the target object better than the first 3D target device model based on a fit accuracy requirement;

validate the second 3D target device model if the adjusted relationships between the second 3D target device model and the target object are within the threshold tolerance of the first relationships between the 3D reference device model and the reference object; and improve the generation of the first 3D target device model using one or more learning modules, where the one or more learning modules are configured to reference one or more validated 3D target device models and the third relationships associated therewith.

37. The 3D modeling system of claim 36, where the 3D reference device model is at least one of an orthosis, prosthesis, implant, and non-medical device, and where the first 3D target device model and the second 3D target device model are at least one of an orthosis, prosthesis, implant, and non-medical device.

38. The 3D modeling system of claim 36, where modifying the 3D reference device model comprises morphing the 3D reference coordinate map of the 3D reference device model into a 3D target coordinate map that fits the target object.

39. The 3D modeling system of claim 36, where the reference object and the 3D reference device model are stored in a database, where if the first 3D target device model is validated, the first 3D target device model is added to the database as another 3D reference device model and the target object is added to the database as another reference object, and where if the second 3D target device model is validated, the second 3D target device model is added to the database as another 3D reference device model and the target object is added to the database as another reference object.

* * * * *